US008299103B2

(12) United States Patent
Bartolozzi et al.

(10) Patent No.: US 8,299,103 B2
(45) Date of Patent: Oct. 30, 2012

(54) COMPOUNDS WHICH SELECTIVELY MODULATE THE CB2 RECEPTOR

(75) Inventors: Alessandra Bartolozzi, Norwalk, CT (US); Eugene Richard Hickey, Danbury, CT (US); Doris Riether, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 137 days.

(21) Appl. No.: 12/791,213

(22) Filed: Jun. 1, 2010

(65) Prior Publication Data
US 2011/0136869 A1    Jun. 9, 2011

Related U.S. Application Data

(60) Provisional application No. 61/186,920, filed on Jun. 15, 2009.

(51) Int. Cl.
*A61K 31/42* (2006.01)
*A61K 31/41* (2006.01)
*C07D 285/08* (2006.01)
*C07D 277/28* (2006.01)
*C07D 261/04* (2006.01)
*C07D 257/00* (2006.01)

(52) U.S. Cl. ........ 514/361; 514/365; 514/380; 548/128; 548/205; 548/246; 548/251

(58) Field of Classification Search .................. None
See application file for complete search history.

(56) References Cited

U.S. PATENT DOCUMENTS

| | | | |
|---|---|---|---|
| 3,116,284 A | 12/1963 | Testa |
| 3,117,128 A | 1/1964 | Mooradian |
| 3,577,462 A | 5/1971 | Bruce et al. |
| 3,966,809 A | 6/1976 | Baker et al. |
| 4,257,954 A | 3/1981 | Schmidt et al. |
| 4,535,087 A | 8/1985 | Spatz |
| 4,672,065 A | 6/1987 | Spatz |
| 4,734,125 A | 3/1988 | Gehring et al. |
| 4,859,707 A | 8/1989 | Loftsson et al. |
| 5,256,658 A | 10/1993 | Hsi et al. |
| 5,428,037 A | 6/1995 | Pascal et al. |
| 5,475,130 A | 12/1995 | Sato et al. |
| 5,571,921 A | 11/1996 | Bender et al. |
| 5,583,147 A | 12/1996 | Ko et al. |
| 5,656,634 A | 8/1997 | Chang et al. |
| 5,847,153 A | 12/1998 | Warpehoski et al. |
| 5,958,940 A | 9/1999 | Rane et al. |
| 5,968,929 A | 10/1999 | Blythin et al. |
| 6,057,371 A | 5/2000 | Glennon |
| 6,176,442 B1 | 1/2001 | Eicher et al. |
| 6,221,866 B1 | 4/2001 | Brendel et al. |
| 6,355,653 B1 | 3/2002 | Trottmann et al. |
| 6,359,009 B1 | 3/2002 | Diehl et al. |
| 6,410,792 B1 | 6/2002 | Connell et al. |
| 6,414,011 B1 | 7/2002 | Hogenkamp et al. |
| 6,437,177 B1 | 8/2002 | Warpehoski et al. |
| 6,453,795 B1 | 9/2002 | Eicher et al. |
| 6,528,529 B1 | 3/2003 | Brann et al. |
| 6,573,278 B2 | 6/2003 | Mittendorf et al. |
| 6,610,711 B2 | 8/2003 | Armer et al. |
| 6,737,418 B2 | 5/2004 | Hogenkamp et al. |
| 7,476,756 B2 | 1/2009 | Almario-Garcia et al. |
| 7,585,881 B2 | 9/2009 | Edwards et al. |
| 7,595,397 B2 | 9/2009 | Zindell et al. |
| 7,928,123 B2 | 4/2011 | Berry et al. |
| 7,935,715 B2 | 5/2011 | Berry et al. |
| 8,048,899 B2 | 11/2011 | Bartolozzi et al. |
| 8,173,638 B2 | 5/2012 | Berry et al. |
| 8,178,568 B2 | 5/2012 | Regan et al. |
| 2002/0099035 A1 | 7/2002 | Sandanayaka et al. |
| 2004/0067999 A1 | 4/2004 | Block et al. |
| 2004/0242913 A1 | 12/2004 | Ducray et al. |
| 2005/0059663 A1 | 3/2005 | Martin et al. |
| 2005/0182108 A1 | 8/2005 | Carson et al. |
| 2006/0061726 A1 | 3/2006 | Okuyama |
| 2006/0079557 A1 | 4/2006 | Dolle et al. |
| 2007/0021403 A1 | 1/2007 | Abouabdellah et al. |
| 2007/0021430 A1 | 1/2007 | Chen et al. |
| 2007/0093501 A1 | 4/2007 | Kubo et al. |

(Continued)

FOREIGN PATENT DOCUMENTS

CH        312963 A    3/1956

(Continued)

OTHER PUBLICATIONS

Beilstein Database—Beilstein Registry No. 1084348. CAS Registry No. 6125-38-8. Beilstein Institute for Organic Chemistry. 1966, Abstract.
Beilstein Database—Beilstein Registry No. 1179643. CAS Registry No. 54890-73-2. Beilstein Institute for Organic Chemistry. 1974, Abstract.
Beilstein Database—Beilstein Registry No. 5396840. CAS Registry No. 54890-82-3. Beilstein Institute for Organic Chemistry. 1974, Abstract.
Beilstein Database—Beilstein Registry No. 5398283. CAS Registry No. 68558-02-01. Beilstein Institute for Organic Chemistry. 1978, Abstract.
Beilstein Database—Beilstein Registry No. 857451. CAS Registry No. 37901-58-9. Beilstein Institute for Organic Chemistry. 1972, Abstract.
Carenzi, A, et al., "New Isoxazole Derivatives Provided with Antihypertensive Activity". Arzneimittel-Forschung, vol. 39, No. 6, 1989, p. 624-646.

(Continued)

*Primary Examiner* — Kamal Saeed
(74) *Attorney, Agent, or Firm* — Michael P. Morris; Anthony P. Bottino

(57) ABSTRACT

Compounds of formula (I)

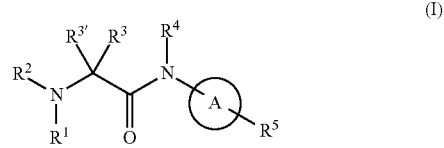

are disclosed. Compounds according to the invention bind to and are agonists, antagonists or inverse agonists of the CB2 receptor, and are useful for treating inflammation. Those compounds which are agonists are additionally useful for treating pain.

15 Claims, 2 Drawing Sheets

U.S. PATENT DOCUMENTS

| | | | |
|---|---|---|---|
| 2007/0179126 A1 | 8/2007 | Casellas et al. |
| 2007/0191340 A1 | 8/2007 | Zindell et al. |
| 2007/0213311 A1 | 9/2007 | Li et al. |
| 2008/0039464 A1 | 2/2008 | Berry et al. |
| 2008/0064690 A1 | 3/2008 | Atkinson et al. |
| 2008/0081342 A1 | 4/2008 | Fung |
| 2008/0081822 A1 | 4/2008 | Berry et al. |
| 2009/0163545 A1 | 6/2009 | Goldfarb |
| 2009/0275611 A1 | 11/2009 | Riether et al. |
| 2010/0009964 A1 | 1/2010 | Berry et al. |
| 2010/0029644 A1 | 2/2010 | Riether et al. |
| 2010/0076029 A1 | 3/2010 | Bartolozzi et al. |
| 2010/0081644 A1 | 4/2010 | Bartolozzi et al. |
| 2010/0261708 A1 | 10/2010 | Cirillo et al. |
| 2010/0331304 A1 | 12/2010 | Berry et al. |
| 2011/0071127 A1 | 3/2011 | Berry et al. |
| 2011/0071196 A1 | 3/2011 | Bartolozzi et al. |
| 2011/0124696 A1 | 5/2011 | Regan et al. |
| 2011/0130431 A1 | 6/2011 | Berry et al. |
| 2011/0136869 A1 | 6/2011 | Bartolozzi et al. |
| 2011/0190256 A1* | 8/2011 | Cirillo et al. ............... 514/210.2 |
| 2011/0312932 A1 | 12/2011 | Bartolozzi et al. |
| 2011/0312944 A1 | 12/2011 | Bartolozzi et al. |
| 2012/0010184 A1 | 1/2012 | Bartolozzi et al. |
| 2012/0142666 A1 | 6/2012 | Hickey et al. |
| 2012/0142677 A1 | 6/2012 | Berry et al. |

FOREIGN PATENT DOCUMENTS

| | | |
|---|---|---|
| DE | 1080563 B | 12/1957 |
| EP | 0628555 | 12/1994 |
| EP | 0929519 | 7/1999 |
| EP | 0970046 A1 | 1/2000 |
| EP | 1790641 A1 | 5/2007 |
| FR | 2866885 A1 | 9/2005 |
| FR | 2872813 A1 | 1/2006 |
| GB | 853799 A | 11/1960 |
| GB | 884258 A | 12/1961 |
| GB | 1237126 A | 6/1971 |
| JP | 61017955 | 2/1986 |
| JP | 61027905 U | 2/1986 |
| JP | 61027955 A | 2/1986 |
| JP | 61126071 A | 6/1986 |
| JP | 2003155285 | 5/2003 |
| WO | 9405628 | 3/1994 |
| WO | 9407607 | 4/1994 |
| WO | 9626925 A1 | 9/1996 |
| WO | 9712683 | 4/1997 |
| WO | 9712687 | 4/1997 |
| WO | 9720590 | 6/1997 |
| WO | 9746556 | 12/1997 |
| WO | 9808295 | 2/1998 |
| WO | 9811097 A1 | 3/1998 |
| WO | 9813340 | 4/1998 |
| WO | 9838163 A1 | 9/1998 |
| WO | 0008015 A2 | 2/2000 |
| WO | 0100573 | 1/2001 |
| WO | 0129007 | 4/2001 |
| WO | 0164651 | 9/2001 |
| WO | 02051806 | 7/2002 |
| WO | 02088089 A1 | 7/2002 |
| WO | 02062750 | 8/2002 |
| WO | 03037274 A2 | 5/2003 |
| WO | 03055482 | 7/2003 |
| WO | 03000807 | 12/2003 |
| WO | 04000807 | 12/2003 |
| WO | 2004014370 A2 | 2/2004 |
| WO | 2004014825 | 2/2004 |
| WO | 2004014902 A2 | 2/2004 |
| WO | 2004018433 | 3/2004 |
| WO | 2004026301 A1 | 4/2004 |
| WO | 2004029027 | 4/2004 |
| WO | 2004042351 A2 | 5/2004 |
| WO | 2004050643 | 6/2004 |
| WO | 2004060882 | 7/2004 |
| WO | 2004099200 A1 | 11/2004 |
| WO | 2004099205 | 11/2004 |
| WO | 2005027837 | 3/2005 |
| WO | 2005040355 | 5/2005 |
| WO | 2005077345 A1 | 8/2005 |
| WO | 2005077368 A2 | 8/2005 |
| WO | 2005077373 A2 | 8/2005 |
| WO | 2005085227 | 9/2005 |
| WO | 2006012227 | 2/2006 |
| WO | 2006060461 | 6/2006 |
| WO | 2006074445 A2 | 7/2006 |
| WO | 2006080040 | 8/2006 |
| WO | 2006095159 | 9/2006 |
| WO | 2006100502 | 9/2006 |
| WO | 2006117461 A2 | 11/2006 |
| WO | 2007020502 A2 | 2/2007 |
| WO | 2007054770 A2 | 5/2007 |
| WO | 2007070760 | 6/2007 |
| WO | 2007070760 A2 | 6/2007 |
| WO | 2007080382 A1 | 7/2007 |
| WO | 2007102059 | 9/2007 |
| WO | 2007118041 | 10/2007 |
| WO | 2007140385 A2 | 12/2007 |
| WO | 2008014199 A | 1/2008 |
| WO | 2008023159 A1 | 2/2008 |
| WO | 2008039645 A | 4/2008 |
| WO | 2008048914 A1 | 4/2008 |
| WO | 2008064054 | 5/2008 |
| WO | 2008098025 A1 | 8/2008 |
| WO | 2008104994 A2 | 9/2008 |
| WO | 2009055357 A1 | 4/2009 |
| WO | 2009061652 A1 | 5/2009 |
| WO | 2009077533 A1 | 6/2009 |
| WO | 2009105509 A1 | 8/2009 |
| WO | 2009140089 A2 | 11/2009 |
| WO | 2010005782 A1 | 1/2010 |
| WO | 2010036630 A2 | 4/2010 |
| WO | 2010036631 A2 | 4/2010 |
| WO | 2010077836 A2 | 7/2010 |
| WO | 2010096371 A2 | 8/2010 |
| WO | 2010147791 A1 | 12/2010 |
| WO | 2010147792 A2 | 12/2010 |
| WO | 2011037795 | 3/2011 |
| WO | 2011088015 A1 | 7/2011 |
| WO | 2011109324 A1 | 9/2011 |
| WO | 2012012307 A1 | 1/2012 |

OTHER PUBLICATIONS

Chem Abstract—Accession No. 126:89390, Abstract of JP8311026, Kumaiai Chemical Industry Co., Nov. 26, 1996.

Hadjipavlou-Litina, D. et al., "Thiazolyl-N-Substituted Amides: A group of effective anti-inflammatory agents with potential for local anesthetic properties. Synthesis, Biological Evaluation, and a QSAR Approval." Drug Development Research, Vo. 48, 1999, p. 53-60-.

International Search Report and Written Opinion for PCT/US2010/037697 mailed Jul. 1, 2011.

Kano, S. et al., "Formation of Some Heterocycles through Ring Transformation of 1-Arylaxetidin-2-Ones." Heterocycles, vol. 8, No. 1, Dec. 30, 1977, p. 411-416.

U.S. Appl. No. 13/037,422, filed Mar. 1, 2011, Inventor: Monika Ermann.

ChemAbstracts, Ukraine. Order Nos. T6110295, T5962700, T5962703 abstract and "Enamine Screening Library", Jan. 1, 2009, Enamine, 23 Alexandra Matrosova St., 01103 Kiev, Ukraine.

Abstract in English for JP2003155285, May 27, 2003, Inventor: T. Makoto.

U.S. Appl. No. 13/022,866, filed Feb. 8, 2011, Inventor: Angela Berry.

Abstract in English for JP 61-027905, Feb. 7, 1986, and WO199626925, Sep. 1996, Derwent Abstract.

Abstract in English for JP 61-027955, Feb. 7, 1986, Derwent.

Anisimov, A. V. et al., "Synthesis of Sulfonyl and Sulfenyl Derivatives of Pyridine and 1,2,4-Triazole". Russian Journal of Organic Chemistry, 2006, vol. 42, No. 6, pp. 918-921.

Aranapakam, V. et al., "Synthesis and Structure-Activity Relationship of a-Sulfonylhydroxamic Acids as Novel, Orally Active Matrix Metalloproteinase Inhibitors for the treatment of Osteoarthritis", J. Med. Chem., 2003, vol. 46, p. 2361.

Aranapakam, V. et al., "Synthesis and Structure-Activity relationship of n-Substituted 4-Arylsulfonylpiperidine-4-hydroxamic Acids as Novel, Orally Active matrix Metalloproteinase Inhibitors for the treatment of Osteoarthritis", J. Med. Chem., 2003, vol. 46, p. 2376.
Aranapakam, V., et al., "Synthesis and Structure-Activity relationships of 4-alkynyloxy Phenyl Sulfanyl, Sulfinyl, and Sulfonyl Alkyl Hydroxamates as Tumor Necrosis Factor-a Converting Enzyme and Matrix Metalloproteinase Inhibitors", J. Med. Chem., 2004, vol. 47, p. 6255.
Arevalo-Martin, A. et al., "Therapeutic Action of Cannabinoids in a Murine model of Multiple Sclerosis", J. of Neuroscience, 2003, vol. 23, No. 7, p. 2511.
Atwell, G. J. et al., "Relationships between Structure and Kinetics of Cyclization of 2-Aminoaryl Amides: Potential Prodrugs of Cyclization-Activitated Aromatic Mustards"., XP-002465787, J. Med. Chem, 1994, 37, 371-380.
Bair, K. W. et al., "(1-pyrenylmethyl)amino alcohols, a new class of antitumor DNA intercalators. Discovery and intial amine side chain structure-activity studies". Jornal of Medicinal Chemistry, vol. 33, 1990, pp. 2385-2393.
Baker, D. et al., "Cannabinoids control spasticity and tremor in a multiple sclerosis model", Nature, 2000, vol. 404, p. 84.
Baltzly, R. et al., "The preparation of N-mono-substituted and unsymmetrically disubstituted piperzines". Journal of American Chemical Society, vol. 66, 1944, pp. 263-265.
Baltzly,R. et al., "Unsymmetrically substituted piperazines. V. Piperazine ureas". The Journal of the American Chemical Society, vol. 76, 1954, pp. 1165-1166.
Balzarini, J. et al., "Antiretroviral activity of semisynthetic derivatives of glycopeptide antibiotics". J. Med. Chem., 2003, vol. 46, No. 13, pp. 2755-2764.
Binisti, C. et al., "Structure-Activity relationships in platelet-activating factor (PAF). 11—From PAF-antagonism to phospholipase A2 inhibition: syntheses and structure-activity relationships in 1-arylsulfamido-2-alkylpiperazines", Eur. J. Med. Chem., 2001, vol. 36, p. 809.
Brown, P. J. et al., "A Ureido-Thioisobutyric Acid (GW9578) Is a Subtype-Selective PPARa Agonist with Potent Lipid-Lowering Activity", J. Med. Chem. 1999, vol. 42, p. 3785.
Bruche, L. et al., "1,3-Dipolar Cycloadditions of 3,5-Dichloro-2,4,6-trimethylbenzonitrile Oxide to Phenylsulfonylallenes". Journal of Organic Chemistry, vol. 50, 1985, pp. 3206-3208, p. 3206, compounds 5a and 5b.
Buckley, N. E. et al., "Immunomodulation by cannabinoids is absent in mice deficient for the cannabinoid CB2 receptor", Eur. J. Pharmacology, 2000, vol. 396, p. 141.
Caplus—1990:497413, Zara-Kaczian, Acta Chimica Hungarica.
Caplus—RN 112298-90-5 (Tommasi), retrieved from CAPLUS on Jan. 2, 2009.
Caplus—RN 262371-16-4 (Organ), retrieved from CAPLUS on Jan. 2, 2009.
Caplus—RN 57992-82-2 (Babayan), retrieved from CAPLUS on Jan. 2, 2009.
Cartwright, D., et al., "Abnormal Nucleophillic substitution in 3-trichloromethylpyridine, its N-oxide and 3,5-Bis(trichloromethyl)pyridine". Tetrahedron, Elsevier Science Publishers, Amsterdam, vol. 51, No. 47, 1995, pp. 12791-12796.
Chang, M. Y. et al, "Reaction of different a-sulfonyl acetamides with methyl acrylate". Tetrahedron 58 (2002) p. 5075-5080.
ChemAbstract: 246020-62-2 registry copyright ACS on STN, entered 1999. CHEMCATS.
Chen, D. et al., "Preparation, properties, and synthetic potentials of novel boronates in a flourous version (flourous boronates)". Organic Letters, vol. 4. No. 6, 2002, pp. 1003-1005.
Clark, N. G. et al., "The Fungicidal Activity of Substituted Acetanilides and Related Compounds". Biochemical Journal, 1953, vol. 55, p. 839-851.
Cockcroft, X. L. et al., "Phthalazinones 2: optimization and synthesis of novel potent inhibitors of ply(ADP-ribose)polymerase". Bioorganic & Medicinal Chemistry Letters, 16, 2006, pp. 1040-1044.
Dav, Jr., R. A. et al., "Polarography of phenyl 2-thienyl and 2,2'-dithienyl ketones". 1953.

El-Hawash, S. A. M., et al., "Synthesis and invitro-Anticancer and Antimicrobial Evaluation of Some Novel Quinoxalines Derived from 3-Phenylquinoxaline-2(1H)-thione". Arch. Pharm. Chem. Life Sci, 2006, 339, p. 437-447.
EP Office Action dated Mar. 22, 2010.
Ermann, M. et al., "Arylsulfonamide CB2 receptor agonists: SAR and optimization of CB2 selectivity", Bioorganic and Medicinal Chemistry Letters 18 (2008) 1725-1729.
Ermann, M., et al., Moscone Conv.Ctr. "Discovery of a novel class of CB2 receptor agonists". Presented at the Cambridge Healthcare Institute's 15th International Molecular Medicine Tri-Conference, Moscone Convention Center, San Francisco, CA, USA. Mar. 25-28, 2008.
Ermann, M., et al., UK, "Discovery of a novel class of CB2 receptor agonists". Presented at the 14th SCI-RSC Medicinal Chemistry Symposium, Churchill College, Cambridge, UK, Sep. 23-26, 2007.
Evans, W. J. et al., "A Rearrangement of Carbamyl-sulphones and -sulphides". Journal of the Chemical Society, 1936, p. 329-331.
Faucher, A. M. et al., "Discovery of Small-Molecule Inhibitors of the ATPase Activity of Human Papillomavirus E1 Helicase", J. Med. Chem., 2004, vol. 47, p. 18.
Field, L. et al., "Grignard Reagents of Sulfones. IV. Reactions with Nitriles, Esters and an Isocyanate". Journal of American Society, vol. 78, 1956, p. 4389-4394.
Field, L., et al., "Methyl p-Tolyl Sulfone", Organic Syntheses, Coll. vol. 4, p. 674, 1963; vol. 38, p. 62, (1958).
Fringuelli, F. et al., "Solvent-Free A1(OTi)3-catalyzed aminolysis of 1,2-Epoxides by 2-picolylamine: a key step in the synthesis of ionic liquids". Journal of Organic Chemistry, vol. 69, 2004, pp. 7745-7747.
Gao, M., et al "Synthesis of new carbon-11 labeled benzoxazole derivatives for PET imaging of 5-HT3 receptor", Science Direct, European Journal of Medicinal Chemistry, 43, 2008, pp. 1570-1574.
Gartst, M., et al., "Hydroformylation of bisolefinic amine derivatives catalyzed by cobalt and rhodium". Journal of Organic Chemistry, vol. 46, 1981, pp. 4433-4438.
Gavalda, et al N-Sulfonyl hydroxamate derivatatives as inhibitors of class II fructose-1, 6-diphosphate aldolase, Bioorganic & Medicinal Chemistry Letter, 2005, vol. 15, No. 24, pp. 5375-5377.
Goldschmidt,St. et al., "Biphenyl derivatives II. Basic 4-Biphenyl Compounds". Receuil Travaux Chimiques Des Pays-Bas, vol. 69, 1950, pp. 1109-1117.
Grothe, V. W. et al. "Effect of Potassium Sulfhydrate etc. on Chloroacetylanilides". Archiv der Pharmazie (Weinheim), vol. 238, 1980, p. 600-614.
Hanus, L. et al., "HU-308: A specific agonist for CB2, a peripheral cannabinoid receptor", PNAS, 1999, vol. 96, No. 25, p. 14228.
Herndon, J. L. et al., "Ketanserin analogues. Structure-affinity relationships for 5-HT2 and 5-HT1c serotoninin receptor binding". J. Med. Chem, 1992, vol. 35, No. 26, pp. 4903-4910.
Huang, X. et al., "A Novel Synthesis of Sulfones via the O,O-Diethylphosphorotellurite Ion-assisted Coupling of Arenesulfonyl Chlorides with Active Halides". Synthetic Communications, 20(15), 2291-2291-2295 (1990).
Ibrahim, M. M. et al., "Activation of CB2 cannabinoid receptors by AM1241 inhibits experimental neuropathic pain: Pain inhibition by receptors not present in the CNS", PNAS, 2003, vol. 100, No. 18, p. 10529.
Iddon, B. et al., "Condensed thiophen ring systems. Part SVII. A new synthesis of 10H-indeno[1,2-b][1]benzothiophen". Journal of the Chemical Society. Perkin Transactions 1, Chemical Socieity. Letchworth, GB. vol. 21, Jan. 1, 1974, pp. 2505-2508. ISSN: 0300-922X, p. 2506; compound 8.
Sheehan, J.C. et al, The Synthesis and Reactions of Some Substitued Beta-Lactams, 1951, Journal of the American Chemical Society, 73, 1761-1765.
Iddon, B. et al., "Polyhalogenoaromatic Compounds. Part 42. C N.m.r. Spectra of Polyhalogeno-pyridines and -pyrimidines". XP009094360, Ramage Laboratories, Dept of Chemistry and Applied Chemistry, University of Salford, Salford M5 4WT, Journal of the Chemical Society, Perkin Transactions 1, 1980, p. 1370.
Igarashi, J. et al., "Improved synthesis of quinine alkaloids with the Teoc protective group". Tetrahedron letters, Elsevier, Amsterdam, vol. 46, No. 37, 2005, pp. 6381-6384.

Ishii, K. et al., "Smiles Rearrangement of 2-(1-Methyl-1H-tetrazol-5-ylthio)acetamides and their Sulfonyl Derivatives". XP009094359, Chem. Pharm. Bull. 39(12) 3331-3334 (1991).

Johansen et al., AMPA Receptor Agonists: Resolution, Configurational Assignment, and Pharmacology of (+)-(S)- and (−)-(R)-2-Amino-3-(3-Hydroxy-5-(2-Pyridyl) Isoxazol-4-yl)Propionic Acid (1-Py-AMPA); Chirality, New York, 1997, vol. 9, No. 3, pp. 274-280.

Katoh, A., et al., "Synthesis of 6-(Bromoacetyl)Amino-2,3-Dimorpholino-Quinoxaline and Application to a new Fluorescence Derivatization Reagent of Fatty Acids for the High-Performance Liquid Chromatographic Analysis", Heterocycles, 1999, vol. 50, No. 1, p. 299.

Katz, L., et al., "Hydrazine Derivatives. II. Ortho-Mercapto-Pyridinecarbohydrazides", Contribution from Schenley Laboratories, Inc., 1953, p. 711.

Klein, T. W., et al., "The Cannabinoid system and immune modulation", J. Leukocyte Biology, 2003, vol. 74, p. 486.

Kolehmainen, E. et al., "a-Phenylsulfonyl-N-arylacetamides (a-phenylsulfonylacetanilides): H, C and N NMR spectral characterization". XP002465784, Magnetic Resonance in Chemistry, 2000, 38: 384-385.

Krutosikova, A. et al., "Furan derivatives. LV. Preparation of 5-aryl-2-furfuryl phenyl and 5-aryl-2-furfuryl 4-tolyl sulfones". Chemick Zvesti—Chemical Papers, Veda Bratislava, SK. vol. 28, Jan. 1, 1974, pp. 414-417, ISSN: 0366-6352, p. 414, compounds I-IX.

Lambeng, N. et al., "Discovery of a Novel Piperidinyl-Sulfonyl Benzoic Ester, Active as CB1 Agonist" Poster. 231st ACS National Meeting, Atlanta, GA. Mar. 26-30, 2006.

Lesser, R. et al. "Homo-?-oxythionaphthene (4-Ketoisothiochromane". Charlottenburg, Industrial Chemistry Laboratory of the Institute of Technology, 1923, pp. 1642-1648.

Lutz, R. E. et al., "Antimalarials. Some piperazine derivatives". Journal of Organic Chemistry, vol. 12, 1947, pp. 771-775.

Mahmoud, A. M. et al., "Synthesis and Biological Activity of Some new 2-(N-Substituted Carboxamidomethyl Thio)-Naphth[1,2-d]Oxazoles—Part V". XP002068972, J. Indian Chem. Soc., vol. LIX, May 1982, pp. 675-677.

Malan Jr., T. P., et al., "CB2 cannabinoid receptor-mediated peripheral antinociception", Pain, 2001, vol. 93, p. 239.

Markley, L. D., et al., "Antipicornavirus activity of substituted Phenoxybenzenes and Phenoxypyridines", J. Med. Chem., 1986, vol. 29, p. 427.

Marx, I. E. et al., "Discovery of a-amidosulfones as potent and selective agonists of CB2: Synthesis, SAR, and pharmacokinetic properties". Bioorganic and Medicinal Chemistry Letters, 2008. In press, accepted manuscript.

Messinger, P., "Sulfones via Mannich bases" Archiv der Pharmazie, 1973, vol. 306, No. 8, pp. 603-610, ISSN: 0365-6233. p. 607, compounds 28A-29C.

Miroshnikova, O.V. et al., "Structure-activity relationships in the series of eremomycin carboxamides". Journal of Antibiotics, vol. 53, No. 3, 2000, pp. 286-293.

Miyano, S, et al., "Kinetic Resolution of Racemic b-Hydroxy Amines by Enantioselective N-Oxide formation". Journal of Organic Chemistry, 1985, vol. 50, pp. 4350-4360.

Mohler, et al., "Nonsteroidal tissue selective androgen receptor modulators: a promising class of clinical candidates" University of Tennessee Health Science Center, Expert Opinion of Therapeutic Patents; Nov. 2005, vol. 15, No. 11, pp. 1565-1585.

Nackley, A. G., et al., "Selective Activation of Cannabinoid CB2 Receptors Suppresses Spinal FOS Protein Expression and Pain Behavior in a rat Model of Inflammation", Neuroscience, vol. 119, 2003, p. 747.

Office Action from the EPO dated Mar. 22, 2010.

Pollard, C. B. et al., "Some amides of piperazines". Journal of American Chemical Society, vol. 75, 1953, p. 491.

Revesz, L. et al., "Novel CCR1 antagonists with oral activity in the mouse collagen induced arthritis". Bioorganic and Medicinal Chemistry Letters, vol. 15, 2005, pp. 5160-5164.

Sakuraba, S, et al., "Efficient asymmetric hydrogenation of a-amino ketone derivatives. A highly enantioselective synthesis of phenylephrine, levamisole, carnitine and propranolol". Chemical and Pharmaceutical Bulletin, Pharm. Society of Japan, 1995, vol. 43, No. 5, pp. 738-747.

Schaefer, H. et al. "On the Synthesis of 4-aminoquinolines and -quinolinones-(2) from Anthranilonitrile" Chemistry Department of the Technical University of Dresden, Journal for Practical Chemistry, vol. 321, No. 4, 1979, pp. 695-698.

Seidel M. C. et al., "Reaction of Substituted 2-carbethoxyacetyl-aminopyridines and similar compounds with triethyl orthoformate and zinc chloride". Rohm and Haas Company, Spring House, Pennsylvania 19477, 1989.

Sharkey, K. A. et al., "CB2 cannabinoid receptors: new vistas", The first International Conference devoted to studies of the CB2 cannabinoid receptor. Banff, Alberta, Canada, May 31-Jun. 3, 2007.

Sisko, J. et al., "An investigation of imidazole and oxazole synthesis using aryl-substituted TosMIC reagents". The Journal of Organic Chemistry, vol. 65, No. 5, Mar. 10, 2000, pp. 1516-1624, ISSN: 022-3263, p. 1523, table 5, compound 69.

Smith, S. R., et al., "The anti-inflammatory activities of cannabinoid receptor ligands in mouse peritonitis models", Eur. J. Pharmacology, 2001, vol. 432, p. 107.

Strating, J., et al. "Nucleophilic Additions to Bis-Tertiobutyl Sulfonyl Acetylene (Properties of the sulfonyl group XLIV 1)". University of Groningue, Organic Chemistry Laboratory, 1954, pp. 709-716.

Swanson, D. M. et al., "Identification and biological evaluation of 4-*(3-trifluoromethylpyridin-2-yl)piperzine-1-carboxylic acid (5-trifluoromethylpyridin-2-yl)amide, a high affinity TRPV1 (VR1) vanilloid receptor antagonist". Journal Med. Chem, 2005, 48, pp. 1857-1872.

Tegley, et al., "Discovery of Novel Hydroxy-Thiazoles as HIF-alpha Prolyl Hydroxylase Inhibitors: SAR, Synthesis, and Modeling Evaluation," Bioorganic & Medicinal Chemistry Letters, Pergamon, Elsevier Science, GB, vol. 18, No. 14, 2008, pp. 3925-3928.

Todorova, T. R., et al "Ring-enlargement and ring-opening reactions of 1,2-thiazetidin-3-one 1,1,-dioxides with ammonia and primary amines as nucleophiles". Helvetica Chimica Acta, vol. 82, 1999, pp. 354.

Troeger, J. et al., "Regarding sulfonated Butyric Acids". From the Laboratory for Pharmaceutical and Synthetic Chemistry of the Braunschweig Institute of Technology.1991, 40, 506.

Troeger, J. and Uhde, R., "Lieber sulfonirte buttersauren", J. Prakt. Chem., 1899, 1991, vol. 59, p. 320.

Tweit, R. C., et al., "Synthesis of Antimicrobial Nitroimidazolyl 2-Sulfides, -Sulfoxides, and -Sulfones". Dept. of Chemical and Biological Research, Searle Laboratories, Chicago, IL, USA, Mar. 29, 1973, pp. 1161-1169.

Ueda, Y., et al., "Involvement of cannabinoid CB2 receptor-mediated response and efficacy of cannabinoid CB2 receptor inverse agonist, JTE-907, in cutaneous inflammation in mice", Eur. J. Pharmacology, 2005, vol. 520, p. 164.

Van Sickle, M. D., et al., "Identification and Functional Characterization of Brainstem Cannabinoid CB2 receptors", Science, 2005, vol. 310, p. 329.

Vogtle, M. M. et al., "An efficient protocol for the solid-phase synthesis of malondiamides". Molecules, 2005, 10, pp. 1438-1445. XP002481324.

Walker, G.N. et al., "Synthesis of varied heterocyclic and substituted aryl alkyl secondary amines, related Schiff bases, and amides". Journal of Medicinal Chemistry, vol. 9, 1966, pp. 624-630.

Wang, Y. et al., "Rapid and efficient synthesis of 1,2,4-oxadiazoles utilizing polymer-supported reagents under microwave heating". Organic Letters, vol. 7, No. 5, Mar. 3, 2005, pp. 925-928, ISSN: 1523-7060, p. 927, compounds 14,15.

Watson, R. J., et al., "An enantioselective synthesis of sulphonamide hydroxamic acids as matrix metalloproteinase inhibitors", Pergamon, Tetrahedron Letters 43 (2002) 683-685.

Yang, G. et al., "Synthesis and Bioactivity of Novel Triazolo [1,5-a]Pyrimidine Derivatives[3]". XP002465786, Heteroatom Chemisry, vol. 12, No. 6, 2001, p. 491-496.

Yokoyama, M. et al., "A regioselective synthesis of 3 5 disubstituted isoxazoles". Journal of the Chemical Society Perkin Transactions I, No. 1, 1986, pp. 67-72, ISSN: 0300-922X, pp. 68,69, compounds 6A, 14A.

Yordanova, K. et al. "New method for the synthesis of 2,4-disubstituted morpho-lines". Chemical Abstracts, vol. 97, No. 17, Oct. 25, 1982, Columbus, Ohio, USA Chemical Abstracts, vol. 97, No. 17, Oct. 25, 1982, Columbus, Ohio, vol. 115, No. 7, pp. 2635-2642.

Zhang, B. and Breslow, R., "Ester Hydrolysis by a Catalytic Cyclodextrin Dimer Enzyme Mimic with a Metallobipyridyl Linking Group", J. Am. Chem. Soc., 1997, vol. 119, p. 1676.

Zimmer, A. et al., "Increased mortality, Hypoactivity, and hypoalgesia in cannabinoid CB1 receptor knockout mice", Proc. Natl. Acad. Sci. USA, 1999, vol. 96, p. 5780.

Zindell, R. et al., "Discovery of a novel class of CB2 agonists". General Poster Session. The 235th ACS National Meeting, New Orleans, LA, USA. Apr. 6-10, 2008.

* cited by examiner

COMPOUNDS WHICH SELECTIVELY MODULATE THE CB2 RECEPTOR

APPLICATION DATA

This application claims benefit to U.S. provisional application Ser. No. 61/186,920 filed Jun. 15, 2009.

BACKGROUND OF THE INVENTION

1. Technical Field

The present invention relates to novel compounds which modulate the CB2 receptor and their use as medicaments.

2. Background Information

WO2008014199, WO2008039645 discuss the CB2 receptor, and the therapeutic uses of the CB2 receptor agonist compounds disclosed therein. It is believed that the highly selective activation of the CB2 receptor with an agonist may offer avenues of harnessing the beneficial effects while avoiding the adverse effects seen with dual CB1/CB2 cannabinoid receptor agonists (see e.g. Expert Opinion on Investigational Drugs (2005), 14(6), 695-703). It is desirable therefore to provide agonists of CB2 with minimized CB1 activity.

PCT Application Number PCT/US09/34464 discloses compounds having CB2 agonist activity. The compounds of the present invention differ structurally from the above disclosed compounds, for example the present R5 in the formula (I) disclosed hereinbelow. Additionally, the compounds of the present invention have lower CB1 activity than the compounds disclosed in the cited art.

BRIEF SUMMARY OF THE INVENTION

The present invention provides novel compounds which bind to and modulate the CB2 receptor and have lower CB1 receptor activity. The invention also provides methods and pharmaceutical compositions for treating inflammation by way of the administration of therapeutic amounts of the compounds of the invention. Lastly, the invention provides a method and pharmaceutical compositions for treating pain by way of the administration of therapeutic amounts of the compounds of the invention.

DETAILED DESCRIPTION OF THE INVENTION

Figure 1:
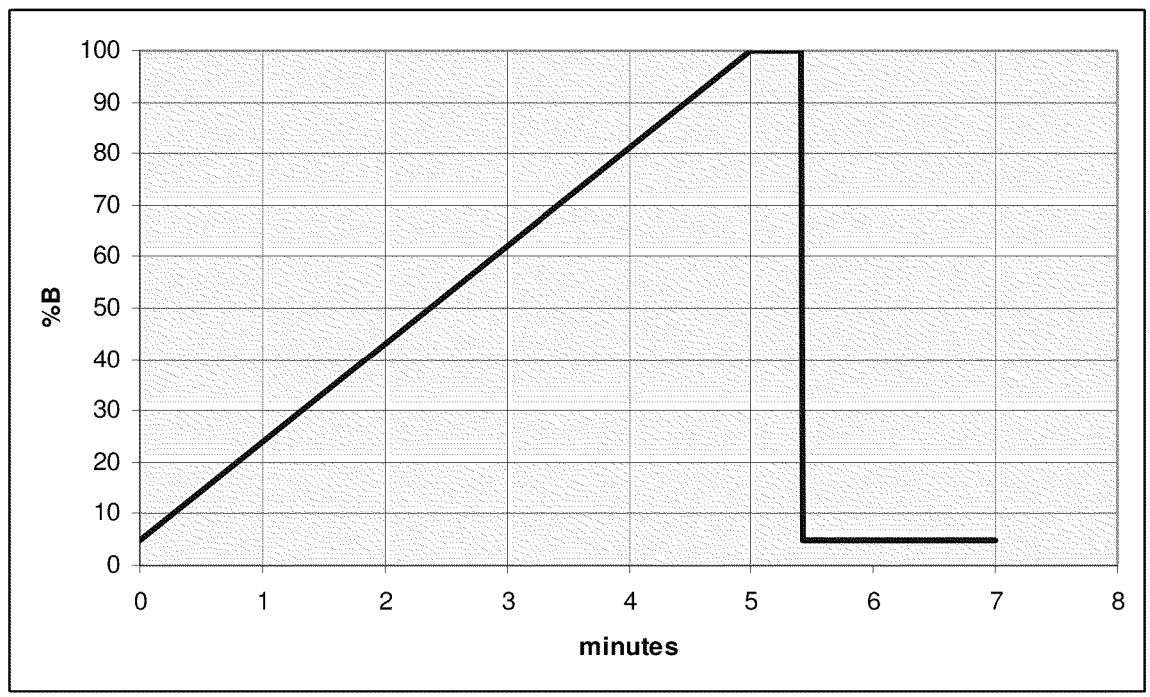
FIG. 1: Flow rate graph time vs % organic (B) using evaporative light scattering detectors.

In the broadest generic embodiment 1, the invention provides compounds of the formula

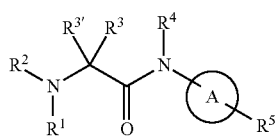

(I)

wherein:

ring A is a 5-membered heteroaryl ring;

$R^1$ is hydrogen, $C_{1-10}$ alkyl or $C_{3-10}$ cycloalkyl which is optionally substituted with 1-3 $C_{1-10}$ alkyl, each $R^1$ or it's substituent is optionally halogenated;

$R^2$ is $C_{1-10}$ alkyl, $C_{3-10}$ cycloalkyl, arylsulfonyl, arylcarbonyl, $C_{1-10}$ acyl, $C_{3-10}$ cycloalkylcarbonyl, heterocyclylcarbonyl, heteroarylcarbonyl, heterocyclyl, benzyl, phenethyl, aryl or heteroaryl each optionally independently substituted with 1 to 3 substituents chosen from $C_{1-6}$ alkyl, $C_{3-10}$ cycloalkyl, $C_{1-6}$ alkoxy, $C_{1-6}$ alkylthio, $C_{1-6}$ alkylsulfonyl, $C_{1-6}$ alkoxycarbonyl, $C_{1-6}$ alkylamino, $C_{3-6}$ cycloalkylamino, $C_{1-6}$ dialkylamino, $C_{1-6}$ alkylaminocarbonyl, $C_{1-6}$ acylamino, $C_{1-6}$ dialkylaminocarbonyl, hydroxyl, halogen, cyano, nitro, oxo, heterocyclyl, aryl and heteroaryl, each substituent on $R^2$ where possible is optionally halogenated or substituted with 1 to 3 $C_{1-6}$ alkyl, $C_{1-6}$ acyl, $C_{1-6}$ alkyl sulfonyl, cyano, aryl, oxo or hydroxyl;

or $R^1$ and $R^2$ together with the nitrogen atom to which they are attached form a monocyclic, bicyclic or spirocyclic heterocycle or monocyclic or bicyclic heteroaryl ring each optionally substituted with 1 to 3 $C_{1-6}$ alkyl, $C_{1-6}$ alkoxy, $C_{1-6}$ acyl, $C_{1-6}$ alkyl sulfonyl, cyano, aryl, oxo, hydroxyl or halogen each ring substituent being further optionally halogenated where possible;

$R^3$ and $R^{3'}$ are independently hydrogen or $C_{1-6}$ alkyl optionally halogenated with the proviso that $R^3$ and $R^{3'}$ cannot simultaneously be hydrogen; or $R^3$ and $R^{3'}$ together with the carbon atom to which they are attached form a 3- to 6-membered cycloalkyl or heterocyclic ring each optionally halogenated;

$R^4$ is hydrogen or methyl;

$R^5$ is chosen from

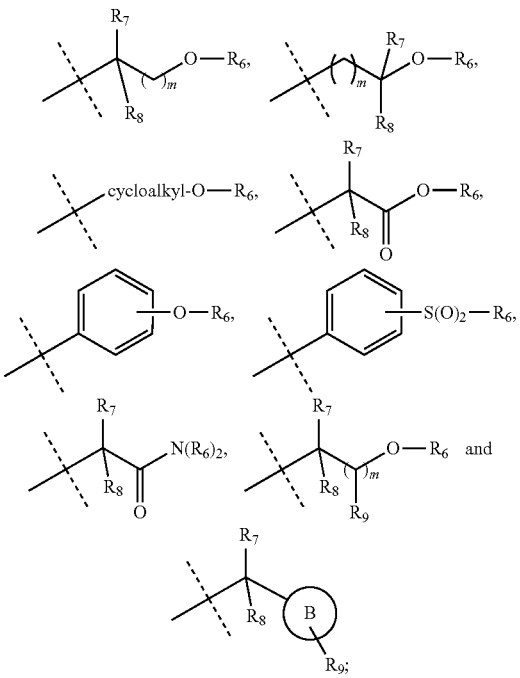

m is 0, 1, 2 or 3

$R^6$ is hydrogen, $C_{1-4}$ alkyl or $C_{1-4}$ alkoxy $R^7$ and $R^8$ are each independently hydrogen, or $C_{1-4}$ alkyl with the proviso that both $R^7$ and $R^8$ cannot be hydrogen; and wherein $R^7$ and $R^8$ optionally can cyclize to form a $C_{3-7}$ cycloalkyl ring;

$R^9$ is $C_{1-6}$ alkyl or aryl;

ring B is a 5-6 membered heterocyclic ring;

n is 0, 1 or 2;

wherein any carbon atom on the formula (I) or any R substituent listed above is optionally partially or fully halogenated where possible;

or a pharmaceutically acceptable salt thereof.

In another embodiment 2, the invention provides compounds of the formula (I) according to the embodiment immediately above, and wherein
ring A is

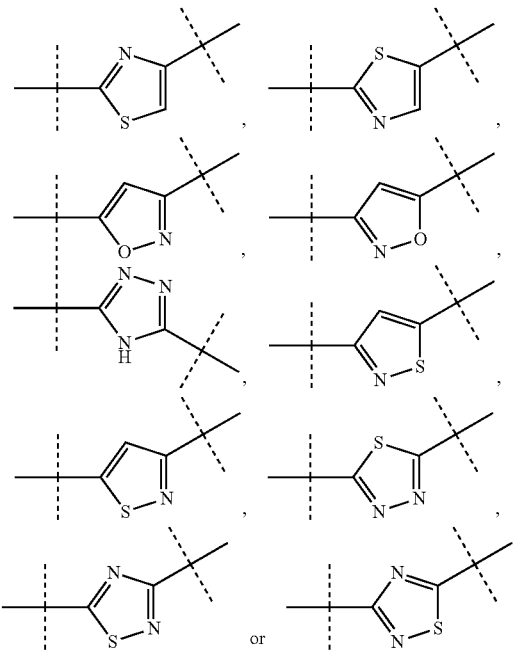

R² is C₁₋₆ alkyl, C₃₋₇ cycloalkyl, 1,1-dioxo-1λ⁶-thiomorpholinylcarbonyl, phenylsulfonyl, tetrahydropyranyl, tetrahydrofuranyl, pyrrolidinyl or piperidinyl, each optionally independently substituted with 1 to 3 substituents chosen from C₁₋₅ alkyl, C₃₋₇ cycloalkyl, C₁₋₅ alkoxy, C₁₋₅ alkylthio, C₁₋₅ alkylsulfonyl, C₁₋₅ alkoxycarbonyl, C₁₋₅ alkylamino, C₃₋₆ cycloalkylamino, C₁₋₅ dialkylamino, C₁₋₅ alkylaminocarbonyl, C₁₋₅ acylamino, C₁₋₅ dialkylaminocarbonyl, hydroxyl, halogen, cyano, nitro, oxo, phenyl and heterocyclyl chosen from tetrahydropyranyl, dioxanyl, tetrahydrofuranyl, thiomorpholinyl, 1,1-dioxo-1λ⁶-thiomorpholinyl, morpholinyl, pyrrolidinyl, piperidinyl and piperazinyl, each R² substituent where possible is optionally halogenated or substituted with 1 to 3 C₁₋₅ alkyl, C₁₋₅ acyl, methyl sulfonyl, cyano, phenyl, oxo or hydroxyl;

or R¹ and R² together with the nitrogen atom to which they are attached form a ring chosen from thiomorpholinyl, 1,1-dioxo-1λ⁶-thiomorpholinyl, morpholinyl, pyrrolidinyl, piperidinyl, piperazinyl, azetidinyl, benzimidazolyl, pyrazolyl, imidazolyl, triazinyl, indazolyl, indolyl, indolinyl, isoindolyl, isoindolinyl, and 2-aza-spiro[4.5]dec-2-yl, 1-aza-spiro[4.5]dec-1-yl, 1-aza-spiro[4.4]non-1-yl, 2-aza-spiro[4.4]non-2-yl, 2-aza-spiro[5.5]undec-2-yl, 1-aza-spiro[5.5]undec-1-yl
each optionally substituted with 1 to 3 C₁₋₆ alkyl, C₁₋₆ alkoxy, C₁₋₆ acyl, C₁₋₆ alkyl sulfonyl, cyano, phenyl, oxo, hydroxyl and halogen each ring substituent being further optionally halogenated where possible;

R³ and R³' are each methyl or ethyl, each optionally halogenated, or R³ and R⁴ together with the carbon atom to which they are attached form a cyclopropyl or cyclobutyl ring each optionally halogenated.

In another embodiment 3, the invention provides compounds of the formula (I) according to the embodiment described immediately above, and wherein ring A is

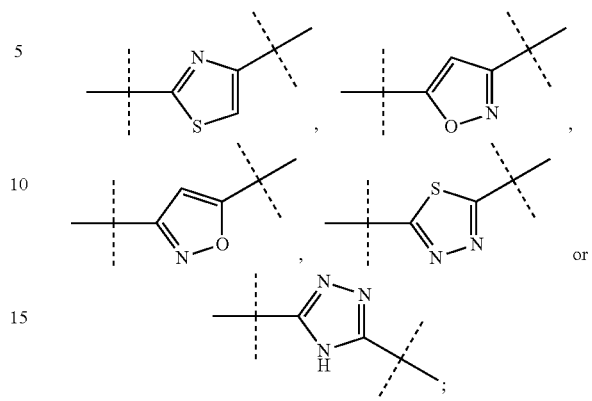

R¹ is hydrogen or C₁₋₃ alkyl optionally halogenated;
R² is C₁₋₆ alkyl or C₃₋₇ cycloalkyl optionally independently substituted with 1 to 3 halogen, one C₃₋₇ cycloalkyl, C₁₋₆ alkoxy or one heterocyclyl chosen from tetrahydropyranyl, dioxanyl, tetrahydrofuranyl, thiomorpholinyl, 1,1-dioxo-1λ⁶-thiomorpholinyl, morpholinyl, pyrrolidinyl, piperidinyl and piperazinyl each optionally halogenated or substituted with C₁₋₄ alkyl or methyl sulfonyl;

or R¹ and R² together with the nitrogen atom to which they are attached form a ring chosen form thiomorpholinyl, 1,1-dioxo-1λ⁶-thiomorpholinyl, morpholinyl, pyrrolidinyl, piperidinyl, azetidinyl, indolyl, indolinyl, isoindolyl, isoindolinyl, and 2-aza-spiro[4.5]dec-2-yl each optionally substituted with 1 to 3 C₁₋₄ alkyl, C₁₋₄ alkoxy and halogen each ring substituent being further optionally halogenated where possible;

R³ and R³' are each methyl or ethyl or R³ and R⁴ together with the carbon atom to which they are attached form a cyclopropyl or cyclobutyl ring;
R⁶ is hydrogen or C₁₋₂ alkyl;
R⁷ and R⁸ are each C₁₋₂ alkyl.

In another embodiment 4, the invention provides compounds of the formula (I) according to the embodiment immediately above, and wherein
ring A is

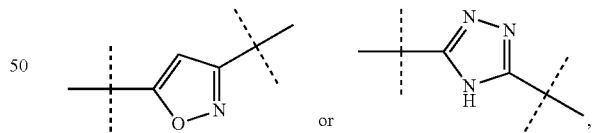

R² is methyl optionally substituted with one heterocyclyl chosen from tetrahydropyranyl, dioxanyl, tetrahydrofuranyl, thiomorpholinyl, 1,1-dioxo-1λ⁶-thiomorpholinyl, morpholinyl, pyrrolidinyl, piperidinyl and piperazinyl each optionally halogenated or substituted with C₁₋₄ alkyl or methyl sulfonyl;

or R¹ and R² together with the nitrogen atom to which they are attached form a ring chosen form thiomorpholinyl, 1,1-dioxo-1λ⁶-thiomorpholinyl, morpholinyl, pyrrolidinyl, piperidinyl, azetidinyl, indolyl and 2-aza-spiro[4.5]dec-2-yl each optionally substituted with 1 to 3 C₁₋₃ alkyl, C₁₋₃ alkoxy and halogen each ring substituent being further optionally halogenated where possible.

In another embodiment 5, the invention provides compounds of the formula (I) according to the embodiment 1, and wherein
ring A is

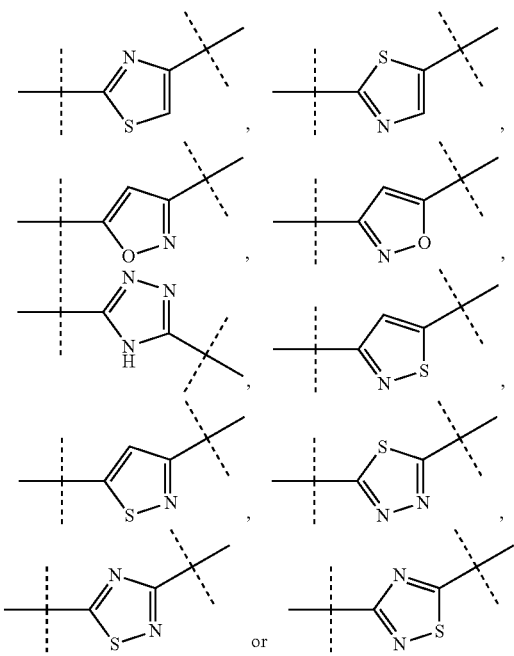

R¹ is hydrogen, $C_{1-6}$ alkyl or $C_{3-7}$ cycloalkyl optionally substituted with 1-3 $C_{1-6}$ alkyl, each R¹ or it's substituent is optionally halogenated;

R² is cyclopentyl, cyclohexyl, tetrahydropyranyl, tetrahydrofuranyl, thiomorpholinylcarbonyl, 1,1-dioxo-1λ⁶-thiomorpholinylcarbonyl, morpholinylcarbonyl, phenylsulfonyl, phenylcarbonyl, phenyl, pyridinyl, piperidinyl, pyrimidinyl or thiazolyl, each optionally independently substituted with 1 to 3 substituents chosen from $C_{1-5}$ alkyl, $C_{3-5}$ cycloalkyl, $C_{1-5}$ alkoxy, $C_{1-5}$ alkylthio, $C_{1-5}$ alkylsulfonyl, $C_{1-5}$ alkoxycarbonyl, $C_{1-5}$ alkylamino, $C_{3-6}$ cycloalkylamino, $C_{1-5}$ dialkylamino, $C_{1-5}$ alkylaminocarbonyl, $C_{1-5}$ acylamino, $C_{1-5}$ dialkylaminocarbonyl, hydroxyl, halogen, cyano and nitro, each R² substituent where possible is optionally halogenated or substituted with 1 to 3 $C_{1-5}$ alkyl or $C_{1-5}$ alkyl sulfonyl, or R¹ and R² together with the nitrogen atom to which they are attached form a ring chosen from tetrahydropyranyl, dioxanyl, tetrahydrofuranyl, thiomorpholinyl, 1,1-dioxo-1λ⁶-thiomorpholinyl, morpholinyl, pyrrolidinyl, piperidinyl, piperazinyl, azetidinyl, benzimidazolyl, pyrazolyl, imidazolyl, triazinyl, indazolyl, indolyl, indolinyl, isoindolyl, isoindolinyl, and 2-aza-spiro[4.5]dec-2-yl, 1-aza-spiro[4.5]dec-1-yl, 1-aza-spiro[4.4]non-1-yl, 2-aza-spiro[4.4]non-2-yl, 2-aza-spiro[5.5]undec-2-yl, 1-aza-spiro[5.5]undec-1-yl each optionally substituted with 1 to 3 $C_{1-6}$ alkyl, $C_{1-6}$ alkoxy, $C_{1-6}$ acyl, $C_{1-6}$ alkyl sulfonyl, cyano, phenyl, oxo, hydroxyl or halogen each ring substituent being further optionally halogenated where possible;

R³ and R³' are each methyl optionally halogenated, or R³ and R³' together with the carbon atom to which they are attached form a cyclopropyl or cyclobutyl ring each optionally halogenated;

R⁴ is hydrogen;

R⁵ is chosen from

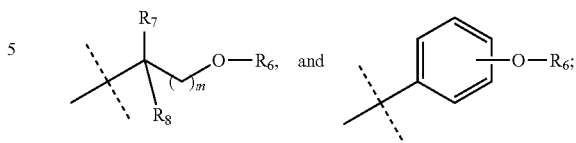

R⁶ is hydrogen or $C_{1-3}$ alkyl;

wherein R⁷ and R⁸ are each $C_{1-3}$ alkyl or $C_{3-6}$ cycloalkyl.

In another embodiment 6, the invention provides compounds of the formula (I) according to the embodiment 3, and wherein
ring A is

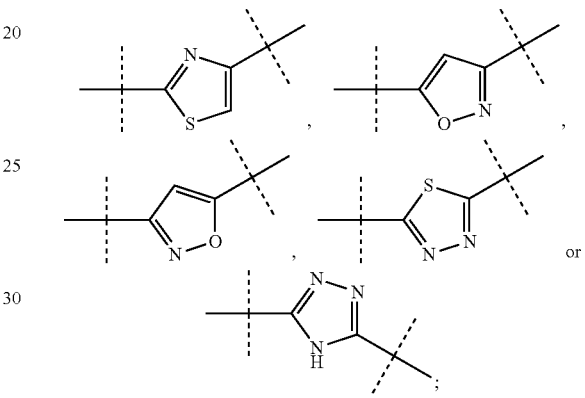

R³ and R³' are methyl;

R⁶ is hydrogen or $C_{1-2}$ alkyl;

wherein R⁷ and R⁸ are each $C_{1-2}$ alkyl.

In another embodiment 7, the invention provides compounds of the formula (I) according to the embodiment 6, and wherein
ring A is

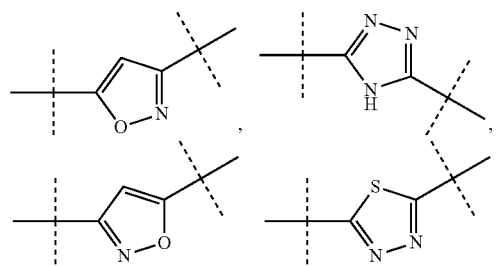

R¹ and R² together with the nitrogen atom to which they are attached form a ring chosen from thiomorpholinyl, 1,1-dioxo-1λ⁶-thiomorpholinyl, morpholinyl, pyrrolidinyl, piperidinyl, azetidinyl, indolyl and 2-aza-spiro[4.5]dec-2-yl each optionally substituted with 1 to 3 $C_{1-3}$ alkyl, $C_{1-3}$ alkoxy, hydroxy and halogen each ring substituent being further optionally halogenated where possible.

In another embodiment 8, the invention provides compounds of the formula (I) according to the embodiment described immediately above, and wherein ring A is

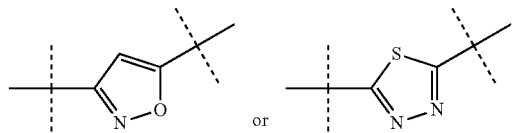

In another embodiment 9, the invention provides compounds of the formula (I) according to the embodiment described immediately above, and wherein $R^1$ and $R^2$ together with the nitrogen atom to which they are attached form a ring chosen from morpholinyl, pyrrolidinyl and piperidinyl, each optionally substituted with 1 to 3 $C_{1-3}$ alkyl.

In another embodiment 10, the invention provides compounds of the formula (I) according to embodiment 2, and wherein $R^2$ is cyclopropyl, cyclohexyl, tetrahydropyranyl, pyrrolidinyl or piperidinyl, each optionally independently substituted with 1 to 2 substituents chosen from $C_{1-3}$ alkyl and $C_{1-2}$ alkylsulfonyl.

In another embodiment 11, the invention provides compounds of the formula (I) according to embodiment 2, and wherein $R^2$ is $CF_3$—$CH_2$—$CH_2$—$CH_2$—, $CH_3$—$CH_2$—$CH_2$($CH_3$)—, cyclopropyl-$CH_2$—, hydroxylcyclohexyl, tetrahydrofuranyl-$CH_2$—;

ring A is

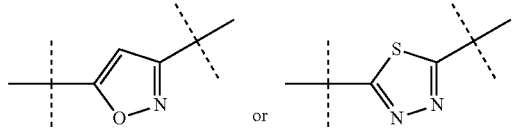

$R^5$ is

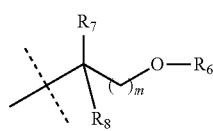

wherein wherein $R^7$ and $R^8$ optionally can cyclize to form a $C_{3-7}$ cycloalkyl ring.

In another embodiment 12, the invention provides compounds of the formula (I) according to embodiment 2, and wherein $R^2$ hydroxylcyclohexyl, tetrahydropyranyl, hydroxylpyrrolidinyl or methylsulfonylpyrrolidinyl;

ring A is

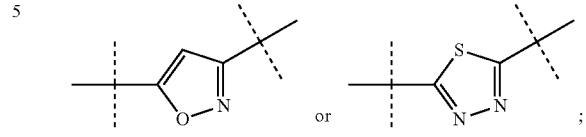

$R^5$ is

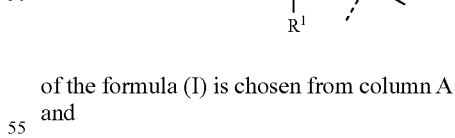

wherein wherein $R^7$ and $R^8$ optionally can cyclize to form a $C_{3-7}$ cycloalkyl ring;

$R^1$ and $R^2$ optionally can cyclize to form piperidinyl, methylsulfonylpiperidinyl.

In another aspect of the invention there is provided a second set of generic embodiments, wherein for each of the above embodiments 1-10 of the formula (I), $R^7$ and $R^6$ can cyclize to form a 4-6 membered heterocyclic ring.

In another embodiment there is provided a compound of the formula (II)

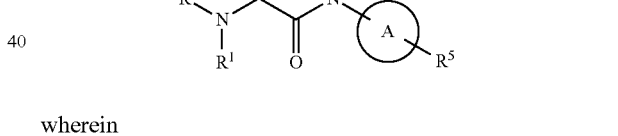

wherein

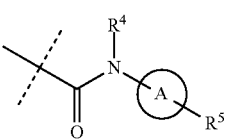

of the formula (I) is chosen from column A1-A42 in Table I, and

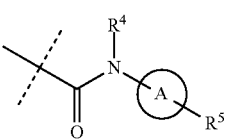

of the formula (I) is chosen from column B1-B22 in Table I, with the proviso that when column B is B3, B13 or B22, then A must be A20, A23, A38, or A42

TABLE I
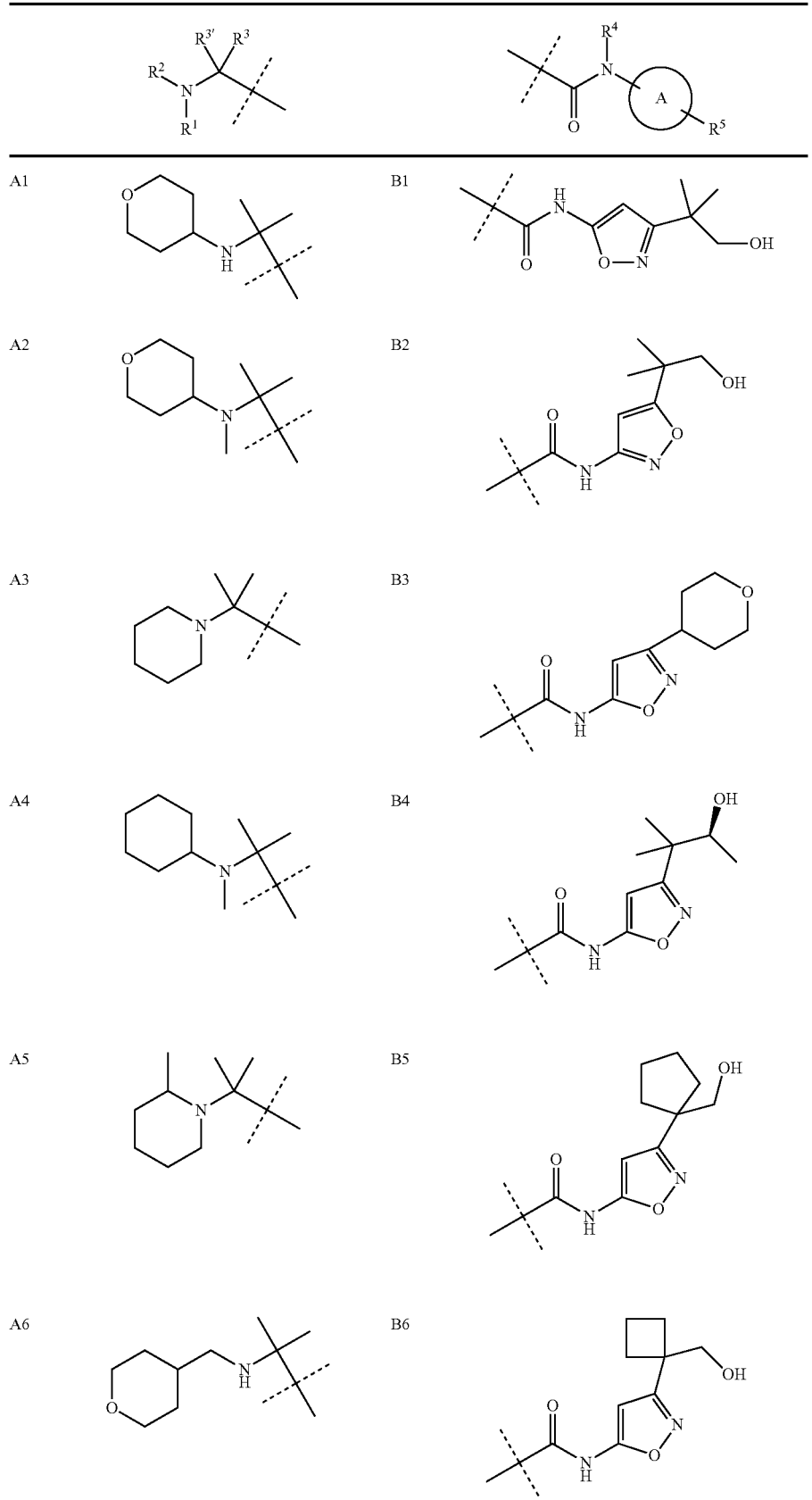

TABLE I-continued
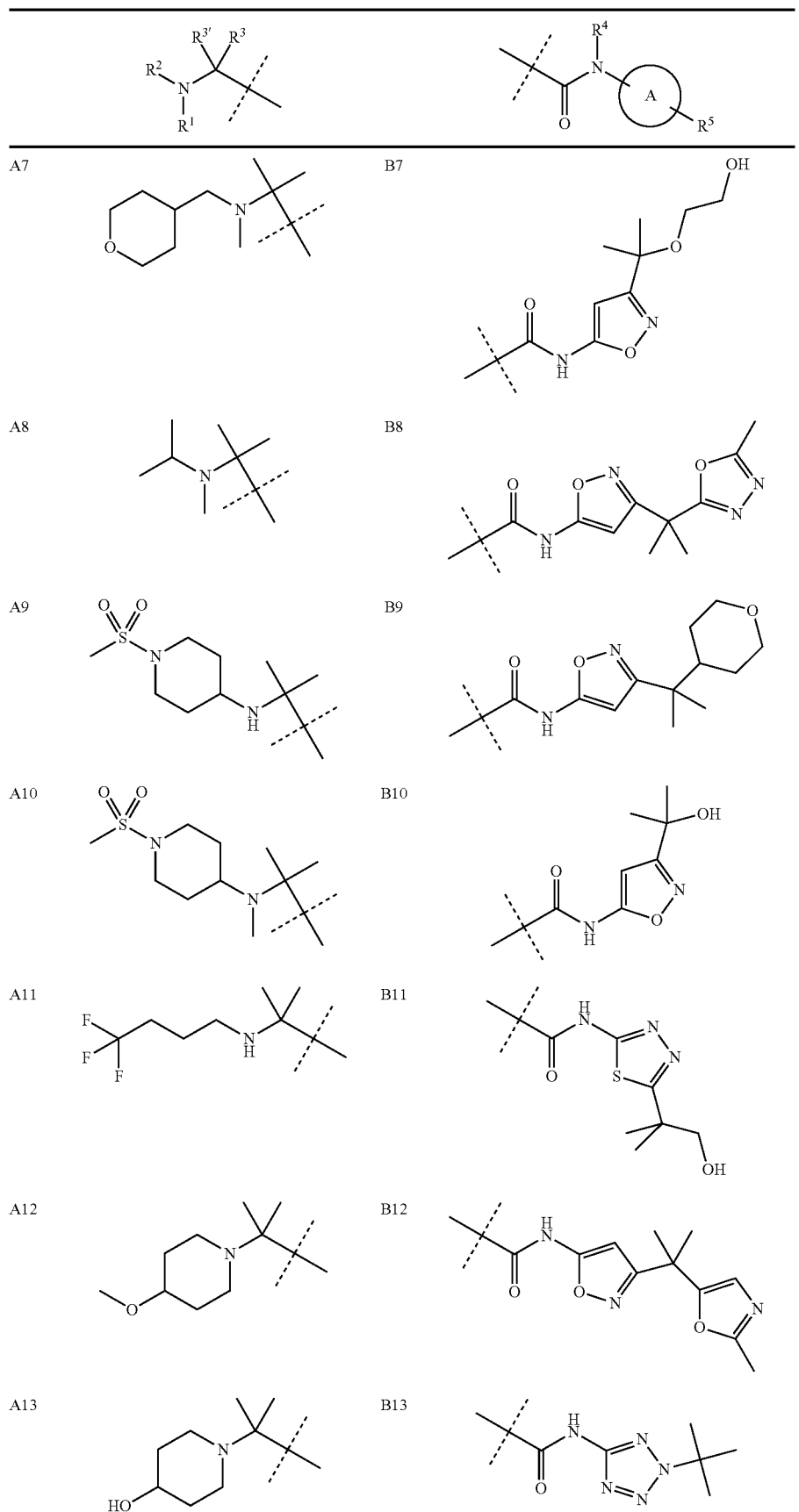

TABLE I-continued
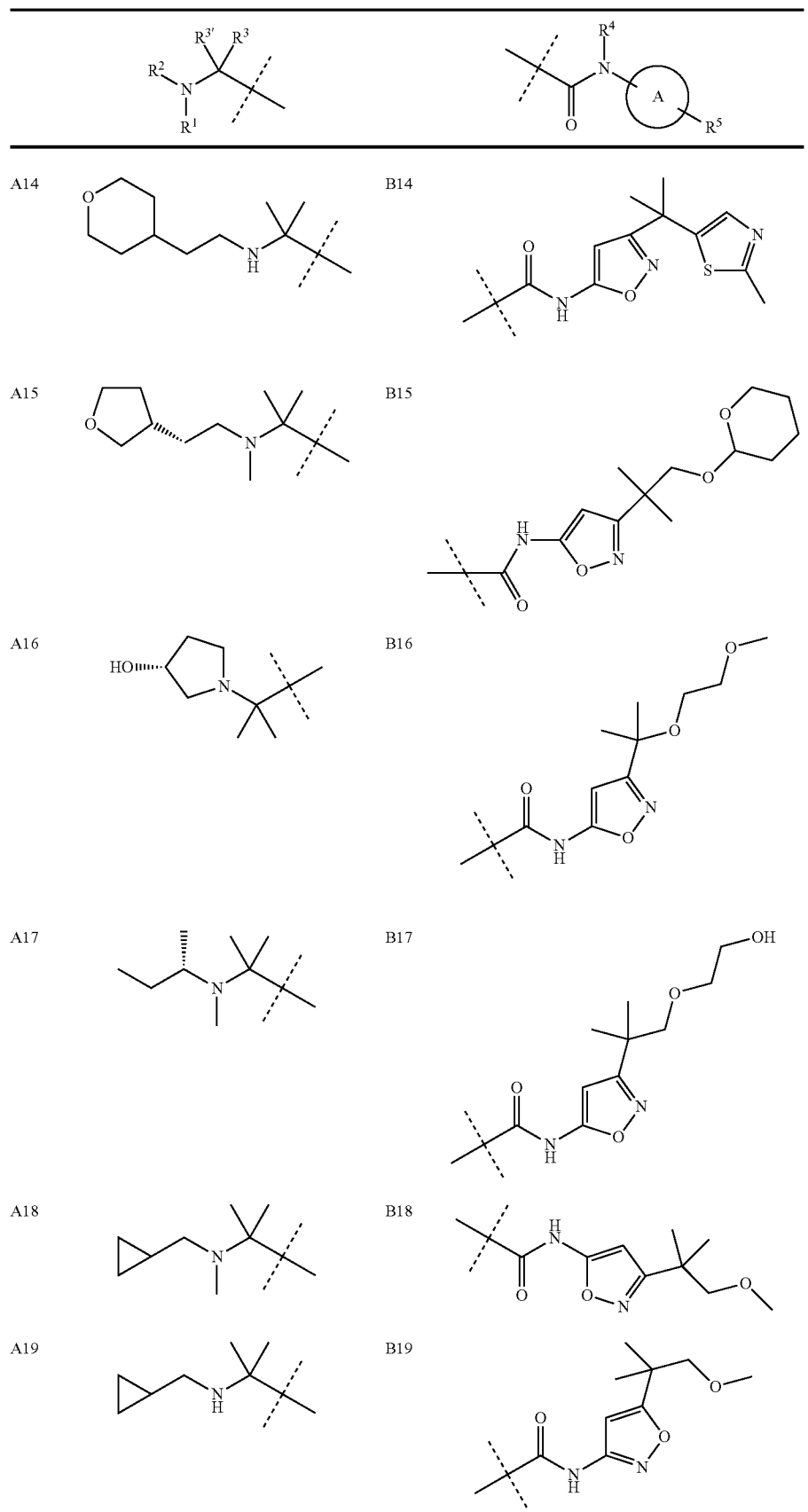

TABLE I-continued
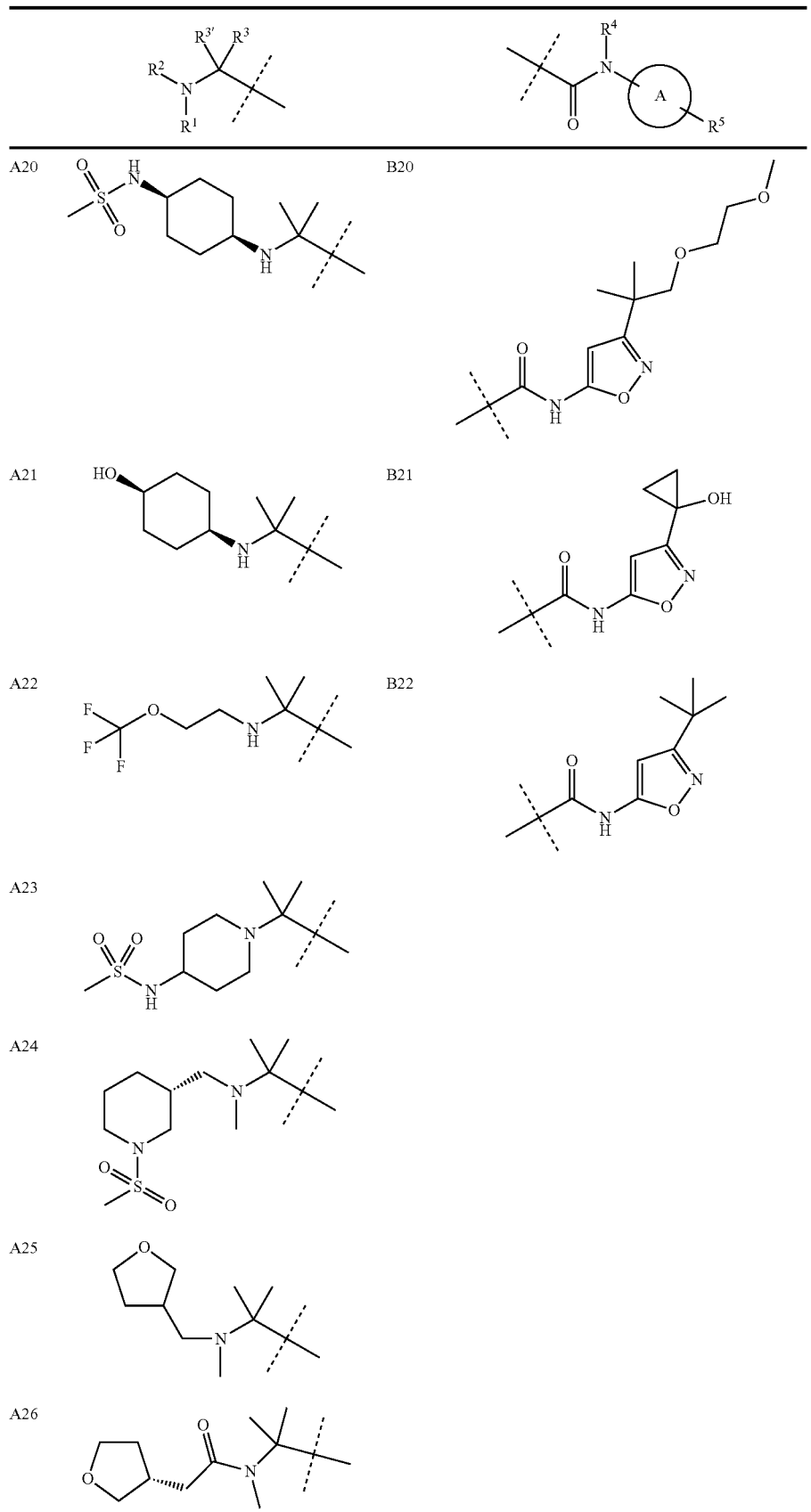

TABLE I-continued
| | 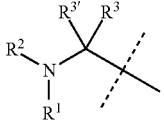 | 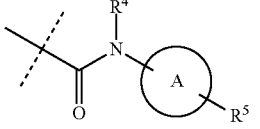 |
|---|---|---|
| A27 | 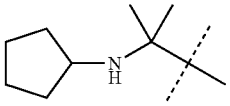 | |
| A28 | 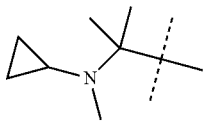 | |
| A29 | 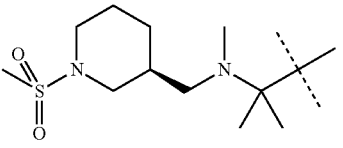 | |
| A30 | 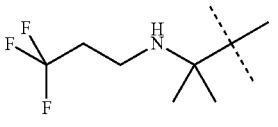 | |
| A31 | 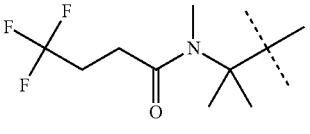 | |
| A32 | 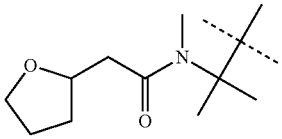 | |
| A33 | 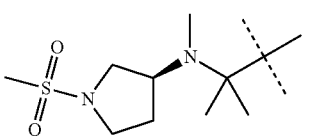 | |
| A34 | 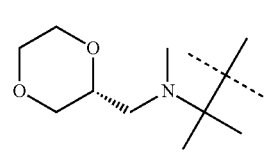 | |
| A35 | 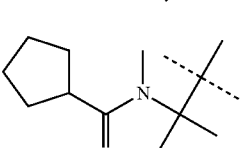 | |
| A36 | 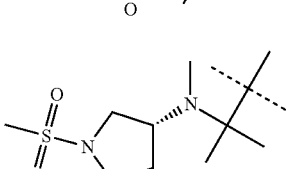 | |

TABLE I-continued
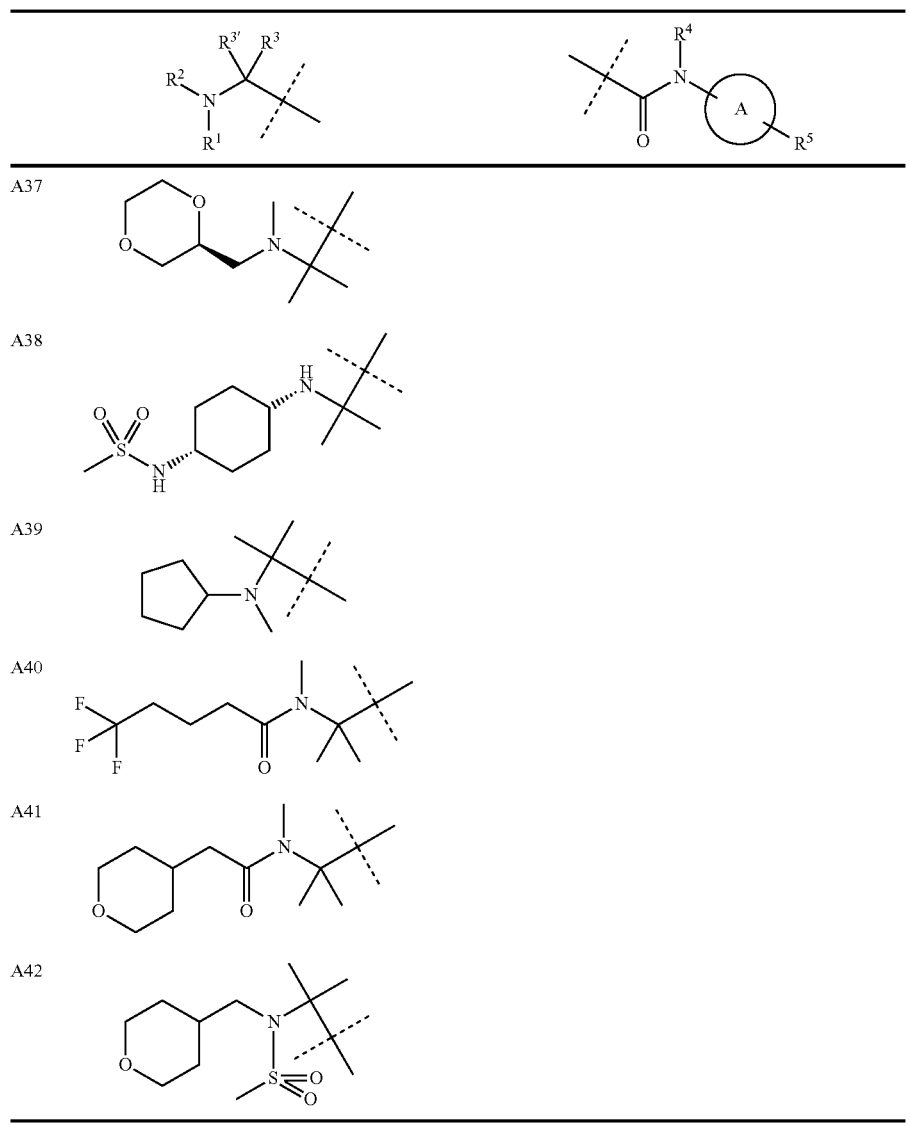
In another embodiment, the invention provides made compounds in Table II which can be made in view of the general schemes, examples and methods known in the art.
TABLE II
TABLE II-continued
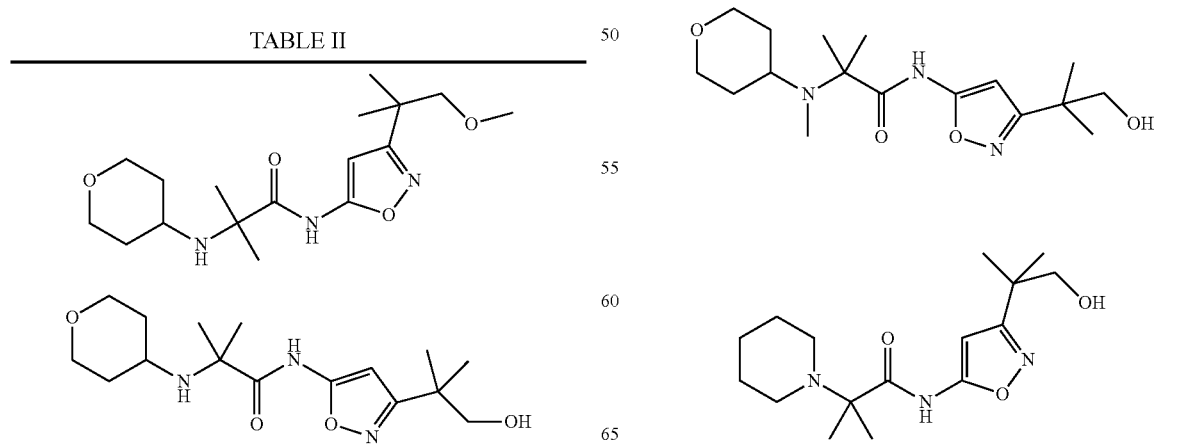

TABLE II-continued
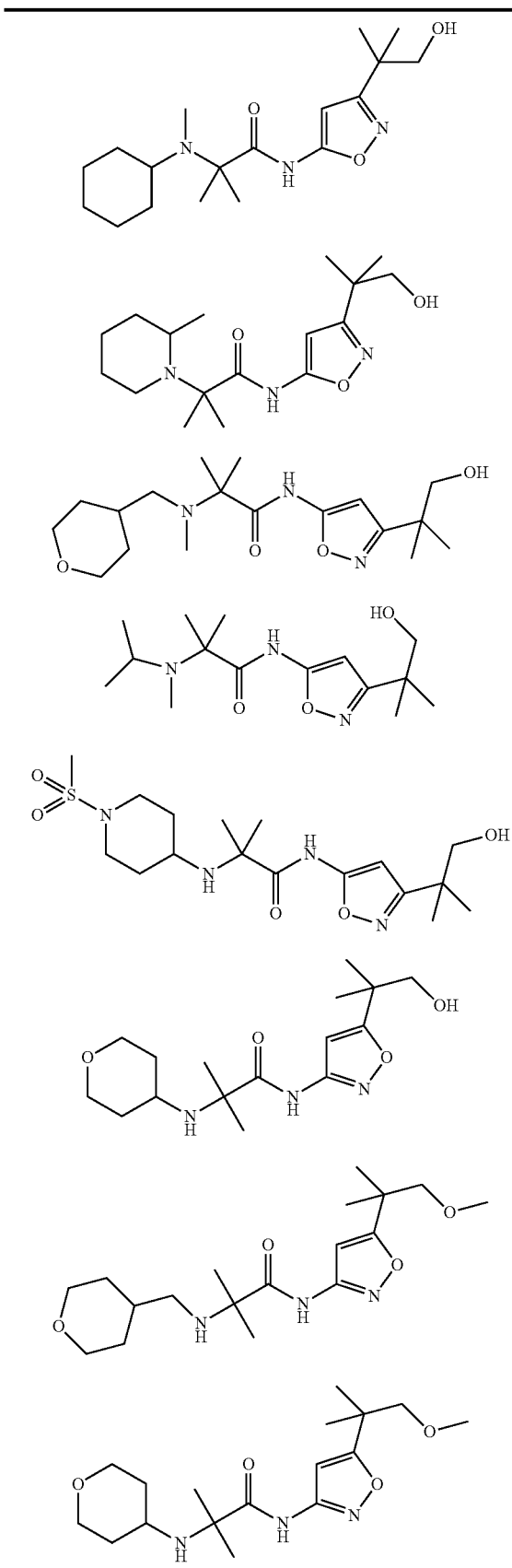
TABLE II-continued
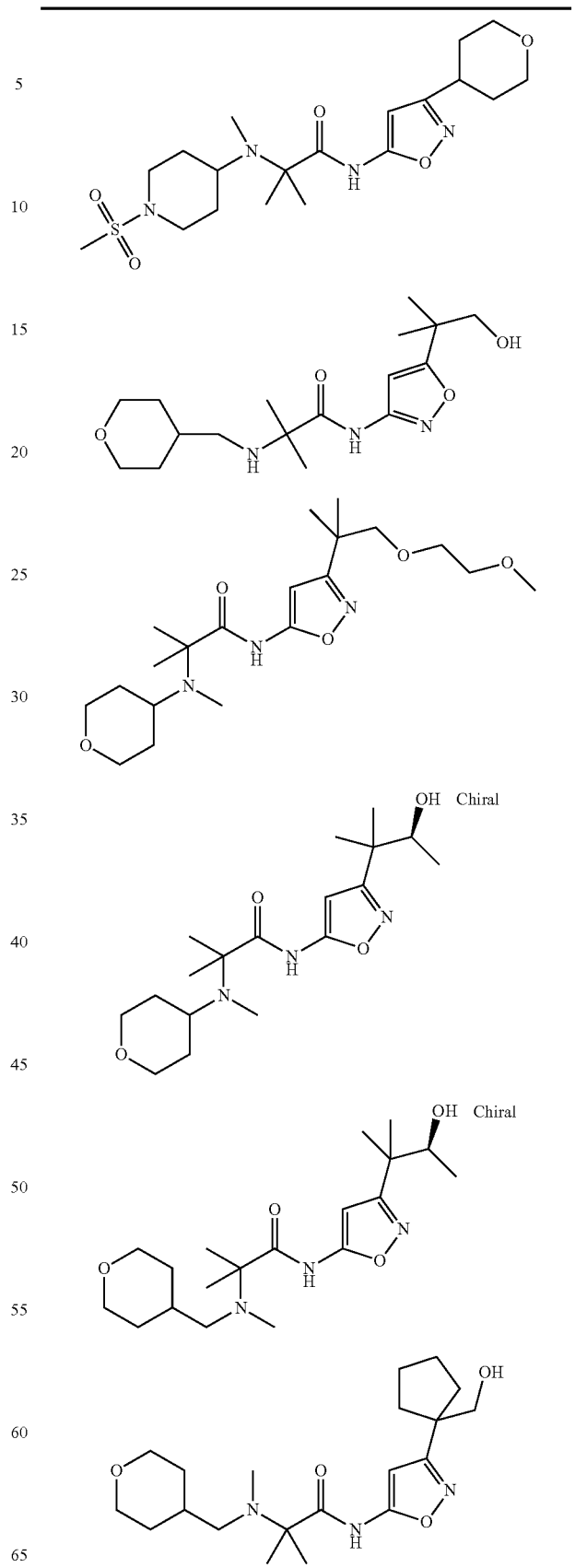

TABLE II-continued
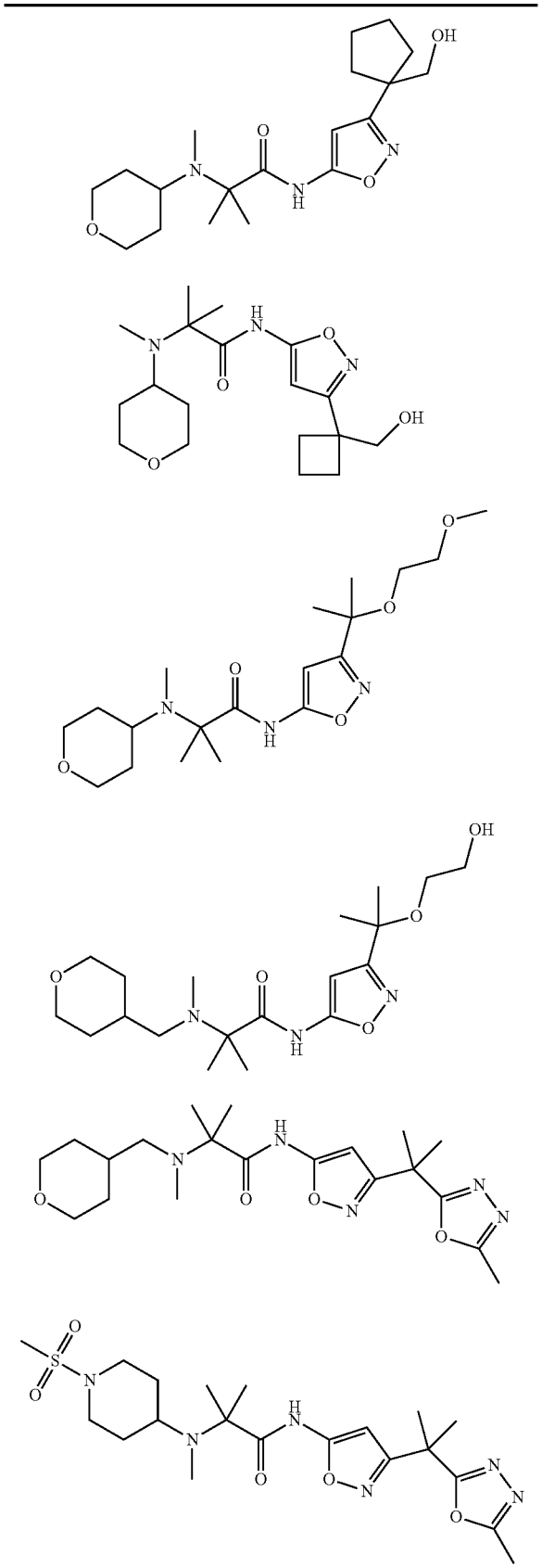
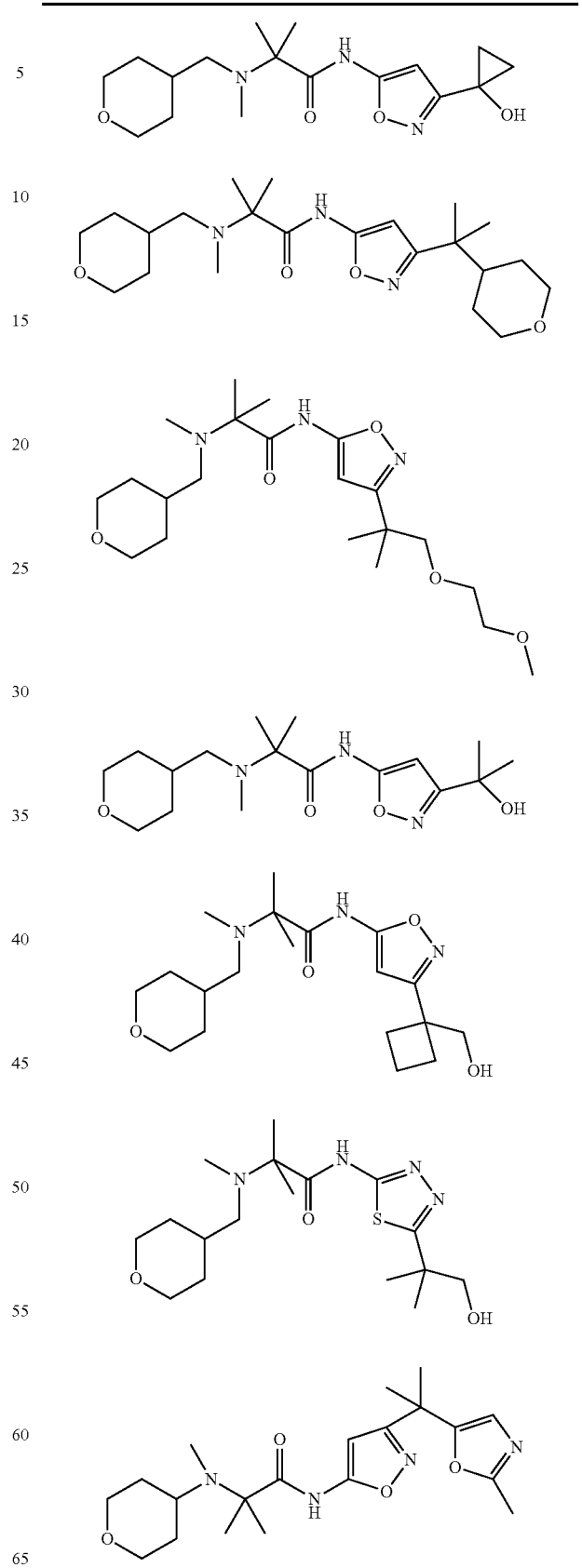

TABLE II-continued
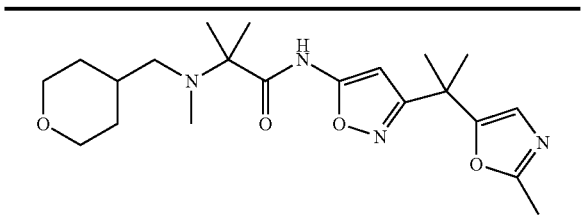
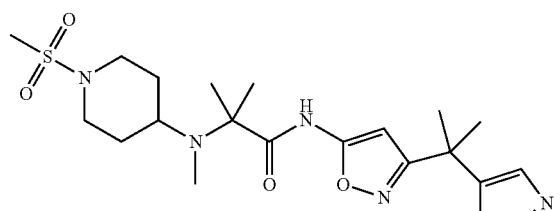
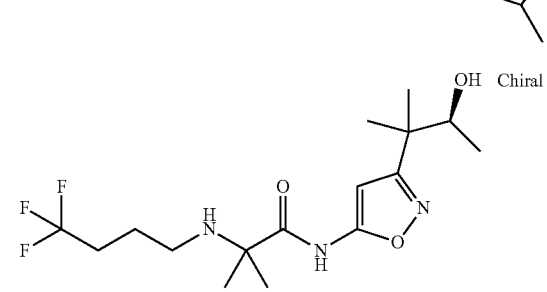
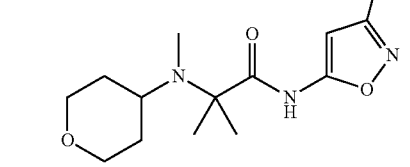
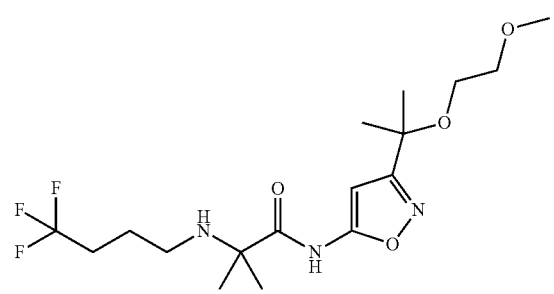
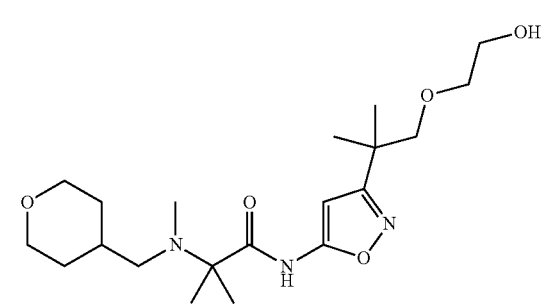
TABLE II-continued
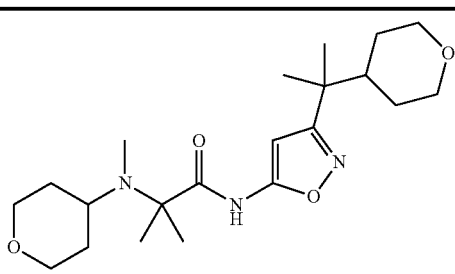
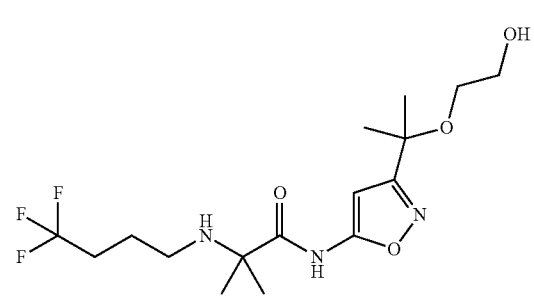
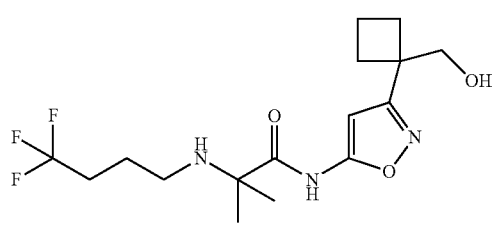
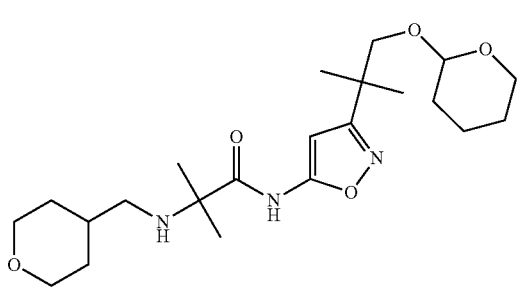
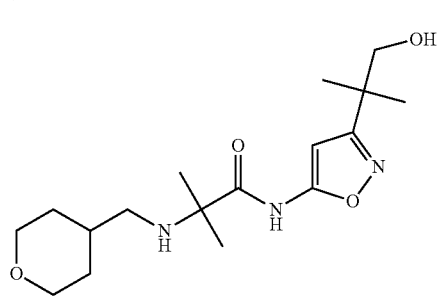
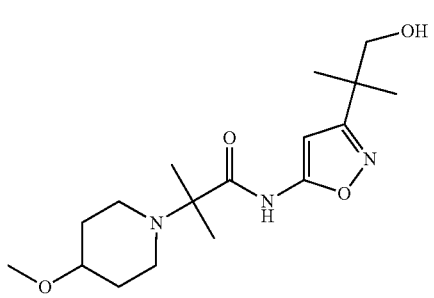

TABLE II-continued
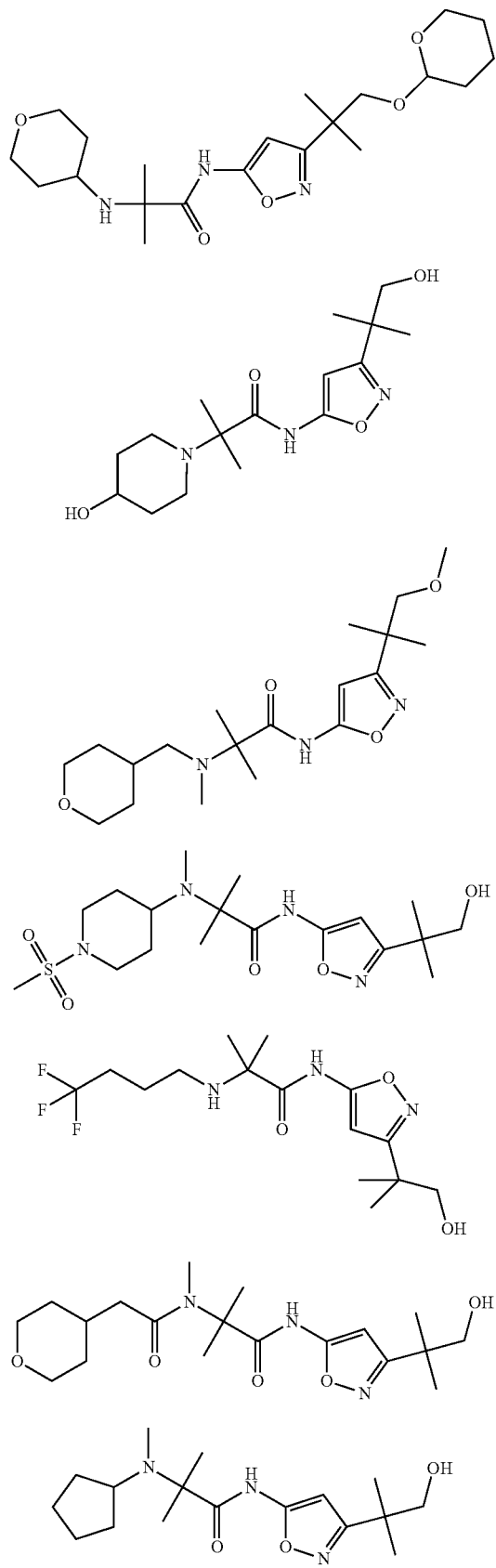
TABLE II-continued
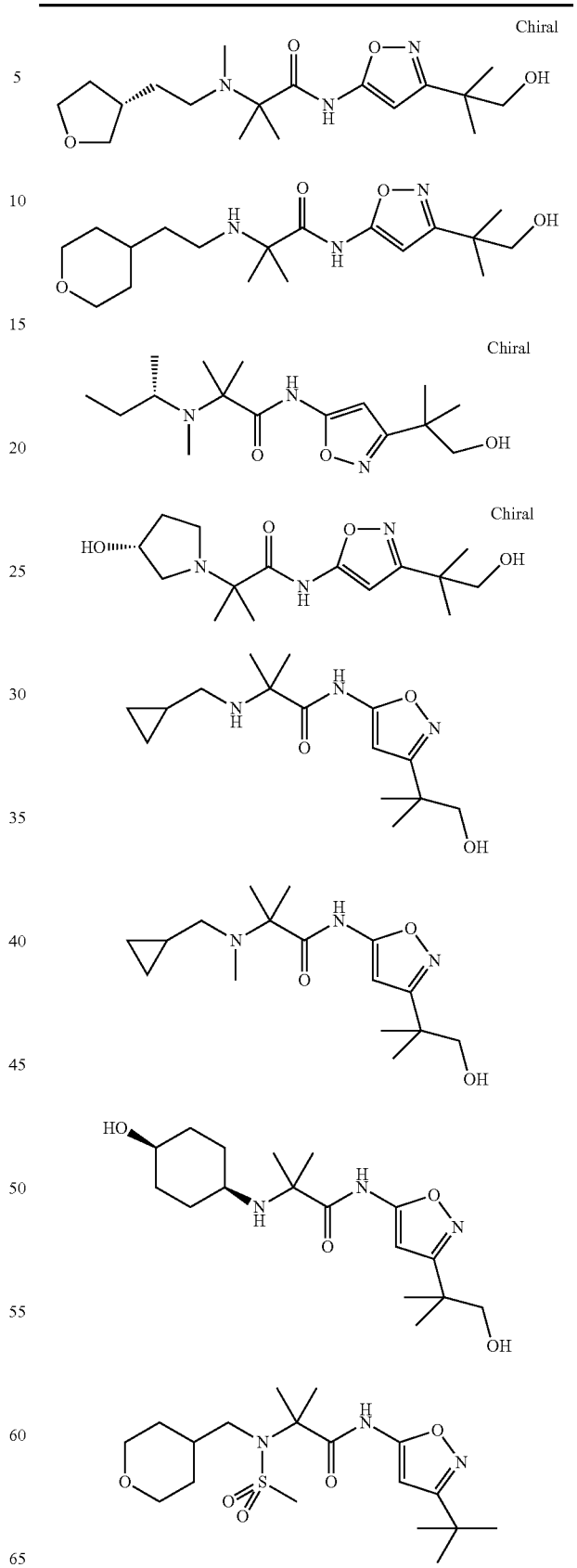

TABLE II-continued
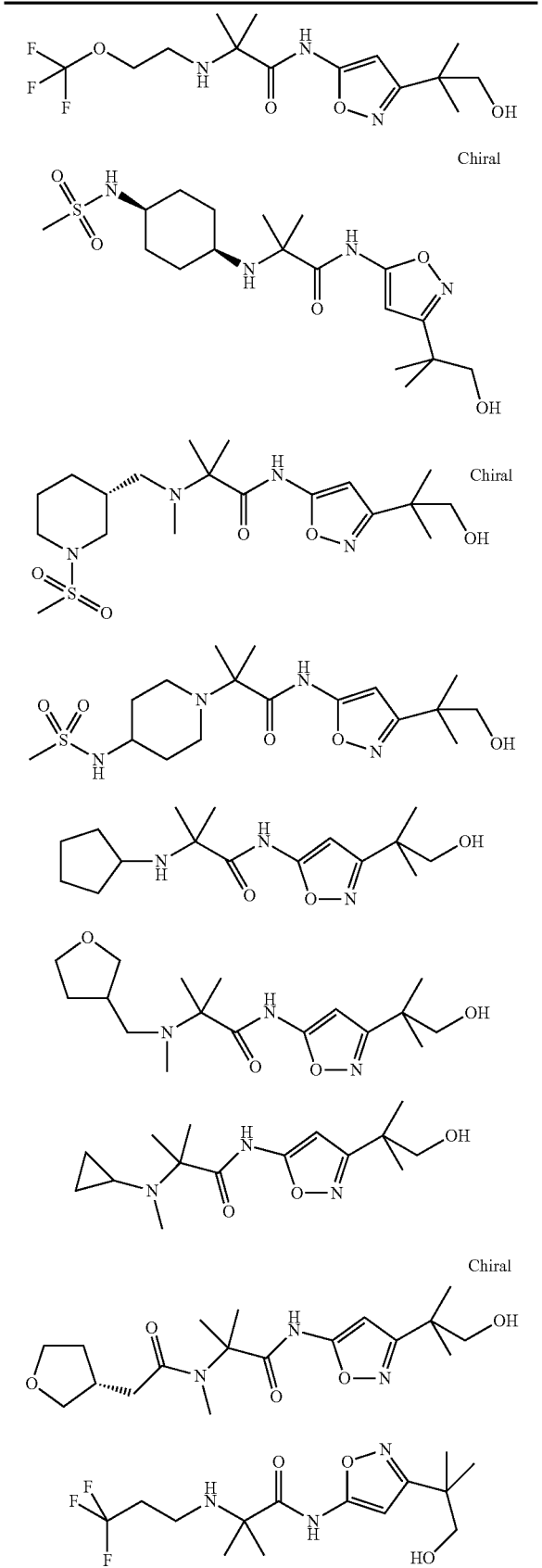
TABLE II-continued
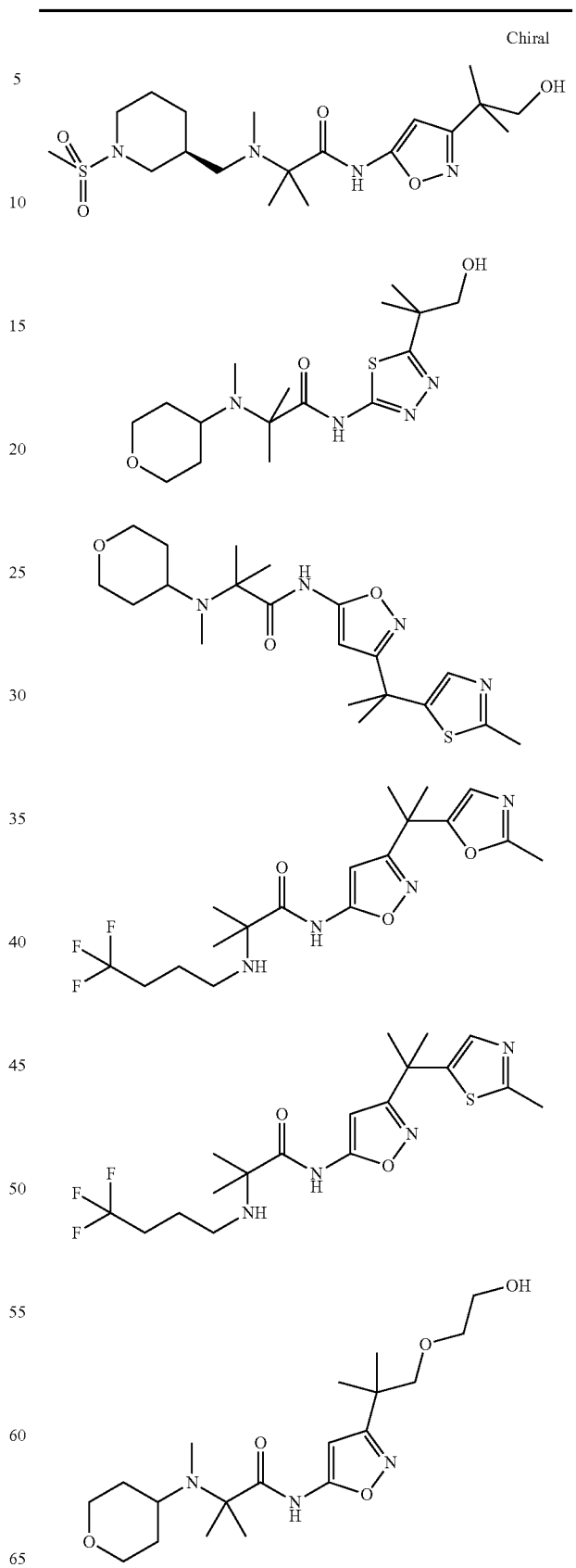

TABLE II-continued
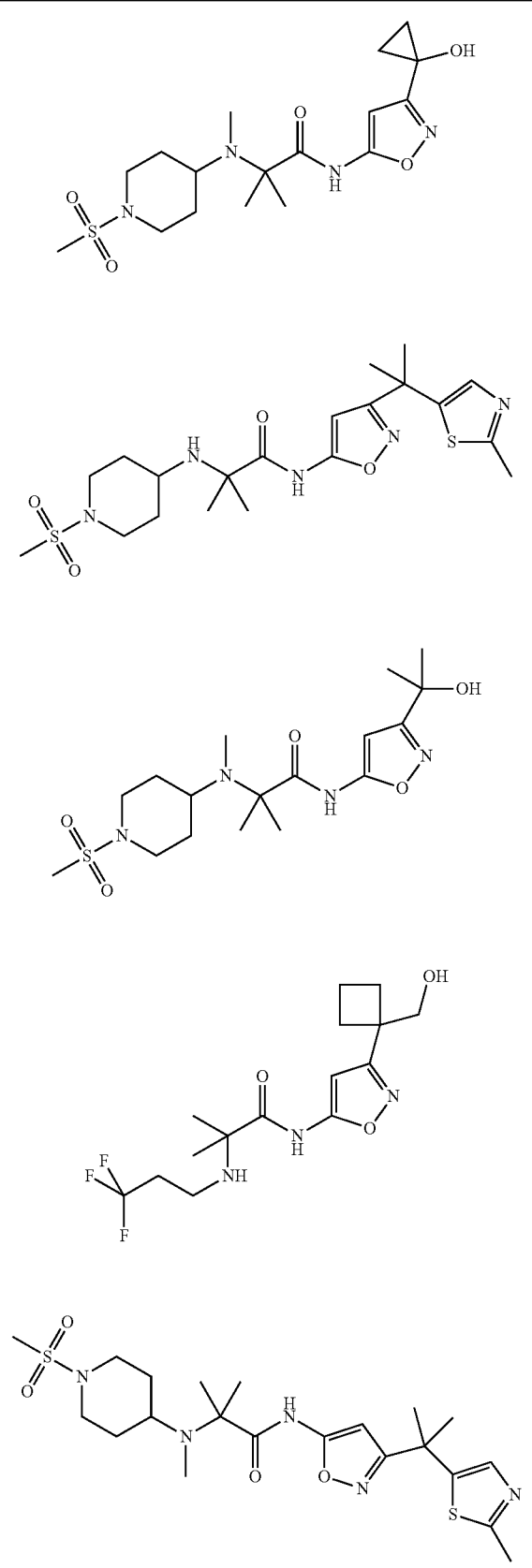
TABLE II-continued
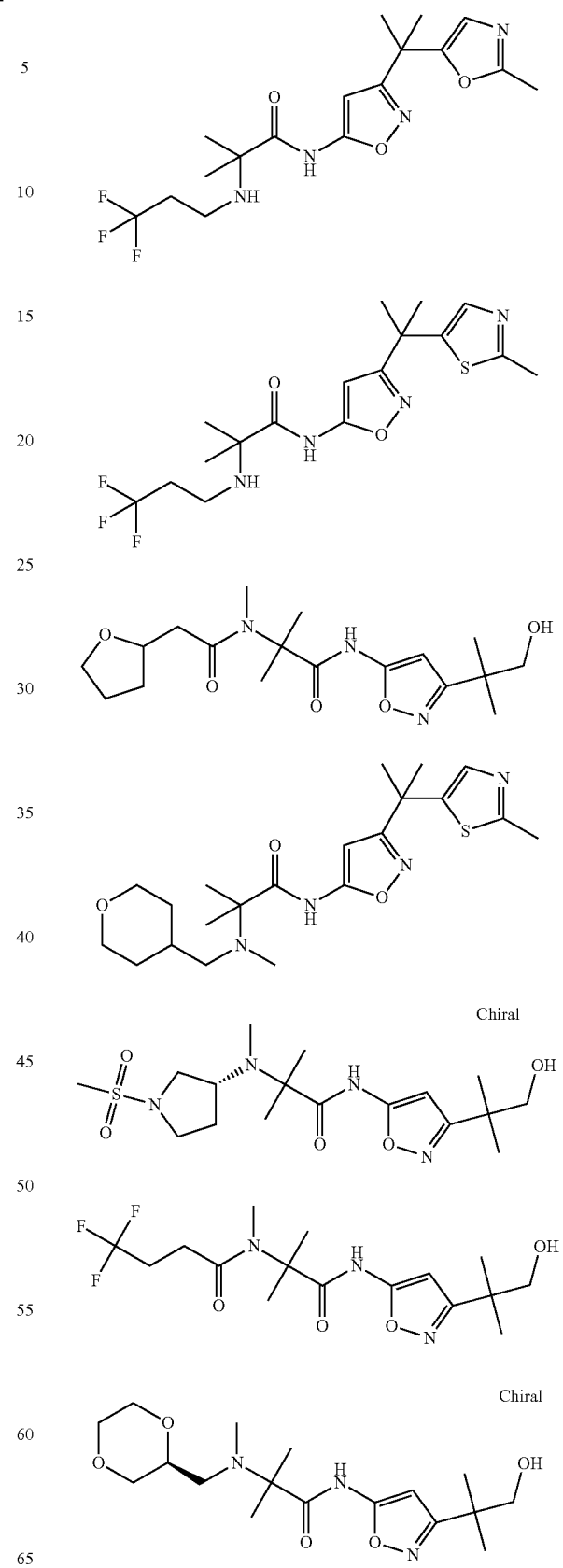

TABLE II-continued
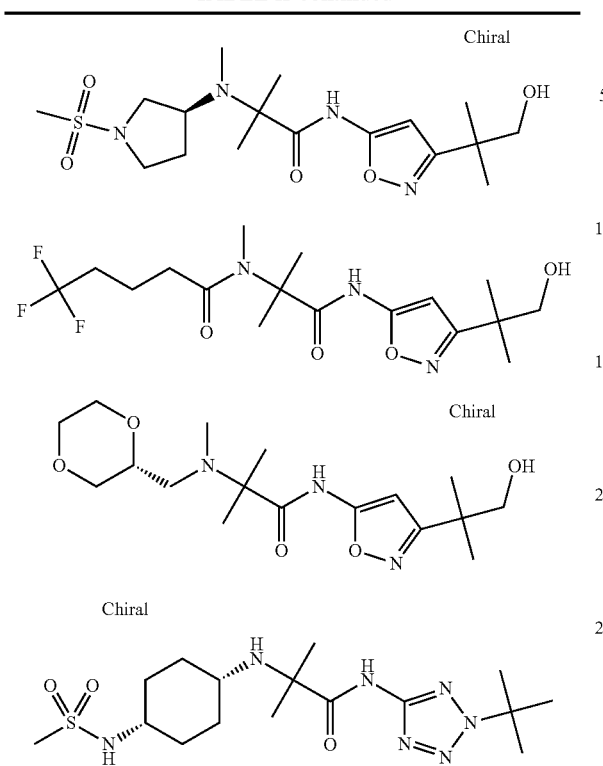
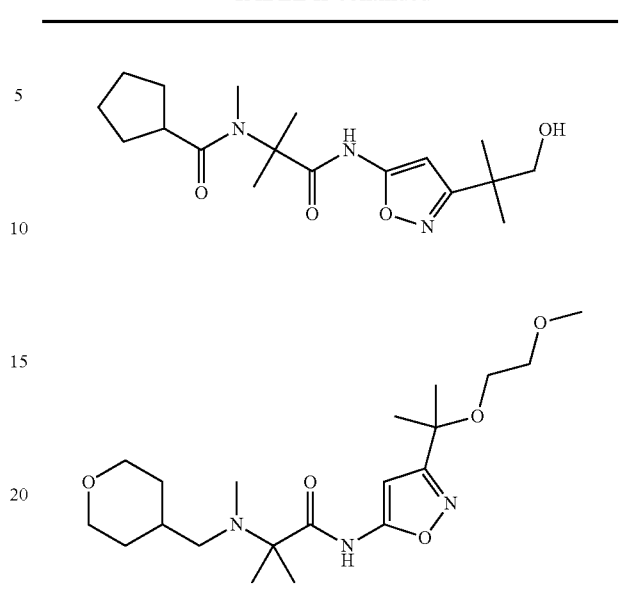
or a pharmaceutically acceptable salt thereof.
Of the above compounds, the following are preferred CB2 agonists:
TABLE III
| Compound | CB2 EC$_{50}$ (nM) | CB1 EC$_{50}$ (nM) |
|---|---|---|
|  | 313 | >20000 |
|  | 56 | >50000 |
|  | 28 | 22037 |
|  | 244 | >50000 |

TABLE III-continued

| Compound | CB2 EC$_{50}$ (nM) | CB1 EC$_{50}$ (nM) |
|---|---|---|
| (structure) | 302 | >50000 |
| (structure) | 132 | >20000 |
| (structure) | 337 | >20000 |
| (structure) | 246 | >50000 |
| (structure, Chiral) | 28 | 44747 |
| (structure) | 21 | 21534 |

TABLE III-continued

| Compound | CB2 EC$_{50}$ (nM) | CB1 EC$_{50}$ (nM) |
|---|---|---|
| | 66 | >50000 |
| | 93 | >50000 |
| | 13 | >50000 |
| | 11 | >50000 |
| | 15 | 20819 |
| | 44 | >50000 |

TABLE III-continued

| Compound | CB2 EC$_{50}$ (nM) | CB1 EC$_{50}$ (nM) |
|---|---|---|
| (structure) | 109 | >50000 |
| (structure) | 54 | >50000 |
| (structure) | 201 | >50000 |
| (structure) | 374 | >50000 |
| (structure) | 31 | >50000 |

TABLE III-continued

| Compound | CB2 EC$_{50}$ (nM) | CB1 EC$_{50}$ (nM) |
|---|---|---|
| (structure) | 27 | >50000 |
| (structure) | 113 | >50000 |
| (structure, Chiral) | 494 | >50000 |
| (structure, Chiral) | 220 | >50000 |
| (structure) | 12 | 36007 |
| (structure, Chiral) | 300 | >50000 |
| (structure, Chiral) | 42 | >50000 |
| (structure) | 7.1 | >50000 |

TABLE III-continued

| Compound | CB2 EC$_{50}$ (nM) | CB1 EC$_{50}$ (nM) |
|---|---|---|
| (structure) | 126 | >50000 |
| (structure) | 29 | >50000 |
| (structure) | 25 | >50000 |
| (structure) | 446 | nt |
| (structure) | 15 | 37646 |
| (structure) | 195 | >50000 |
| (structure) | 69 | >50000 |

TABLE III-continued

| Compound | CB2 EC$_{50}$ (nM) | CB1 EC$_{50}$ (nM) |
|---|---|---|
| 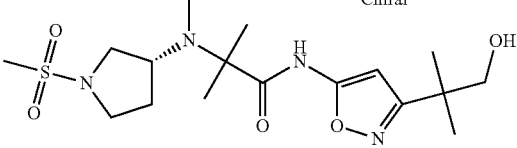 Chiral | 1.7 | >20000 |
| 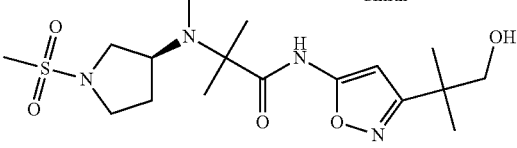 Chiral | 28 | >50000 |
| 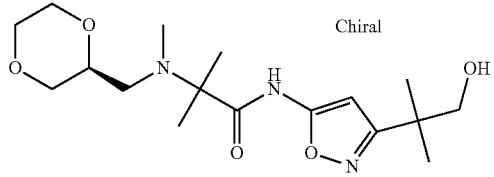 Chiral | 68 | >50000 |
| 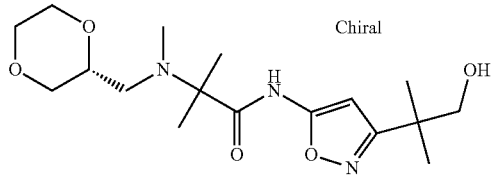 Chiral | 40 | >50000 |
| 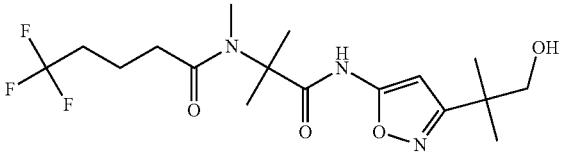 | 27 | 32068 |
| 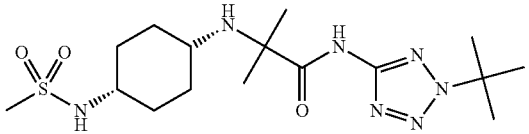 | 33 | >50000 |

In all the compounds disclosed hereinabove in this application, in the event the nomenclature is in conflict with the structure, it shall be understood that the compound is defined by the structure.

The invention also relates to pharmaceutical preparations, containing as active substance one or more compounds of formula (I), or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}$H, $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes methods using all such tautomers.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

Carbocycles include hydrocarbon rings containing from three to twelve carbon atoms. These carbocycles may be either aromatic either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4-8 membered (but preferably, 5 or 6 membered) monocyclic or nonaromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure.

The term "heteroaryl" shall be understood to mean an aromatic 5-8 membered monocyclic or 8-11 membered bicyclic ring containing 1-4 heteroatoms such as N, O and S.

Unless otherwise stated, heterocycles and heteroaryl include but are not limited to, for example benzoxazolyl, benzothiazolyl, benzimidazolyl, tetrahydropyranyl, dioxanyl, tetrahydrofuranyl, oxazolyl, isoxazolyl, thiazolyl, pyrazolyl, pyrrolyl, imidazolyl, thienyl, thiadiazolyl, triazolyl, thiomorpholinyl, 1,1-Dioxo-1$\lambda^6$-thiomorpholinyl, morpholinyl, pyridinyl, pyrimidinyl, pyridazinyl, pyrazinyl, triazinyl, pyrrolidinyl, piperidinyl, piperazinyl, purinyl, quinolinyl, Dihydro-2H-quinolinyl, isoquinolinyl, quinazolinyl, indazolyl, thieno[2,3-d]pyrimidinyl, indolyl, isoindolyl, benzofuranyl, benzopyranyl and benzodioxolyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative. For example, quinolinyl may include decahydroquinolinyl and tetrahydroquinolinyl, naphthyl may include its hydrogenated derivatives such as tetrahydronaphthyl. Other partially or fully hydrogenated derivatives of the aryl and heteroaryl compounds described herein will be apparent to one of ordinary skill in the art.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "halogen" as used in the present specification shall be understood to mean bromine, chlorine, fluorine or iodine, preferably fluorine. The definitions "partially or fully halogenated"; partially or fully fluorinated; "substituted by one or more halogen atoms", includes for example, mono, di or tri halo derivatives on one or more carbon atoms. For alkyl, a nonlimiting example would be —CH$_2$CHF$_2$, —CF$_3$ etc.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—(C$_1$-C$_4$ alkyl)$_4$$^+$ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula I may be made using the general synthetic methods described below, which also constitute part of the invention.

General Synthetic Methods

The invention also provides processes for making compounds of Formula (I) or Formula (II). In all Schemes, unless specified otherwise, $R^1$, $R^2$, $R^3$, $R^{3'}$, $R^4$, $R^5$ and A in the Formulas below shall have the meaning of $R^1$, $R^2$, $R^3$, $R^{3'}$, $R^4$, $R^5$ and A in Formula (I) or Formula (II) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization.

The examples which follow are illustrative and, as recognized by one skilled in the art, particular reagents or conditions could be modified as needed for individual compounds without undue experimentation. Starting materials and intermediates used, in the Schemes below, are either commercially available or easily prepared from commercially available materials by those skilled in the art.

The compounds of Formula (I) or Formula (II) may be synthesized according to Scheme 1:

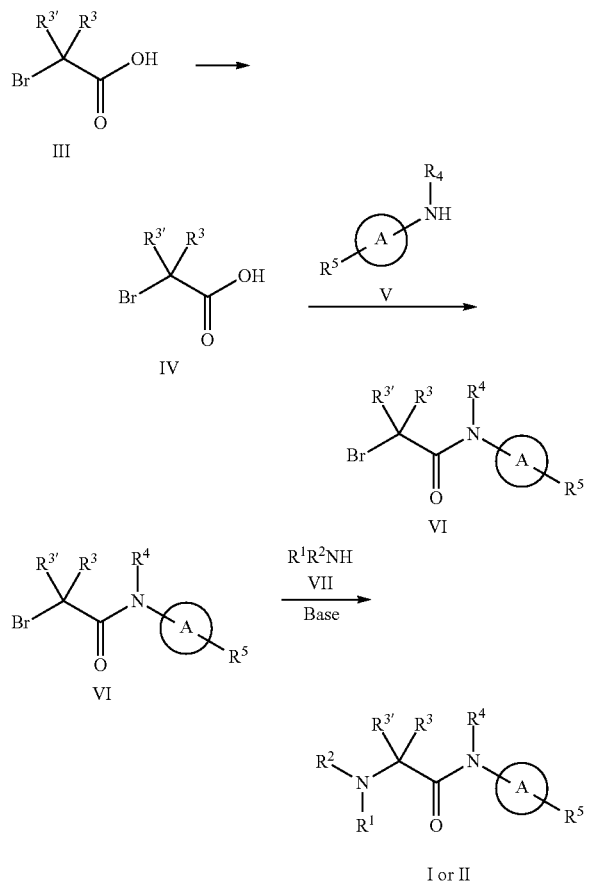

As illustrated in scheme 1, reaction of an acid of formula (III) with reagents such as thionyl chloride or oxalyl chloride provides the corresponding acid chloride of formula (IV). Reaction of this acid chloride (IV) with an amine of formula (V), in a suitable solvent, in the presence of a suitable base such as N,N-diisopropylethylamine, provides an amide of formula (VI).

Alternatively, the acid of formula (III) above may also be coupled with the corresponding amine of formula (V), under standard coupling conditions, to provide an amide of formula (VI). Standard peptide coupling reactions known in the art (see for example M. Bodanszky, 1984, The Practice of Peptide Synthesis, Springer-Verlag) may be employed in these syntheses. An example of suitable coupling conditions is treatment of a solution of the carboxylic acid in a suitable solvent such as DMF with EDC, HOBT, and a base such as diisopropylethylamine, followed by the desired amine.

Reaction of the intermediate of formula (VI) with an amine of formula (VII), in a suitable solvent, in the presence of a suitable base such as cesium carbonate, provides a compound of Formula (I) or Formula (II).

The compounds of Formula (I) or Formula (II) may be prepared according to Scheme 2:

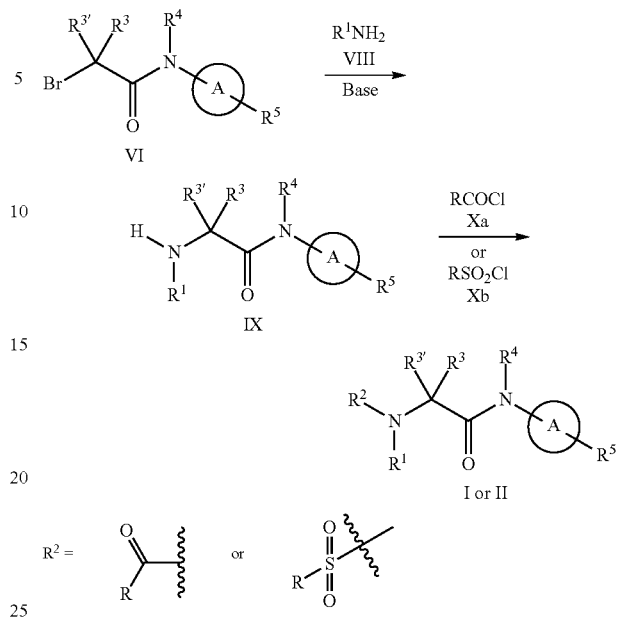

As outlined in scheme 2, reaction of an amide of formula (VI) with an amine of formula (VIII), in a suitable solvent, in the presence of a suitable base such as cesium carbonate, provides an amine of formula (IX). Reaction of the intermediate amine of formula (IX) with an acid chloride of formula (Xa) or a sulfonyl chloride of formula (Xb), in a suitable solvent, in the presence of a suitable base, provides a compound of Formula (I) or Formula (II) wherein $R^2$=R—C(O)— or R—$SO_2$—

The compounds of Formula (I) or Formula (II) may be synthesized as outlined in Scheme 3:

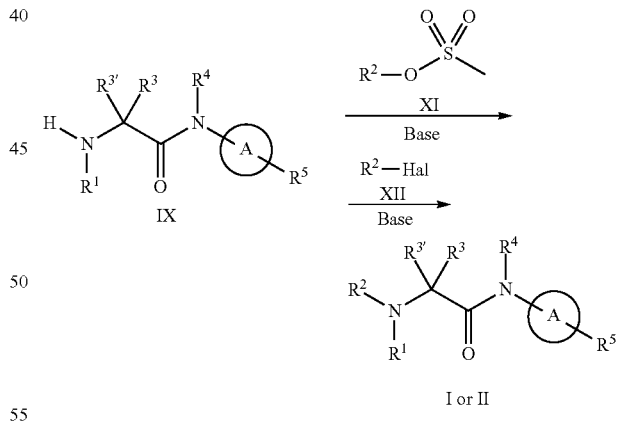

As illustrated in scheme 3, reaction of an amine of formula (IX) with a compound of formula (XI), in a suitable solvent, in the presence of a suitable base such as cesium carbonate, provides a compound of Formula (I) or Formula (II)

Alternatively, reaction of an amine of formula (IX) with a compound of formula (XII) wherein Hal=bromo or iodo, in a suitable solvent, in the presence of a suitable base such as sodium hydride, provides a compound of Formula (I) or Formula (II).

The compounds of Formula (I) or Formula (II) may be synthesized as shown in Scheme 4:

Scheme 4

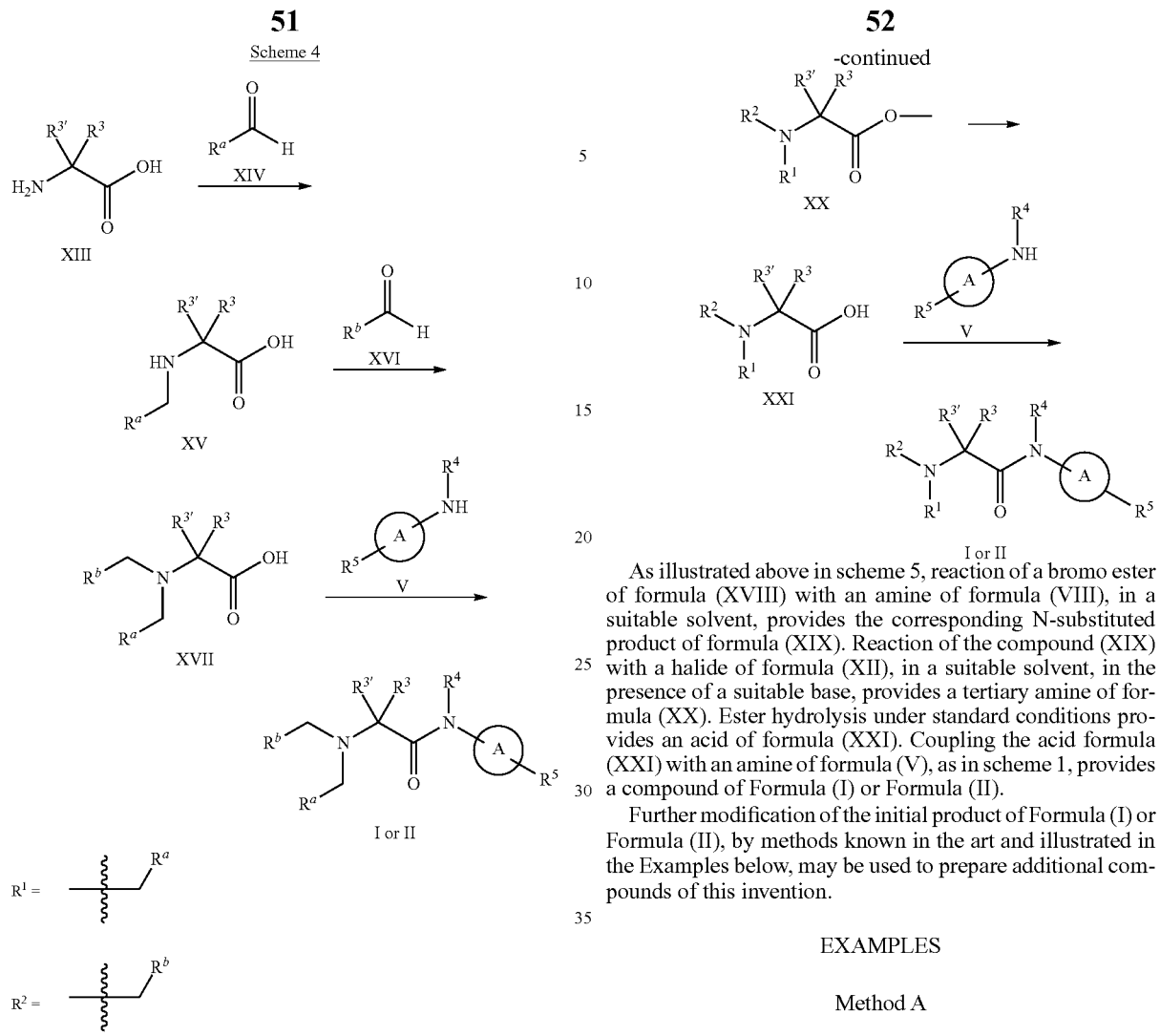

As shown in scheme 4, reaction of an amino acid of formula (XIII) with an aldehyde of formula (XIV), under standard reductive amination conditions, provides an amine of formula (XV). Further reaction of amine of formula (XV) with an aldehyde of formula (XVI) provides the corresponding amine of formula (XVII). Coupling the intermediate of formula (XVII) with an amine of formula (V), as in scheme 1, provides a compound of Formula (I) or Formula (II) wherein $R^1=R^a-CH_2-$ and $R^2=R^b-CH_2-$ The compounds of Formula (I) or Formula (II) may be synthesized according to Scheme 5:

Scheme 5

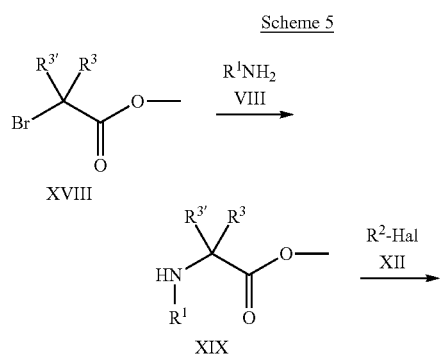

As illustrated above in scheme 5, reaction of a bromo ester of formula (XVIII) with an amine of formula (VIII), in a suitable solvent, provides the corresponding N-substituted product of formula (XIX). Reaction of the compound (XIX) with a halide of formula (XII), in a suitable solvent, in the presence of a suitable base, provides a tertiary amine of formula (XX). Ester hydrolysis under standard conditions provides an acid of formula (XXI). Coupling the acid formula (XXI) with an amine of formula (V), as in scheme 1, provides a compound of Formula (I) or Formula (II).

Further modification of the initial product of Formula (I) or Formula (II), by methods known in the art and illustrated in the Examples below, may be used to prepare additional compounds of this invention.

EXAMPLES

Method A

Synthesis of Example 1

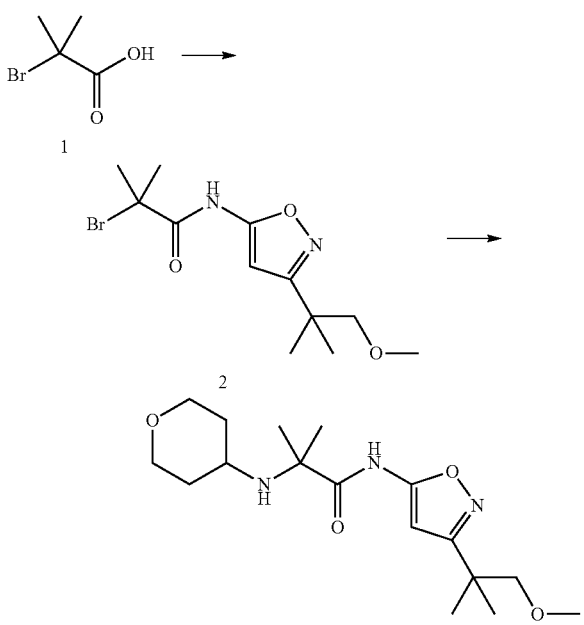

Step 1: Synthesis of Compound 2

To a flask containing 2-bromo-2-methyl-propionic acid (1) (0.6 g, 3.5 mmol) under nitrogen is added thionyl chloride (2 mL). The reaction mixture is heated to 70° C. where it is maintained for 2 h. After this time, the reaction is cooled to room temperature and concentrated under reduced pressure. The crude acid chloride is used without further purification.

The crude acid chloride is dissolved in dichloromethane (DCM) (5 mL) and N,N-diisopropylethylamine (1 mL, 5.7 mmol) is added followed by 3-(2-methoxy-1,1-dimethyl-ethyl)-isoxazol-5-ylamine (0.6 g, 3.5 mmol).

The reaction is stirred for 16 h at room temperature. After this time, additional 2-bromo-2-methyl-propionic acid (0.3 g, 1.7 mmol) is activated as its acid chloride, as described above) and added to the reaction mixture. After further 1.5 h stirling, the mixture is washed with saturated aqueous $NaHCO_3$ solution (×2), brine and the organic layer is separated, dried ($MgSO_4$) and concentrated under reduced pressure. The crude product is purified by chromatography (silica, eluent: heptanes, 20% ethyl acetate) to provide compound 2 (0.6 g, 51%);

According to the above procedure the following intermediates are synthesised:

Step 2: Synthesis of Example 1

To a solution of 4-aminotetrahydropyran (0.1 g, 0.94 mmol) in THF (2 mL) are added $Cs_2CO_3$ (0.6 g, 1.84 mmol) and compound 2 (0.3 g, 0.94 mmol). The reaction is heated to 50° C. for 3 h. The solvent is then removed under reduced pressure and the residue is partitioned between DCM and 1M aqueous HCl solution. The acidic aqueous layer is basified with 5N aqueous NaOH solution and extracted with DCM (3×10 mL). The combined organic extracts are washed with brine, dried ($MgSO_4$), filtered and concentrated under reduced pressure. The crude product is purified by column chromatography (silica, eluent: heptanes, 50% ethyl acetate) to yield example 1 (0.15 g, 41%). LC-MS (LC Method a): retention time: 2.40 min, m/z 340 [M+H]

Compounds listed in Table IV under method A are made following this procedure.

TABLE 1

| Intermediate No. | Structure | Yield (%) | LC Method and Retention time [min] | m/z [M + H] |
|---|---|---|---|---|
| I (compound 2) | 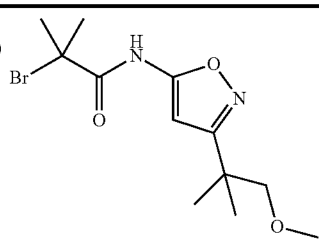 | 51 | LC Method b: 1.90 | 319/321 |
| II | 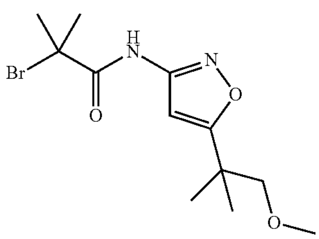 | 54 | LC Method b: 1.96 | 319/321 |

Method B

Synthesis of Example 2

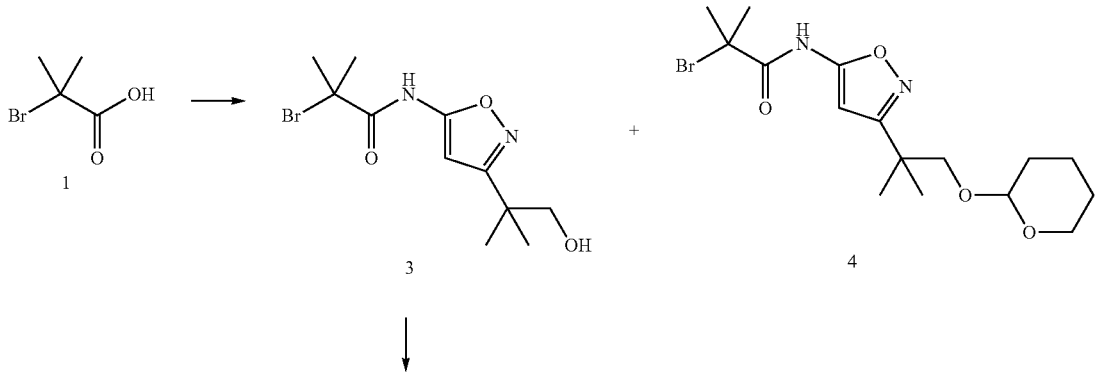

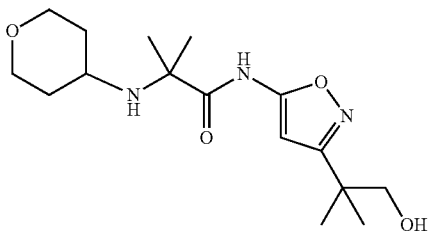

Example 2

Step 1: Synthesis of Compound 3

To a flask containing compound 1 (3 g, 18 mmol) under nitrogen is added thionyl chloride (6.6 mL). The reaction mixture is heated to 70° C. where it is maintained for 3 h. After this time, the reaction is cooled to room temperature and concentrated under reduced pressure. The crude acid chloride is used without further purification.

The crude acid chloride is dissolved in THF (11 mL) and N,N-diisopropylethylamine (3.1 mL, 18 mmol) is added, followed by 3-[1,1-dimethyl-2-(tetrahydro-pyran-2-yloxy)-ethyl]-isoxazol-5-ylamine (4.3 g, 18 mmol). The reaction is stirred for 16 h at 40° C. The mixture is washed with saturated aqueous NaHCO$_3$ solution (×2), brine and the organic layer is separated, dried (MgSO$_4$) and concentrated under reduced pressure. Purification of the residue by chromatography (silica, eluent: heptanes, 20% ethyl acetate) allows separation and isolation of compound 3 (1 g, 18%), m/z 305/307 [M+H$^+$], from compound 4 (0.9 g, 13%), LC-MS (LC Method b): retention time: 2.35 min, m/z 411/413 [M+Na+H].

Step 2: Synthesis of Example 2

To a solution of 4-aminotetrahydropyran (0.05 g, 0.5 mmol) in THF (3 mL) are added Cs$_2$CO$_3$ (0.3 g, 1 mmol) and compound 3 (0.15 g, 0.5 mmol). The reaction is heated to 50° C. for 18 h. The solvent is then removed under reduced pressure and the residue is partitioned between DCM and 1M aqueous HCl solution. The acidic aqueous layer is basified with 5N aqueous NaOH solution and extracted with DCM (3×10 mL). The combined organic extracts are washed with brine, dried (MgSO$_4$), filtered and concentrated under reduced pressure. The crude product is purified twice by column chromatography (silica, eluent: heptanes, 20% EtOAc) followed by trituration with 1M HCl in dioxane to yield the hydrochloride salt of example 2 (0.04 g, 22%). LC-MS (LC Method a): retention time: 2.16 min, m/z 326 [M$_{freebase}$+H]

Compounds listed in Table IV under method B are made following this procedure.

Method C

Synthesis of Example 3

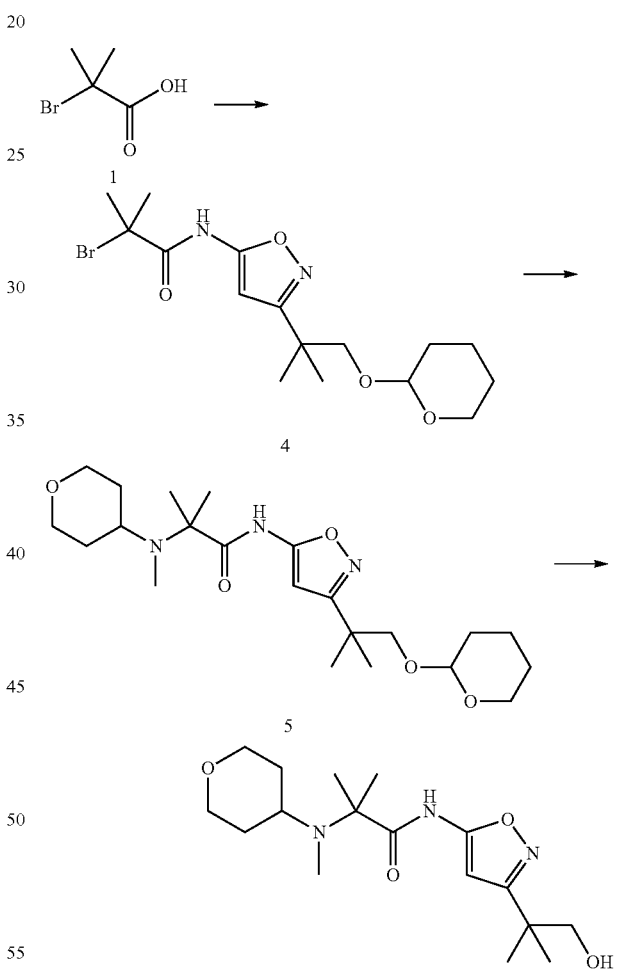

Example 3

Step 1: Synthesis of Compound 4

To a flask containing compound 1 (20.85 g, 125 mmol) in DCM (150 mL) under nitrogen is added oxalyl chloride (16.2 mL, 187.3 mmol), followed by DMF (5 drops). The reaction mixture is stirred at room temperature for 16 h and then concentrated under reduced pressure. The crude acid chloride, used without further purification, is dissolved in toluene (50 mL) and added dropwise over 10 min to a solution of N,N-diisopropylethylamine (32.6 mL, 187 mmol) and 3-[1,1-dimethyl-2-(tetrahydro-pyran-2-yloxy)-ethyl]-isoxazol-5-ylamine (15 g, 62.4 mmol) in toluene (300 mL) at 50° C. The reaction is stirred for 4 h at 60° C. The reaction mixture is concentrated under reduced pressure and the residue is partitioned between DCM (300 mL) and water (250 mL). The organic layer is separated and dried over Na$_2$SO$_4$, filtered and concentrated under reduced pressure. The crude orange oil is dissolved in diethyl ether and precipitated by addition of n-heptanes. The precipitate is isolated by filtration and washed sparingly with diethyl ether/heptanes to yield the first crop (9 g) of compound 4 as off-white solid. The mother liquor is concentrated and a second crop (3.3 g) is isolated by crystallisation/precipitation from diethyl ether/heptanes. The mother liquor is concentrated under reduced pressure and the residual orange oil filtered through silica (eluent: heptanes, 20% ethyl acetate), the filtrate is concentrated. The residue is dissolved in diethyl ether and the third crop (3.1 g) is isolated by diethyl ether/heptanes treatment as described above. The combined yield of crop 1-3 is 15.4 g. Yield 63%; LC-MS (LC Method b): retention time: 2.35 min, m/z 411/413 [M+Na+H].

Step 2: Synthesis of Compound 5

A solution of N-methyl-(tetrahydro-pyran-4-yl)-amine (0.25 g, 2.17 mmol), Cs$_2$CO$_3$ (1.41 g, 4.34 mmol) and compound 4 (0.85 g, 2.17 mmol) in THF (20 mL) is stirred at room temperature for 72 h. The reaction mixture is filtered through Celite®, the solids are washed with ethyl acetate and DCM and the filtrate is concentrated under reduced pressure. The residue is purified by column chromatography (silica, eluent: heptanes, 50-100% ethyl acetate) to yield 374 mg of compound 5. Yield 41%; LC-MS (LC Method b): retention time: 1.51 min, m/z 424 [M+H]

The following amines are synthesised by adaptation of the above procedure with the following modification to be noted:

For intermediate II and III: excess of the corresponding amine (2.5 equ) and Cs$_2$CO$_3$ (2 equ.) are used, the work-up procedure includes a wash of the organic layer with 10% aqueous citric acid solution followed by brine and the product is isolated by column chromatography (silica, eluent heptanes, 30% ethyl acetate).

For intermediate XI the reaction is stirred for 48 h at ambient temperature.

For intermediate XII and X: the reaction mixture is filtered through celite and washed with DCM. The solvent is removed under reduced pressure and the product purified by column chromatography (silica, eluent; heptanes, 0-50% ethyl acetatec)

According to the above procedure the following intermediates are synthesised:

TABLE 2

| Intermediate No. | Structure | Yield [%] | LC Method and Retention time [min]] | m/z [M + H] |
|---|---|---|---|---|
| III (compound 5) | 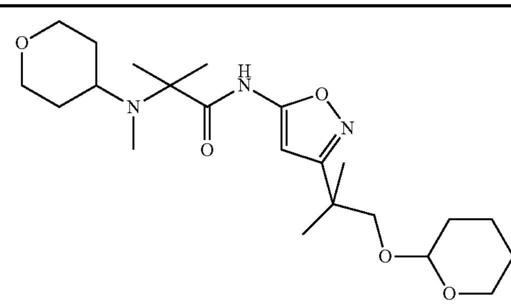 | 41 | LC Method b: 1.51 | 424 |
| IV | 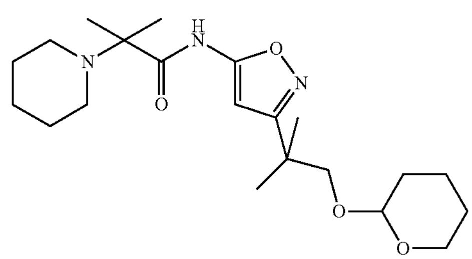 | 68 | LC Method b: 1.46 | 394 |
| V | 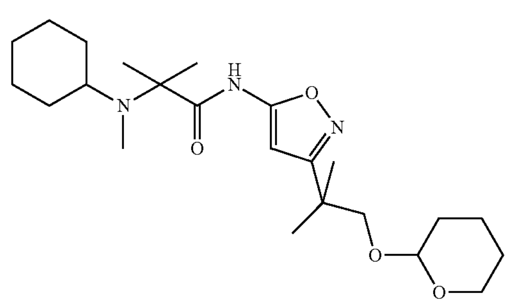 | 51 | LC Method b: 2.11 | 423 |

TABLE 2-continued

| Intermediate No. | Structure | Yield [%] | LC Method and Retention time [min] | m/z [M + H] |
|---|---|---|---|---|
| VI | 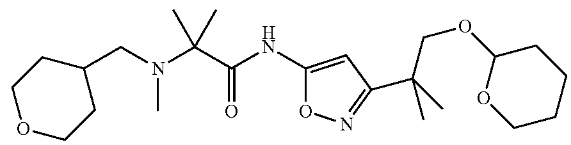 | 27 | not available/ see Footnote a | 438 |
| VII | 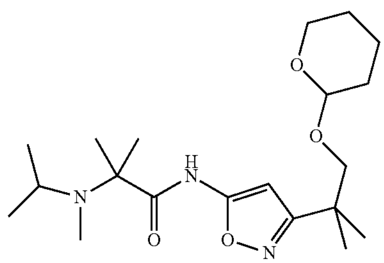 | 51 | not available/ see Footnote b | 382 |
| VIII | 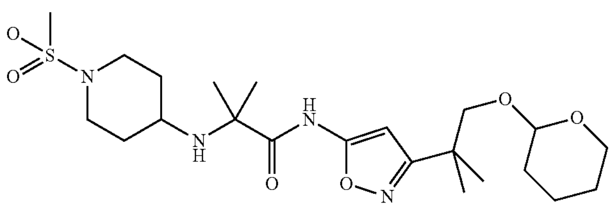 | 66 | not available/ see Footnote c | 487 |
| IX | 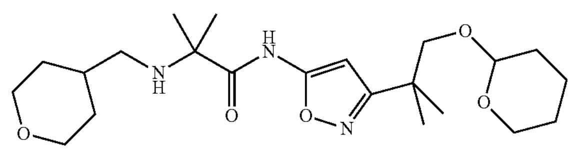 | 27 | LC Method a: 2.89 | 424 |
| X | 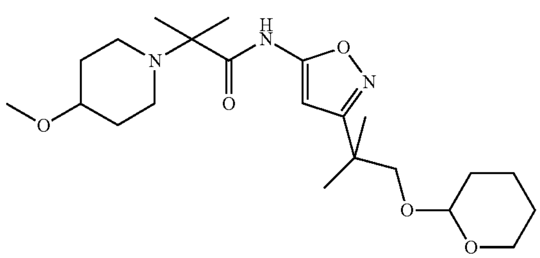 | 27 | LC Method b: 2.05 | 424 |
| XI | 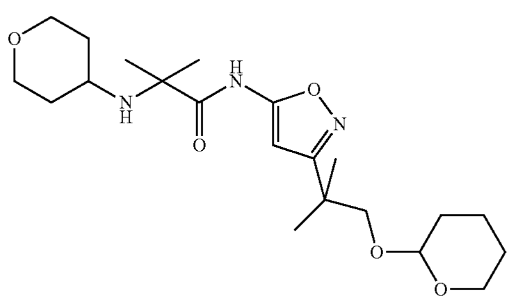 | 34 | LC Method a: 2.74 | 410 |

TABLE 2-continued

| Intermediate No. | Structure | Yield [%] | LC Method and Retention time [min] | m/z [M + H] |
|---|---|---|---|---|
| XII | 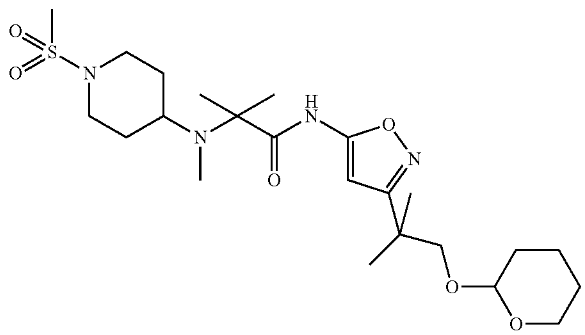 | 31 | LC Method b: 1.48 | 501 |
| XIII | 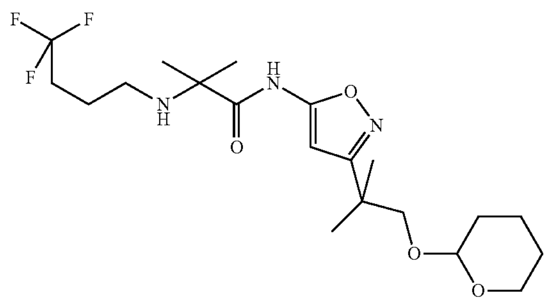 | n.d.# | LC Method b: 1.50 | 436 |
| XIV | 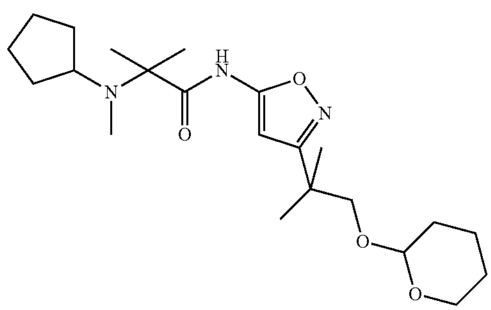 | 28 | LC Method b: 1.54 | 408 |
| XV | 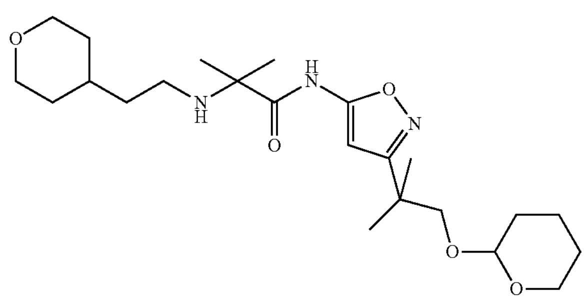 | 97 | LC Method b: 1.51 | 438 |
| XVI | 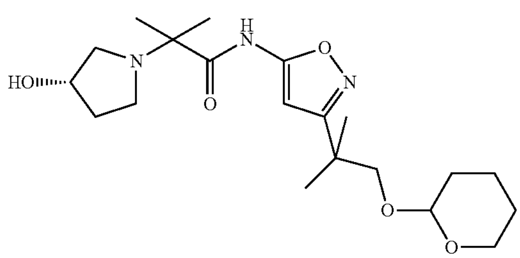 | n.d.# | LC Method b: 1.34 | 396 |

TABLE 2-continued
| Intermediate No. | Structure | Yield [%] | LC Method and Retention time [min] | m/z [M + H] |
|---|---|---|---|---|
| XVII | 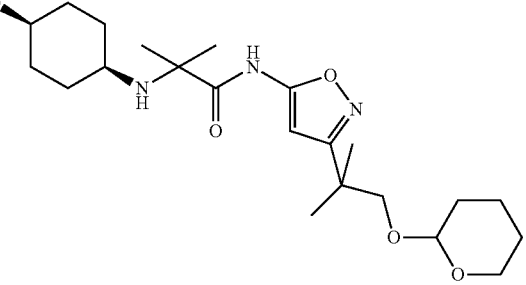 | n.d.# | LC Method b: 1.69 | 424 |
| XVIII | 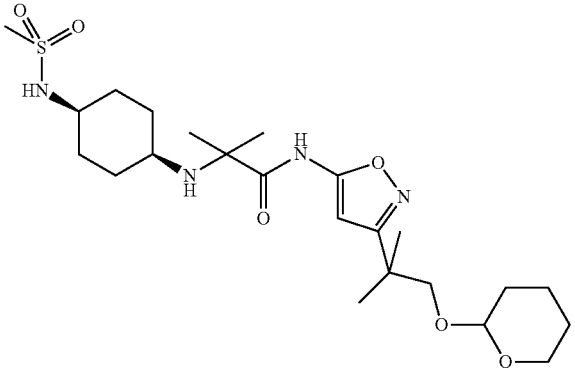 | n.d.# | LC Method b: 1.45 | 499 [M − H] |
| XIX | 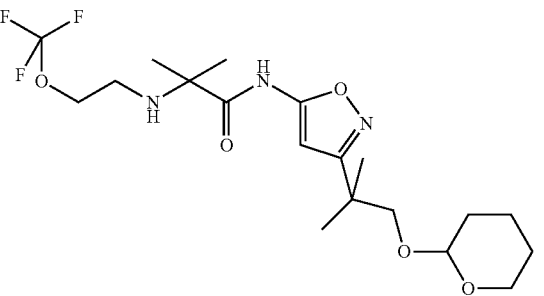 | n.d.# | LC Method b: 1.71 | 436 [M − H] |
| XX | 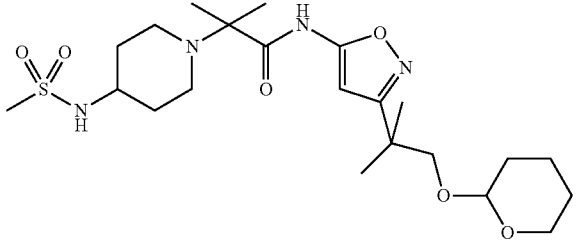 | n.d.# | LC Method b: 1.43 | 487 |
| XXI | 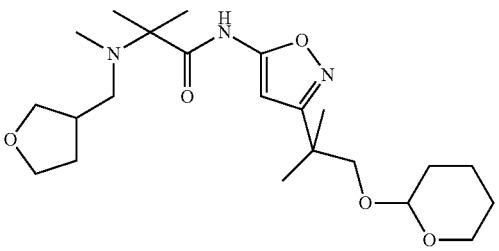 | 55 | LC Method b: 1.48 | 424 |

TABLE 2-continued

| Intermediate No. | Structure | Yield [%] | LC Method and Retention time [min] | m/z [M + H] |
|---|---|---|---|---|
| XXII | 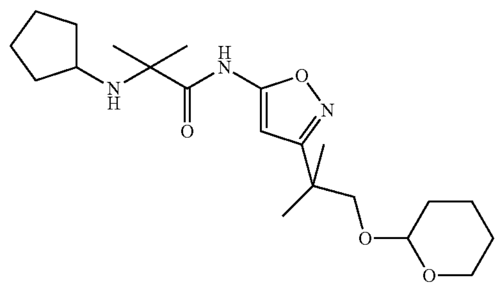 | 56 | LC Method b: 1.33 | 394 |
| XXIII | 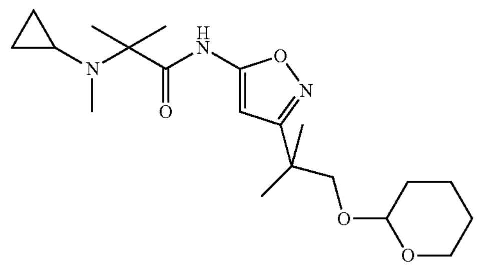 | 78 | LC Method b: 1.70 | 380 |
| XXIV | 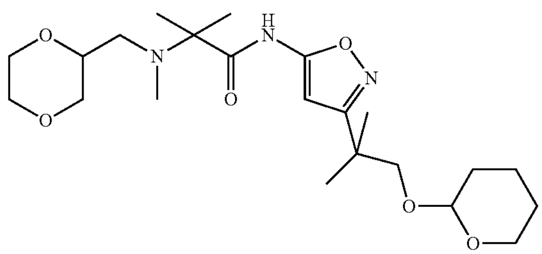 | 32 | LC Method b: 1.99 | 438 [M − H] |
| XXV | 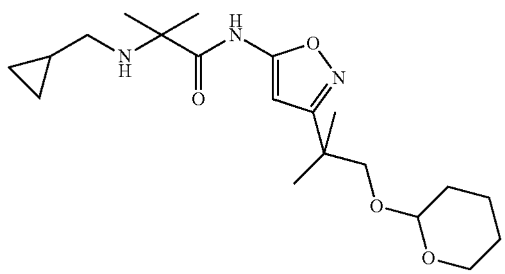 | 22 | LC Method b: 1.29 | 380 |
| XXVI | 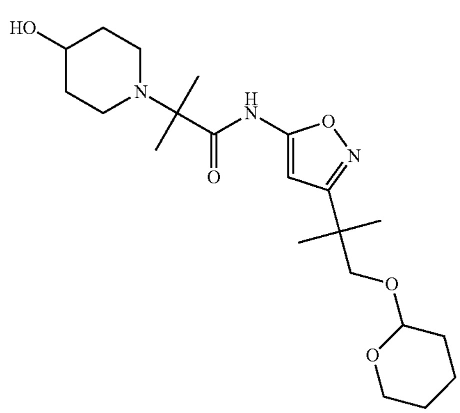 | n.d.# | LC Method b: 1.49 | 410 |

TABLE 2-continued

| Intermediate No. | Structure | Yield [%] | LC Method and Retention time [min] | m/z [M + H] |
|---|---|---|---|---|
| XXVII | F-C(F)(F)-CH2-CH2-NH-C(CH3)2-C(O)-NH-isoxazole-C(CH3)2-CH2-O-THP | 34 | LC Method b: 1.64 | 420 [M − H] | a) n.d.# intermediate is carried through to the next step without further purificationa) Intermediate VI: $^1$H NMR (400 MHz, chloroform-d) δ ppm 1.26 (6H, s), 1.34 (3H, s), 1.37 (3H, s), 1.47-1.83 (11H, m), 2.18 (2H, d, 7.2 Hz), 2.22 (3H, s), 3.36-3.50 (3H, m), 3.77-3.82 (3H, m), 3.99 (2H, m), 4.57 (1H, m), 6.32 & 6.38 (1H, 2s), 9.4-9.8 (1H, br)
b) Intermediate VII: $^1$H NMR (400 MHz, chloroform-d) δ ppm 1.07 (6H, d, J = 6.4 Hz), 1.32-1.37 (12H, m), 1.46-1.84 (6H, m), 2.19 (3H, s), 2.98 (1H, q), 3.37 (1H, d, J = 9.6 Hz), 3.45-3.50 (1H, m), 3.76-3.81 (2H, m), 4.57 (1H, t, J = 6.8 Hz), 6.32 (1H, s), 10.10 (1H, br)
c) Intermediate VIII: $^1$H NMR (400 MHz, chloroform-d) δ ppm 1.25 (12H, s), 1.31-1.76 (10H, m), 2.70 (2H, t, 11.2 Hz), 2.80 (3H, s), 3.31-3.42 (6H, m), 3.62-3.66 (2H, m), 4.53 (1H, s), 6.25 (1H, s), 6.80 (1H, br)

Step 3: Synthesis of Example 3

To a solution of compound 5 (806 mg, 1.9 mmol) in DCM/ethanol (1/1, 16 mL) is added polymer-supported tosic acid (MP-TsOH (65), loading 3.3 mmol/g, 1.74 g). The mixture is shaken on an orbital-shaker at room temperature for 18 h. The resin is isolated by filtration and washed with DCM and methanol. The product is then released form the resin with 7M solution of ammonia in methanol. The resin is further rinsed with methanol and DCM. Concentration of the basic filtrate gives a clear oil which is triturated with diethyl ether/heptanes to afford 549 mg of example 3 as a white solid. Yield 85%, LC-MS (LC Method a): retention time: 2.17 min m/z 410 [M+H]; mp 129-131° C.

Compounds listed in Table IV under method C are made following this procedure, with the following modification for examples 7-9, and 20: Pyridinium p-toluenesulfonate (1.2 equ) is used instead of MP-TsOH and the reaction is performed under refluxing conditions (4 h) in EtOH instead of DCM/ethanol.

Example 86-87 are separated by chiral preparative LC.

Example 4 and 5 are converted into the oxalate salt by stirring in the presence of oxalic acid (1 equ) in ethanol at 50° C., followed by concentration under reduced pressure.

Examples 42, 43, 45, 47, 48, 49, 51, 53, 56, 57, 60, 63, 64, 68, 86, 87 are converted into the hydrochloride salt by stirring in the presence of 1M HCl solution in diethyl ether (2 eq) at room temperature, followed by concentration under reduced pressure.

Method D

Synthesis of Example 6

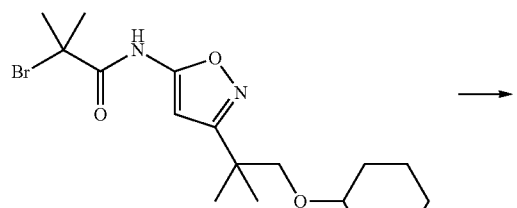

4

-continued

Example 6

A solution of 2-methylpiperidine (40 mg, 0.33 mmol), Cs$_2$CO$_3$ (218 mg, 0.66 mmol) and compound 4 (130 mg, 0.33 mmol) in THF (10 mL) is heated to 55° C. for 3 h in a pressure tube. After cooling to room temperature, the reaction mixture is diluted with ethyl acetate (40 mL) and washed with brine (2×15 mL), dried (MgSO$_4$), filtered and concentrated under reduced pressure. The residue is purified by column chromatography (silica, eluent: heptanes, 10% ethyl acetate) and then using a Flash SCX-2 cartridge (Isolute®) (eluent: DCM, methanol then 5% NH$_3$/MeOH) which removes the tetrahydropyranyl protecting group. Final purification using silica, eluent: heptanes, 10% ethyl acetate) yield 23 mg of example 6. Yield 22%. LC-MS (LC Method a): retention time: 2.35 min, m/z 324 [M+H]

A portion of example 6 is converted into its hydrochloride salt by stirring in the presence of 1M HCl solution in diethyl ether (2 equ.) at room temperature, followed by concentration under reduced pressure.

Compounds listed in Table IV under method D are made following this procedure

Method E

Synthesis of Example 10

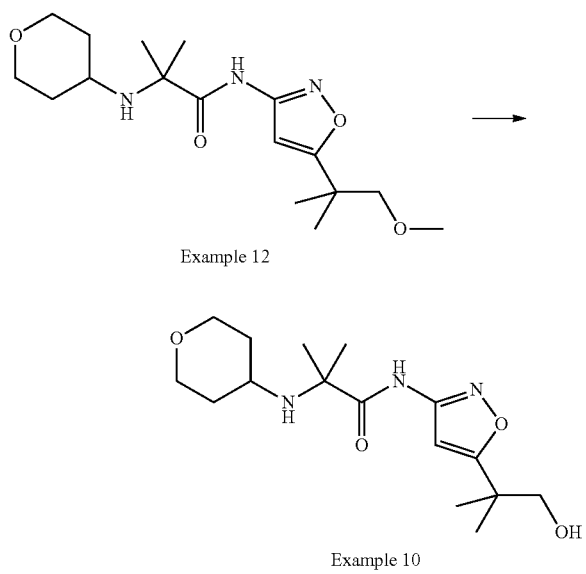

Example 12

Example 10

Example 12 (80 mg, 0.24 mmol, prepared according to Method A) and 600 mg (2.35 mmol) of aluminum tribromide are dissolved in ethanethiol (4 mL, CAUTION: stench) and stirred at room temperature for 3 h. The reaction is quenched by addition of water (8 mL) and acidified by careful addition of 1 M aqueous HCl solution to pH 4-5. The reaction mixture is extracted with ethyl acetate (3×10 mL) and the combined organic layers are washed with brine, dried over $Na_2SO_4$ and filtered. The filtrate is concentrated under reduced pressure and the residue purified by column chromatography (silica, eluent: DCM, 50% ethyl acetate) to afford 50 mg of example 10. Yield 65%, LC-MS (LC Method a): retention time: 2.14 min, m/z 326 [M+H]

Compounds listed in Table IV under method E are made following this procedure

Method F

Synthesis of Example 46

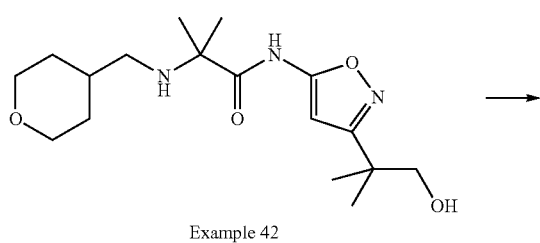

Example 42

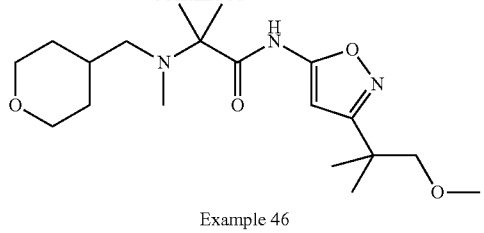

Example 46

To a solution of example 42 (0.34 g, 1.01 mmol) and NaH (0.12 g, 3.04 mmol, 60% dispersion in mineral oil,) in THF (6 mL) is added methyl iodide (95 µL, 1.52 mmol). The reaction mixture is stirred at room temperature for 18 h and filtered through celite. The crude product is purified by preparative HPLC (neutral method) to yield 53 mg of example 46 as a colourless oil. Yield: 17%, LC-MS (LC Method a): retention time: 2.60 min, m/z 368 [M+H]. example 46 is converted to the hydrochloride salt by stirring in the presence of 2M solution of hydrogen chloride in diethyl ether (1 mL) at room temperature, followed by concentration under reduced pressure.

Compounds listed in Table IV under method F are made following this procedure

Method G

Synthesis of Example 50

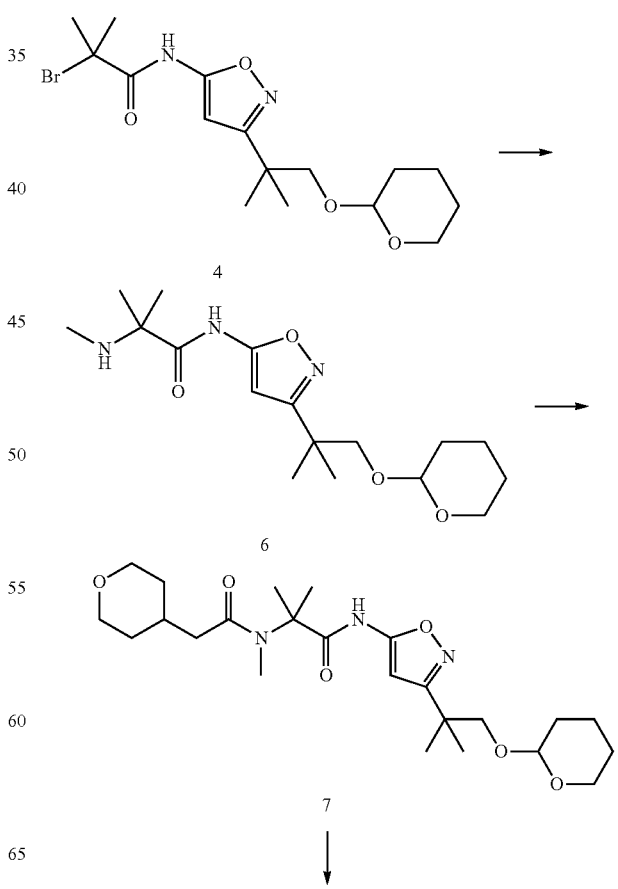

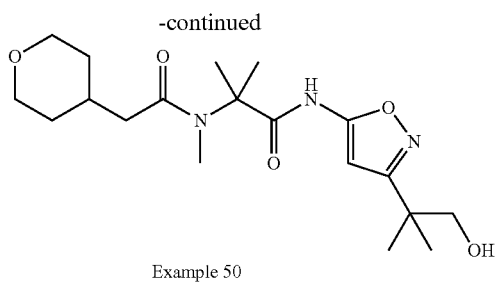

Example 50

Step 1: Synthesis of Compound 6

A solution of methylamine (2.89 mL, 23.1 mmol), $Cs_2CO_3$ (0.75 g, 2.3 mmol) and compound 4 (0.45 g, 1.2 mmol) in THF (10 mL) is heated to 65° C. in a sealed tube for 3 h. The reaction mixture is cooled and diluted with ethyl acetate (20 mL). The mixture is washed with brine (8 mL). The organic layer is dried ($MgSO_4$), filtered and the filtrate is concentrated under reduced pressure. The crude product is purified by column chromatography (silica, eluent: heptanes, 0-50% ethyl acetate) to yield 0.29 g of compound 6. Yield: 74%; LC-MS (LC Method b): retention time: 1.24 min, m/z 340 [M+H].

Step 2: Synthesis of Compound 7

To a solution of compound 6 (0.2 g, 0.59 mmol) and N,N-diisopropylethylamine (0.2 mL, 1.18 mmol) in THF (8 mL) is added (tetrahydro-pyran-4-yl)-acetyl chloride (0.11 g, 0.59 mmol). The reaction is heated to 60° C. for 18 h and the solvent is removed under reduced pressure. The residue is dissolved in ethyl acetate (20 mL) and washed with water (2×5 mL) and brine (2×5 mL). The organic layer is dried ($MgSO_4$), filtered and the filtrate is concentrated under reduced pressure. The residue is purified by column chromatography (silica, eluent: heptanes, 0-50% ethyl acetate) to yield 0.25 g of compound 7; yield: 94%, LC-MS (LC Method b): retention time: 1.90 min, m/z 464 [M−H].

According to the above method the following intermediates are synthesised with the following modifications to be noted:

For intermediate XXX and XXXIII, the corresponding acid is converted into its acidchloride by treatment with oxalylchloride (4 equ.) and DMF (cat) in DCM at room temperature for 4 h. The reaction mixture is concentrated under reduced pressure and the crude acid chloride is used in the above procedure without further purification.

Intermediates XXXI and XXXII are synthesised using standard amide coupling conditions: 1 equ of compound 6 is coupled with the corresponding acid (1 equ) using EDC.HCl (3 equ) and DMAP (1 equ) in acetonitrile. The reaction mixture is stirred at room temperature for 18 h and the concentrated under reduced pressure. The residue is purified by column chromatography (silica, eluent:n-heptanes, 30% ethyl actetate) to afford the desired intermediate.

According to the above procedure the following intermediates are synthesised:

TABLE 3

| Intermediate No. | Structure | Yield [%] | LC Method and Retention time [min] | m/z [M + H] |
|---|---|---|---|---|
| XXVIII (compound 7) | 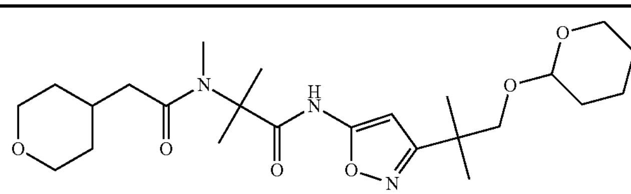 | 94 | LC Method b: 1.90 | 464 [M − H] |
| XXIX | 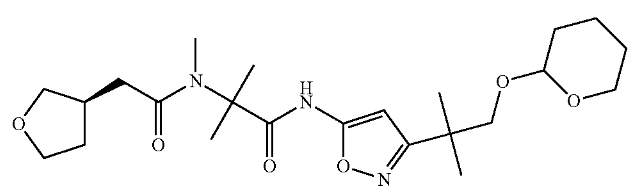 | 22 | LC Method b: 1.83 | 474 [M + Na] |
| XXX | 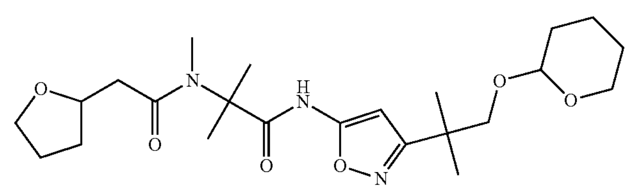 | 86 | LC Method b: 1.89 | 474 [M + Na] |
| XXXI | 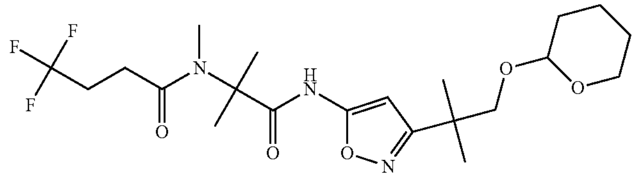 | 69 | LC Method b: 2.08 | 486 [M + Na] |

TABLE 3-continued

| Intermediate No. | Structure | Yield [%] | LC Method and Retention time [min] | m/z [M + H] |
| --- | --- | --- | --- | --- |
| XXXII | 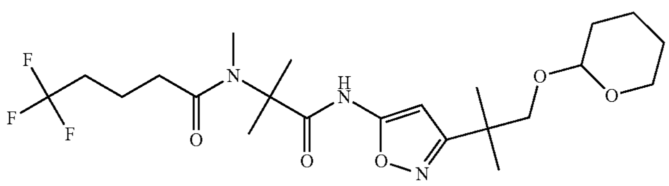 | 82 | LC Method b: 2.11 | 500 [M + Na] |
| XXXIII | 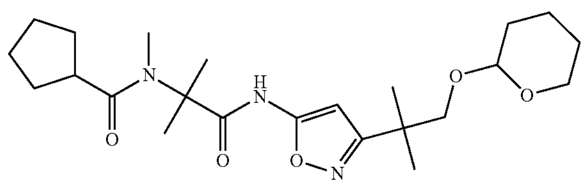 | 35 | LC Method b: 2.10 | 458 [M + Na] |

Step 3: Synthesis of Example 50

Compound 7 is deprotected by shaking in the presence of polymer-supported tosic acid (MP-TsOH (65), loading 3.3 mmol/g, 0.6 g) on an orbital shaker for 18 h. The resin is removed by filtration and washed with DCM. The product is released from the resin by treatment with 7M ammonia in methanol and the filtrate is concentrated under reduced pressure and the residue is purified by preparative HPLC (neutral method) to afford 40 mg of example 50. Yield 18%, LC-MS (LC Method a): retention time: 3.06 min, m/z 382 [M+H].

Compounds listed in Table IV under method G are made following this procedure

Method H

Synthesis of Example 52

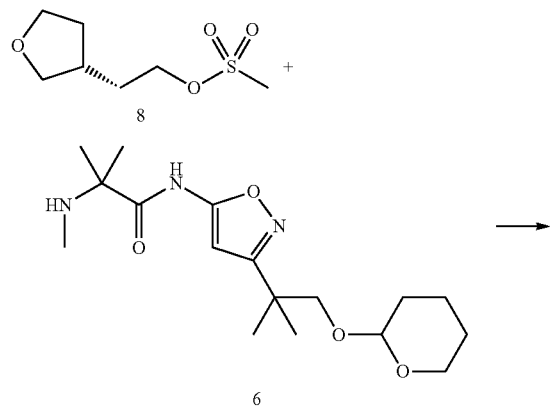

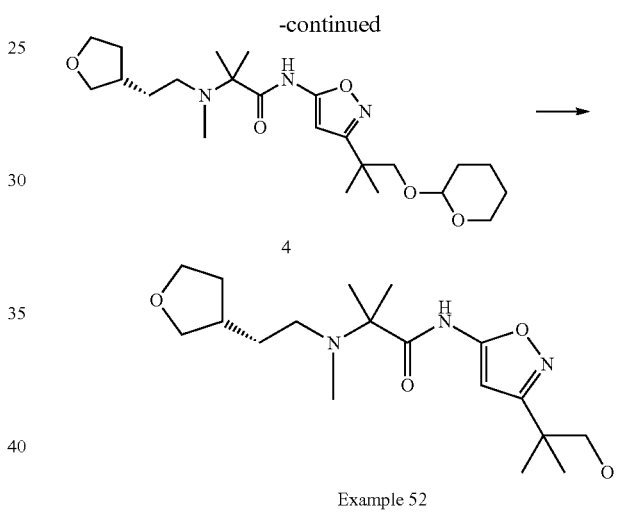

Example 52

Step 1: Synthesis of Compound 9

To a solution of compound 6 (0.2 g, 0.59 mmol, prepared according to Method G, step 1) and Cs$_2$CO$_3$ (0.38 g, 1.18 mmol) in THF (3 mL) is added compound 8 (115 mg, 1.0 mmol, prepared as described in Gosh, A. K. et al. *J. Med. Chem.* 1993, 36, 2300-2310). The reaction is heated to 65° C. for 3 h in a sealed tube and diluted in ethyl acetate (12 mL). The organic layer is washed with brine (8 mL) and dried (MgSO$_4$). The solvent is removed under reduced pressure and purified by column chromatography (silica, eluent: heptanes, 0-50% ethyl acetate) to afford 0.2 g of compound 9. Yield: 12%; LC-MS (LC Method b): retention time: 1.37 min, m/z 438 [M+H].

Step 2: Synthesis of Example 52

To a solution of compound 9 in DCM/methanol (1/1, 4 mL) is added polymer-supported tosic acid (MP-TsOH (65), loading 3.3 mmol/g, 0.28 g) and the reaction mixture is shaken on an orbital shaker for 18 h. The resin is removed by filtration and washed with DCM. The product is released from the resin by treatment with 7M ammonia solution in methanol and the resin is further washed with methanol and DCM. The filtrate is concentrated under reduced pressure. The residue is purified by preparative LC (neutral method) to afford 69 mg of example 52 as a clear oil, yield 36%, LC-MS (LC Method a): retention time: 2.19 min, m/z 354 [M+H], which is converted in its hydrochloride salt by treatment with 2M HCl in diethyl ether (0.12 mL) and concentration under reduced pressure. The crude material is recrystallised from ethyl acetate/heptanes to afford the hydrochloride salt of example 52 as a white crystalline solid.

Compounds listed in Table IV under method H are made following this procedure

Method I

Synthesis of Example 54

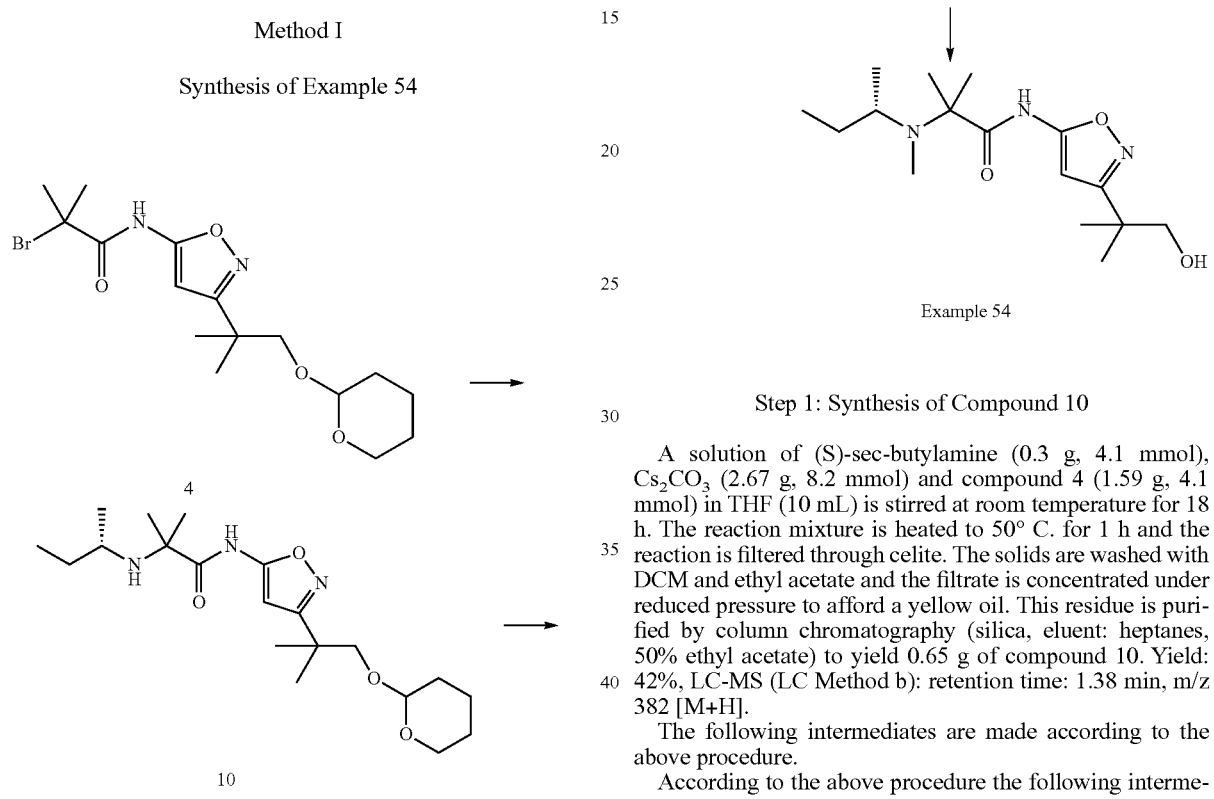

Example 54

Step 1: Synthesis of Compound 10

A solution of (S)-sec-butylamine (0.3 g, 4.1 mmol), Cs₂CO₃ (2.67 g, 8.2 mmol) and compound 4 (1.59 g, 4.1 mmol) in THF (10 mL) is stirred at room temperature for 18 h. The reaction mixture is heated to 50° C. for 1 h and the reaction is filtered through celite. The solids are washed with DCM and ethyl acetate and the filtrate is concentrated under reduced pressure to afford a yellow oil. This residue is purified by column chromatography (silica, eluent: heptanes, 50% ethyl acetate) to yield 0.65 g of compound 10. Yield: 42%, LC-MS (LC Method b): retention time: 1.38 min, m/z 382 [M+H].

The following intermediates are made according to the above procedure.

According to the above procedure the following intermediates are synthesised:

TABLE 4

| Intermediate No. | Structure | Yield [%] | LC Method and Retention time [min] | m/z [M + H] |
|---|---|---|---|---|
| XXXIV (compound 10) | 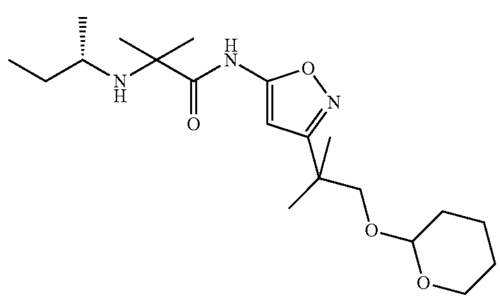 | 25 | LC Method b: 1.38 | 382 |

TABLE 4-continued

| Intermediate No. | Structure | Yield [%] | LC Method and Retention time [min] | m/z [M + H] |
|---|---|---|---|---|
| XXXV | 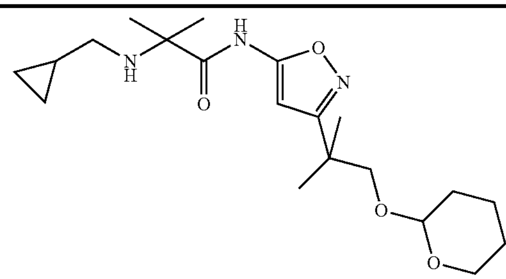 | 22 | LC Method b: 1.29 | 380 |
| XXXVI | 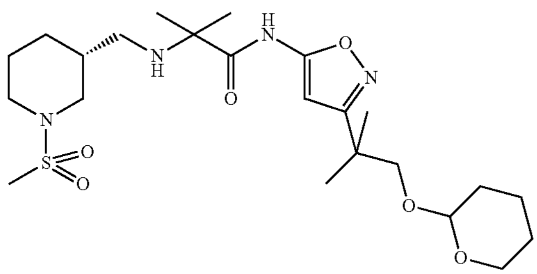 | 37 | LC Method b: 1.47 | 501 |
| XXXVII | 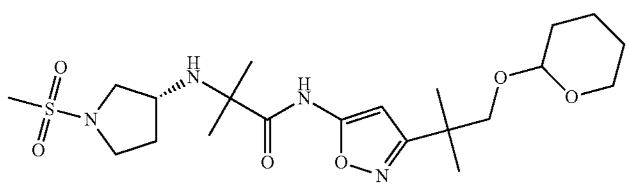 | 48 | LC Method b: 1.50 | 471 [M − H] |
| XXXVIII | 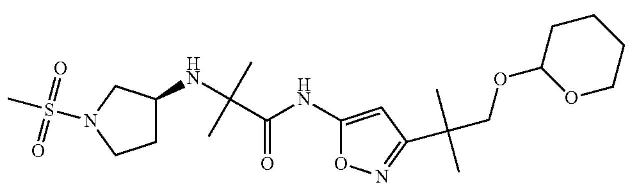 | 50 | LC Method b: 1.50 | 471 [M − H] |
| XXXIX | 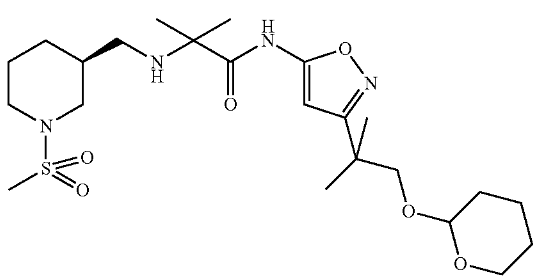 | 66 | LC Method b: 1.43 | 501 |

Step 2: Synthesis of Compound 11

To a solution of the compound 10 (392 mg, 1.02 mmol) in THF (3 mL) is added sodium hydride (41 mg, 1.02 mmol, 60% dispersion in mineral oil) and methyl iodide (64 μl, 1.02 mmol). The reaction mixture is heated to 70° C. for 1 h in a microwave. The reaction mixture is concentrated under reduced pressure and the residue is dissolved in methanol and filtered. The filtrate is concentrated under reduced pressure and the crude material is purified by preparative HPLC (neutral method) to afford 137 mg of compound 11 as a clear oil. Yield: 34%, LC-MS (LC Method b): retention time: 1.25 min, m/z 396 [M+H].

The following intermediates are made according to the above procedure.

TABLE 5

| Intermediate No. | Structure | Yield [%] | LC Method and Retention time [min] | m/z [M + H] |
|---|---|---|---|---|
| XXXX (compound 11) | 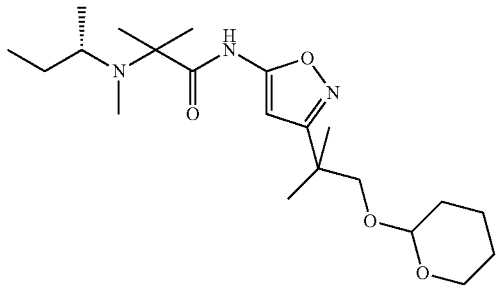 | 33 | LC Method b: 1.25 | 396 |
| XLI | 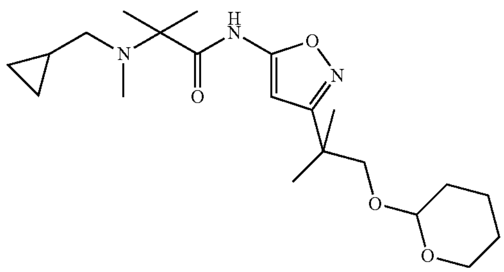 | 59 | LC Method b: 1.22 | 394 |
| XLII | 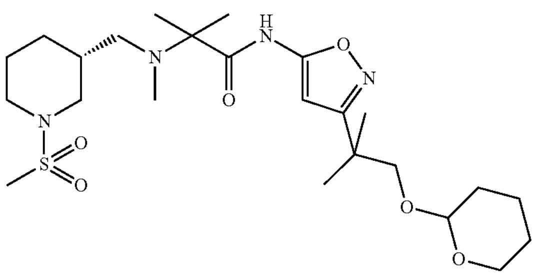 | 60 | LC Method b: 1.63 | 515 |
| XLIII | 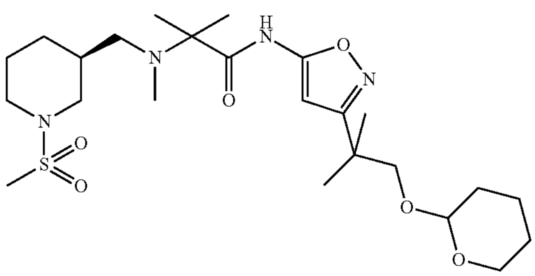 | 52 | LC Method b: 1.63 | 515 |
| XLIV | 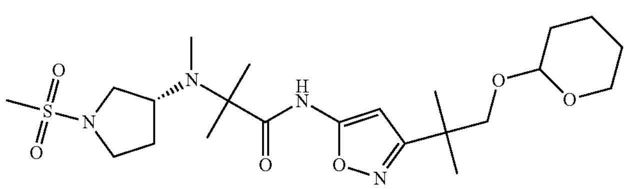 | 36 | LC Method b: 1.94 | 485 [M − H] |
| XLV | 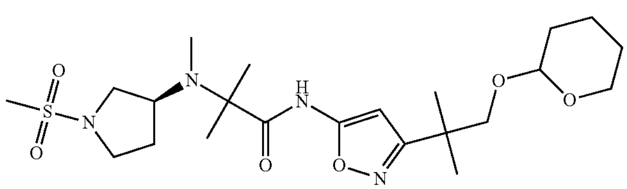 | 49 | LC Method b: 1.94 | 485 [M − H] |

Step 3: Synthesis of Example 54

To a solution of compound 11 (137 mg, 0.34 mmol) in DCM/methanol (1/1, 10 mL) is added polymer-supported tosic acid (MP-TsOH (65), loading 3.3 mmol/g, 0.31 g). The mixture is shaken on an orbital-shaker at room temperature for 18 h. The resin is isolated by filtration and washed with DCM. The product is then released from the resin with 2M solution of ammonia in methanol. Concentration of the basic filtrate affords 88 mg of example 54. Yield: 63%, LC-MS (LC Method a): retention time: 2.35 min, m/z 312 [M+H].

Compounds listed in Table IV under method I are made following this procedure with the following modifications to be noted:

Example 54, 55, 84, 85 are converted into the hydrochloride salt by stirring in the presence of hydrogen chloride in diethyl ether (2M, 1 mL) at room temperature, followed by concentration under reduced pressure.

Method J

Synthesis of Example 27

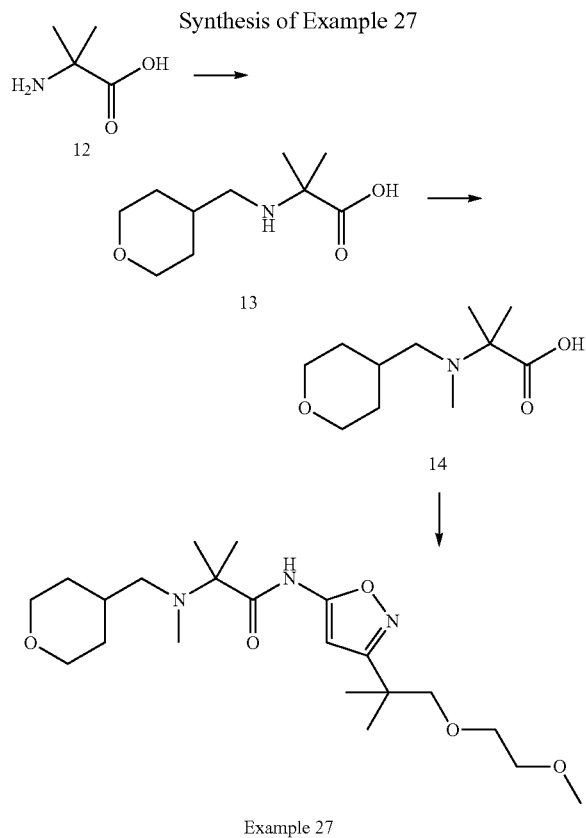

Step 1: Synthesis of Compound 13

A high pressure vessel on the HEL 100 system containing compound 12 (2.5 g; 24.244 mmol) and tetrahydro-pyran-4-carbaldehyde (5.05 mL; 48.487 mmol) is added palladium hydroxide, 20% on carbon, wet (3.405 g; 10 mol %; 2.424 mmol) and 50 mL of ethanol. The reaction is subjected to 400 psi $H_2$ at 50° C. for 40 h. After this time, the reaction is cooled to room temperature and filtered through Celite®. The Celite® is rinsed with methanol and water.

The combined filtrates are concentrated and slurried in dichloromethane, then filtered to afford compound 13 as a white solid (3.95 g; 81%), LC-MS (LC Method h): retention time 0.32 min, m/z 202 [M+H]$^+$

Step 2: Synthesis of Compound 14

A high pressure vessel on the HEL 100 system containing compound 13 (1 g; 4.969 mmol) and formaldehyde, 37% in water (0.74 mL; 9.937 mmol) is added palladium hydroxide, 20% on carbon, wet (0.698 g; 10 mol %; 0.497 mmol) and 30 mL of ethanol. The reaction is subjected to 400 psi $H_2$ at 100° C. for 27.5 h. After this time, the reaction is cooled to room temperature and filtered through Celite®. The Celite® is rinsed with methanol and water. The combined filtrates are concentrated to afford compound 14 as a colorless oil (1.364 g; quantitative), LC-MS (LC Method h): retention time 0.32 min, m/z 216 [M+H]$^+$

Step 3: Synthesis of Example 27

To a vial containing compound 14 (0.2 g; 0.929 mmol) is added O-(7-azabenzotriazol-1-yl)-N,N,N',N'-tetramethyluronium hexafluorophosphate (0.530 g; 1.394 mmol) and N,N-diisopropylethylamine (0.579 mL; 3.252 mmol). The solution is stirred at room temperature for 30 minutes. To a vial containing 3-[2-(2-methoxy-ethoxy)-1,1-dimethylethyl]-isoxazol-5-ylamine (0.199 g; 0.929 mmol) is added N,N-dimethylformamide (2 mL) and sodium hydride (0.093 g; 2.323 mmol) at 0° C. To this solution is added the activated ester. Once addition is complete, the cold bath is removed and the reaction warmed to room temperature and stirred for 1 h. The reaction is quenched with methanol/water and concentrated under reduced pressure. Purification is done by reverse phase HPLC to afford example 27 (0.107 g; 28%), LC-MS (LC Method c): retention time 0.97 min, m/z 412 [M+H]$^+$.

Compounds listed in Table IV under method J are made following this procedure with the following modifications to be noted: for example 26, 28, and 32 TBTU (O-(benzotriazol-1-yl)-N,N,N',N'-tetramethyluronium tetrafluoroborate) is used as the coupling reagent instead of HATU as described in step 3.

Compounds listed in Table IV under method J are made following this procedure

The following intermediates are made according to the above procedure.

TABLE 6

| Intermediate No. | Structure | Yield [%] | LC Method and Retention time [min] | m/z [M + H] |
|---|---|---|---|---|
| XLVI | 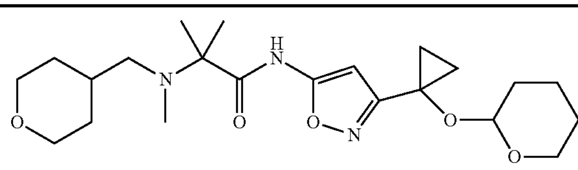 | crude | LC Method d: 1.08 | 422 |

TABLE 6-continued

| Intermediate No. | Structure | Yield [%] | LC Method and Retention time [min] | m/z [M + H] |
| --- | --- | --- | --- | --- |
| XLVII | 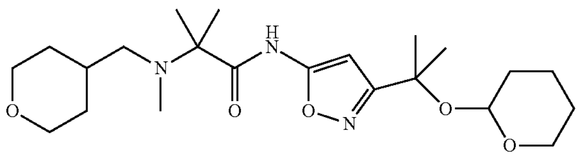 | crude | LC Method d: 1.08 | 424 |
| XLVIII | 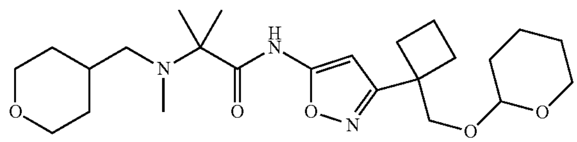 | 31 | LC Method c:1.08 | 450 |
| XLIX | 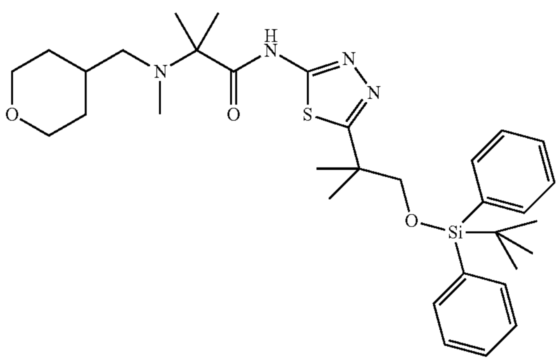 | 23 | LC Method c:, 1.70 | 609 |
| L | 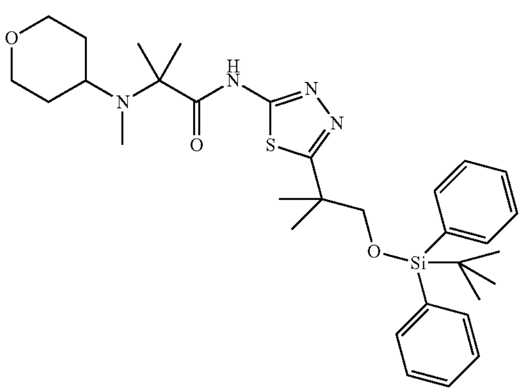 | 23 | LC Method c:, 1.80 | 595 |

Method J1

Same as Method C step 3.

Compounds listed in Table IV under Method J1 are made following this procedure.

Method J2

Synthesis of Example 30

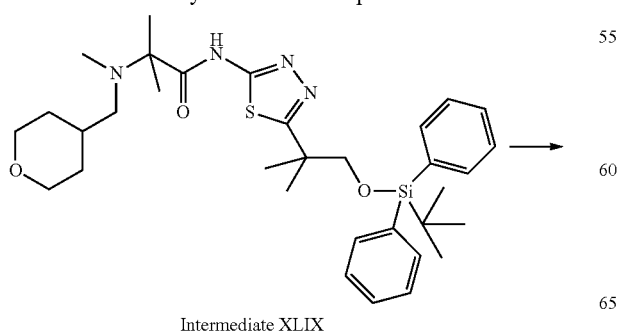

Intermediate XLIX

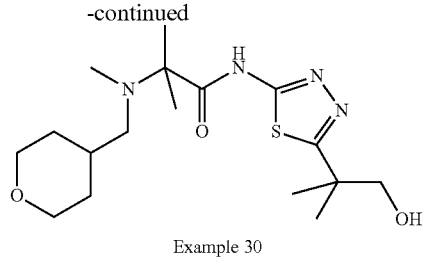

Example 30

Intermediate XLIX (0.127 g; 0.209 mmol) is diluted with 3 mL methanol and HF pyridine complex (0.130 ml; 1.045 mmol; 70%) is added. The reaction is heated at 45° C. in a sealed tube for 7 days adding aliquots of HF pyridine complex on a daily basis. Concentrated and purified by preparative HPLC. Pooled product fractions and concentrated. Diluted in methanol and passed through a cartridge containing MP- Carbonate resin to neutralize molecule from trifluoroacetic acid contained in HPLC mobile phase to afford example 30 (0.024 g; 31.1%); LC-MS (LC method c): retention time 0.40 min, m/z 371 [M+H$^+$]

Compounds listed in Table IV under Method J2 are made following this procedure.

Method K

Synthesis of Example 38

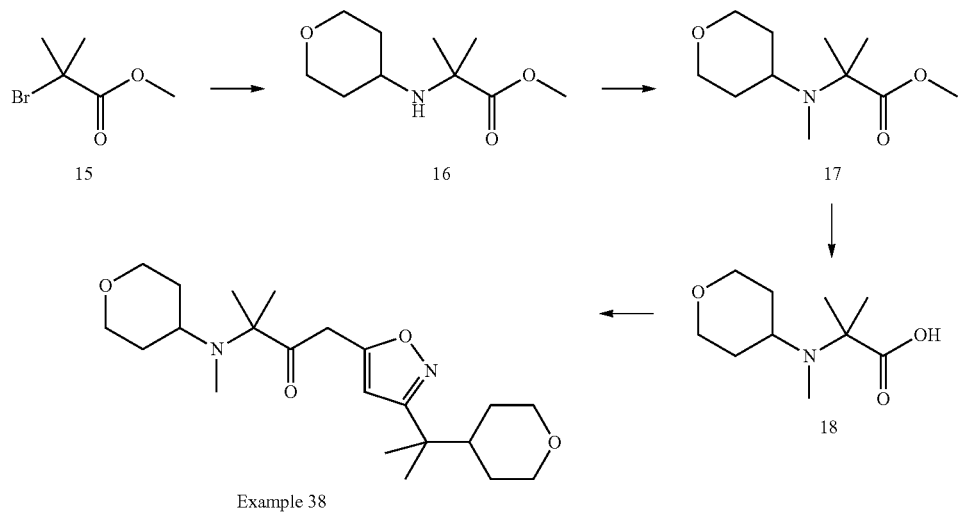

Example 38 bath for 16 hours, After this time, the reaction mixture is cooled to room temperature and methyl 2-bromoisobutyrate (1.6 mL, 12.4 mmol) and potassium iodode (184.5 mg, 1.11 mmol) are added and the reaction mixture is heated in 90° C. oil bath for 18 hours. After this time, the reaction mixture is cooled to room temperature and filtered through a glass funnel and the solid is washed with acetonitrile. The filtrate is concentrated under reduced pressure. Purification of the residue by flash chromatography on silica gel using ethyl acetate/heptane provides compound 16 (36%), LC-MS (LC method d): retention time: 0.27 min, m/z 202 [M+H$^+$].

The following intermediates are made following the above procedure:

TABLE 7

| Intermdediate No. | Structure | Yield [%] | LC Method and Retention time [min] | m/z [M + H] |
|---|---|---|---|---|
| LI (compound 16) | 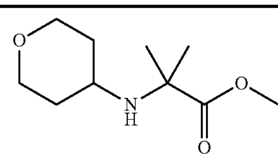 | 36 | LC Method d: 0.27 | 202 |
| LII | 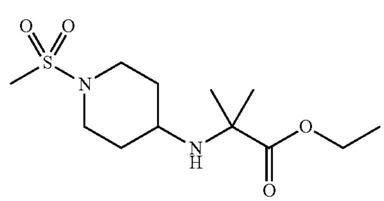 | 31 | LC Method d: 0.60 | 293 |

Notes: starting material for intermediate I is ethyl 2-bromoisobutyrate.

Step 1: Synthesis of Compound 16

Compound 15 (6.4 mL, 49.4 mmol) is dissolved in 100 mL of acetonitrile under nitrogen and potassium iodide (739 mg, 4.5 mmol) is added followed by the addition of potassium carbonate (13.7 g, 98.9 mmol) and 4-aminotetrahydropyran (5 g, 49.4 mmol). The reaction mixture is heated in 90° C. oil Step 2: Synthesis of Compound 17

Methyl iodide (2.5 mL, 39.9 mmol) is added dropwise to a mixture of compound 16 (4.38 g, 17.7 mmol) and potassium carbonate (10.94 g, 79.1 mmol) in 74 mL of DMF. The reaction mixture is stirred at room temperature for 18 hours. After this time, methyl iodide (1 mL, 16 mmol) is added and the reaction mixture is stirred at room temperature for 65 hours. After this time, the reaction mixture is filtered and the solid is washed with ethyl acetate. The filtrate is concentrated under reduced pressure. Purification of the residue by flash chromatography on silica gel using ethyl acetate/heptane provides compound 17 (78%), LC-MS (Method d): retention time: 0.27 min, m/z 216 [M+H⁺].

The following intermediates are made following the above procedure:

TABLE 8

| Intermediate No. | Structure | Yield [%] | LC Method and Retention time [min] | m/z [M + H] |
|---|---|---|---|---|
| LIII (compoun 17) | 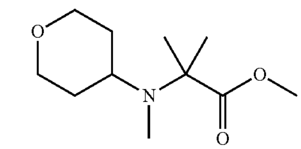 | 78 | LC Method d: 0.27 | 216 |
| LIV | 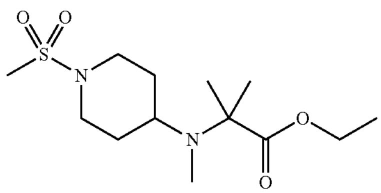 | 88 | LC Method d: 1.27 | 307 |

Step 3: Synthesis of Compound 18

Compound 17 (3.24 g, 13.8 mmol) is dissolved in 14 mL of methanol in a pressure tube and sodium hydroxide aqueous solution (4N, 13.8 mL, 55.3 mmol) is added and the reaction mixture is heated in 80° C. oil bath for 3 hours. After this time, the reaction mixture is concentrated under reduced pressure and the residue is neutralized to pH ~7 by adding 1N HCl aqueous solution. The resulting solution is diluted with acetonitrile and dried in lyophilizer for 18 hours. After this time, the solid is suspended in acetone and filtered. The filtrate is concentrated under reduced pressure to afford compound 18 (100%), LC-MS (LC Method d): retention time: 0.29 min, m/z 202 [M+H⁺].

The following intermediates are made following the above procedure:

Step 4: Synthesis of Example 38

To a vial containing compound 18 (142 mg, 0.707 mmol) in 1 mL of DMF is added O-(benzotriazol-1-yl)-N,N,N',N'-tetramethyluronium tetrafluoroborate (272 mg, 0.848 mmol) and diisopropylethylamine (0.27 mL, 1.55 mmol). The mixture is stirred at room temperature for 1 hour. To a vial containing compound 25 (149 mg, 0.707 mmol) in 1.2 mL of DMF is added sodium hydride in mineral oil (60%, 62 mg, 1.55 mmol). The mixture is stirred at room temperature for 15 minutes. To this solution is added dropwise the activated ester. The reaction mixture is stirred at room temperature for 1.5 hours. After this time, the reaction mixture is concentrated under reduce pressure to remove the solvent. The residue is quenched with saturated sodium bicarbonate aqueous solution and extracted with ethyl acetate twice. The organics are combined and washed with brine, dried over Na₂SO₄, filtered and concentrated under reduced pressure. Purification of the residue by flash chromatography on silica gel using methanol/methylene chloride provides example 38 (17%), LC-MS (LC method d): retention time 1.03 min, m/z 394 [M+H⁺].

Compounds listed in Table IV under Method K are made following this procedure.

Also, the following intermediates are made following this procedure.

TABLE 9

| Intermediate No. | Structure | Yield [%] | LC Method and Retention time [min] | m/z [M + H] |
|---|---|---|---|---|
| LV compoun 18) | 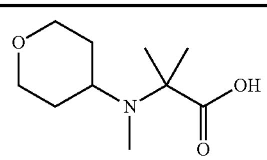 | 100 | LC Method d: 0.29 | 202 |
| LVI | 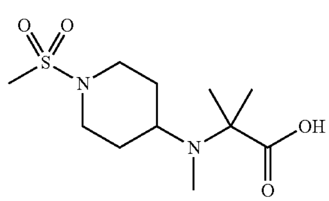 | 33 | LC Method d: 0.32 | 279 |

TABLE 10

| Intermediate No. | Structure | Yield [%] | LC Method and Retention time [min] | m/z [M + H] |
|---|---|---|---|---|
| LVII | 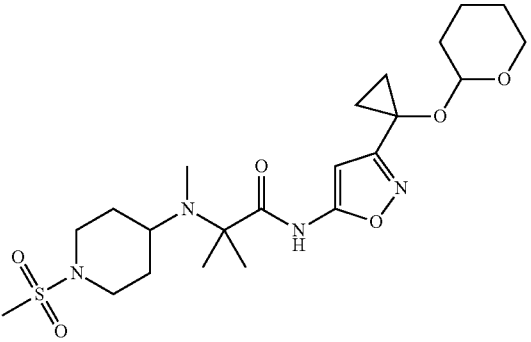 | 45 | LC Method f: 1.28 | 485 |
| LVIII | 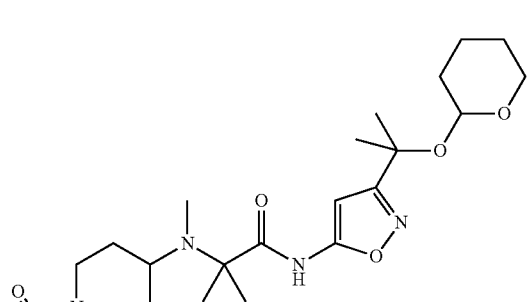 | quantitative | LC Method c:, 1.12 | 487 |

Method K1

Same as Method C step 3.

Compounds listed in Table IV under Method K1 are made following this procedure.

Method L

Synthesis of Example 36

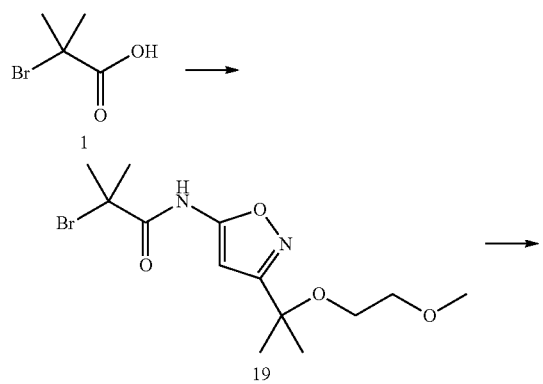

Example 36

Step 1: Synthesis of Compound 19

To a pressure vessel containing compound 1 (1.25 g, 7.49 mmol) under nitrogen is added thionyl chloride (2.5 mL, 34.5 mmol) and catalytic amount of DMF, The pressure vessel is sealed and heated to 70° C. where it is maintained for 2 hours. After this time, the reaction mixture is cooled to room temperature and diluted with dichloromethane and the acid chloride solution is concentrated in vacuo until ~1 mL left and this process is repeated twice. The crude acid chloride is used without further purification. The crude acid chloride is diluted with 2 mL of toluene and added to the vial containing 3-[1-(2-Methoxy-ethoxy)-1-methyl-ethyl]-isoxazol-5-ylamine (1 g, 5.0 mmol) and N,N-diisopropylethylamine (4.35 mL, 24.98 mmol) in 10 mL of toluene and the reaction mixture is heated at 55° C. for 18 hours. After this time, the reaction mixture is quenched with saturated sodium bicarbonate aqueous solution and extracted with ethyl acetate twice. The organics are combined and washed with brine, dried over Na₂SO₄, filtered and concentrated under reduced pressure. Purification of the residue by flash chromatography on silica gel using ethyl acetate/heptane provides compound 19 (52%), m/z 350 [M+H⁺]

Compounds listed in intermediate table below are made following this procedure with the following modifications to be noted: for LXII reaction with thionyl chloride is heated at 80° C., for LXIV-LXV reaction with thionyl chloride is heated at 60° C.

TABLE 11

| Intermediate No. | Structure | Yield [%] | LC Method and Retention time [min] | m/z [M/M + 2H] |
|---|---|---|---|---|
| LIX(compoun 19) | 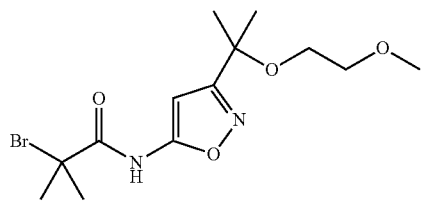 | 52 | LC Method d: 1.30 | 349/351 |
| LX | 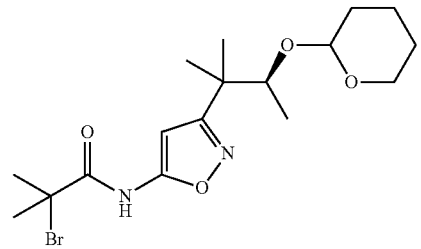 | 64 | LC Method d: 1.49 | 319/321 [M-THP/M-THP + 2H] |
| LXI | 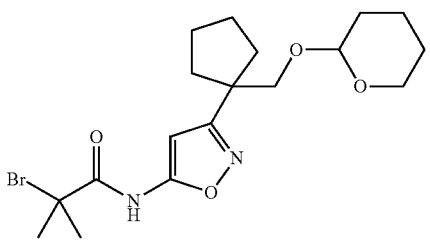 | 58 | LC Method d: 1.52 | 331/333 [M-THP/M-THP + 2H] |
| LXII | 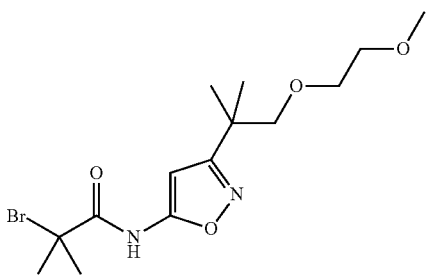 | 13 | LC Method c: 1.28 | 363/365 |
| LXIII | 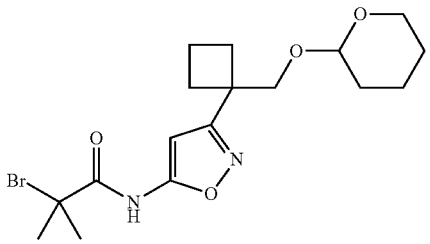 | 38 | LC Method c: 1.49 | 317/319 [M-THP/M-THP + 2H] |

TABLE 11-continued

| Intermediate No. | Structure | Yield [%] | LC Method and Retention time [min] | m/z [M/M + 2H] |
|---|---|---|---|---|
| LXIV | 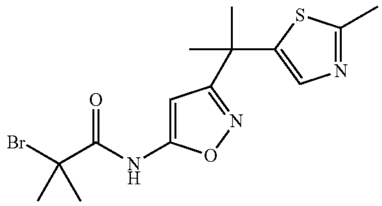 | 31 | LC Method c: 1.29 | 372/374 |
| LXV | 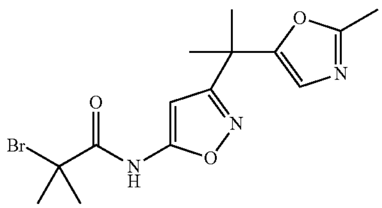 | 32 | LC Method c: 1.23 | 356/358 |
| LXVI | 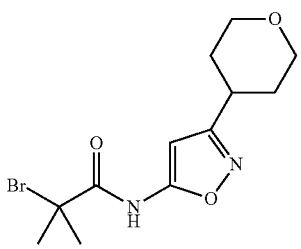 | 90 | LC Method d: 1.25 | 317/319 [M/M + 2H] |

Step 2: Synthesis of Example 36

Sodium hydride in mineral oil (60%, 61.8 mg, 1.55 mmol) is suspended in 2 mL of THF and the solution of 4,4,4-Trifluoro-butylamine (81.9 mg, 0.64 mmol) in 1 mL of THF is added and the mixture is stirred at room temperature for 5 minutes under nitrogen before dropwise adding the solution of compound 19 (180 mg, 0.52 mmol) in 1.5 mL of THF. The reaction mixture is stirred at room temperature for 18 hours. After this time, the reaction mixture is quenched with saturated sodium bicarbonate aqueous solution and extracted with ethyl acetate twice. The organics are combined and washed with brine, dried over $Na_2SO_4$, filtered and concentrated under reduced pressure. Purification of the residue by flash chromatography on silica gel using ethyl acetate/heptane provides example 36 (47%), LC-MS (LC Method d): retention time 1.05 min, m/z 396 [M+H$^+$].

Compounds listed in Table IV under Method L are made following this procedure, with the exception of example 14, 31, and 76 for which the last step is run according to Method B Step 2, and the crude is purified by prep HPLC or silica gel chromatography. Further for example 15 in Table IV NaH (4 equivalents) in mineral oil is used.

Also, the following intermediates are made following this procedure, with the exception that for intermediates LXVII-LXXI NaH (4 equivalents) in mineral oil is used.

TABLE 12

| Intermediate No. | Structure | Yield [%] | LC Method and Retention time [min] | m/z [M + H] |
|---|---|---|---|---|
| LXVII | 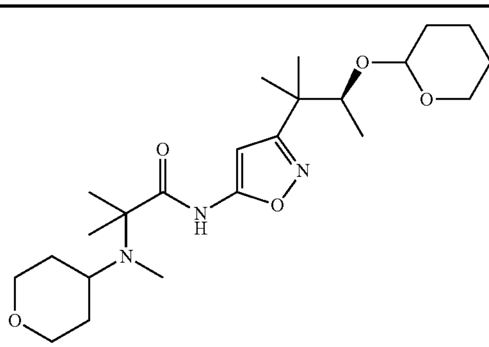 | 27 | LC Method d: 1.15 | 438 |

TABLE 12-continued

| Intermediate No. | Structure | Yield [%] | LC Method and Retention time [min] | m/z [M + H] |
|---|---|---|---|---|
| LXVIII | 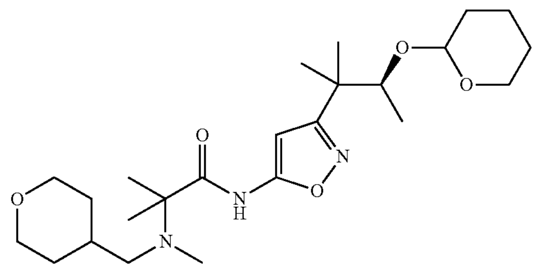 | 42 | LC Method d: 1.14 | 452 |
| LXIX | 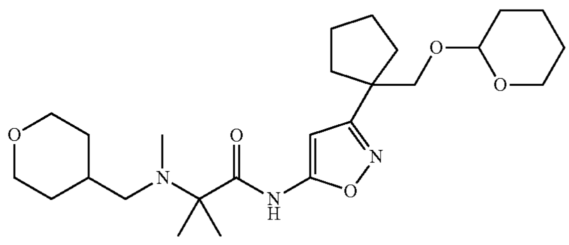 | 34 | LC Method d: 1.17 | 464 |
| LXX | 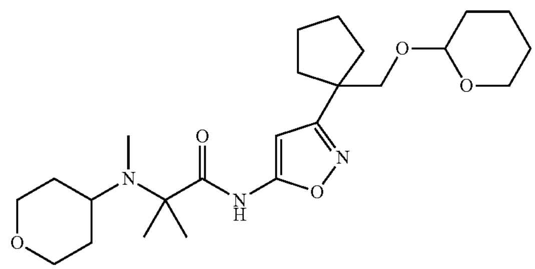 | 16 | LC Method d: 1.16 | 450 |
| LXXI | 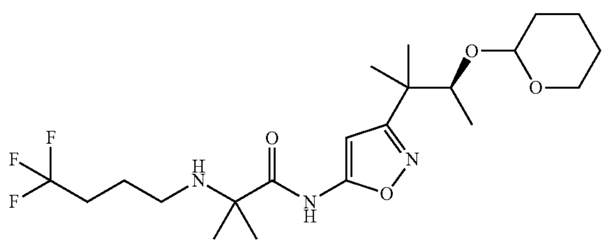 | 65 | LC Method d: 1.20 | 450 |
| LXXII | 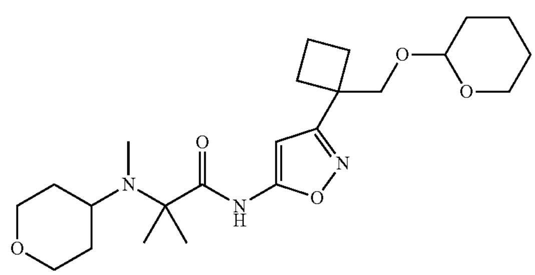 | quantitative | LC Method d: 1.32 | 436 |
| LXXIII | 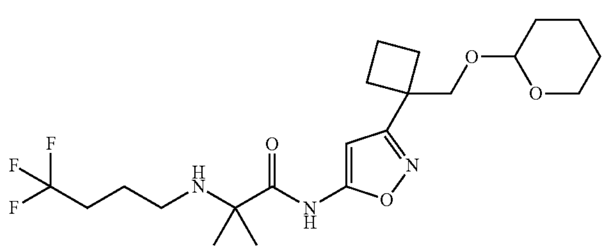 | 61 | LC Method c 1.14 | 448 |

Method L1

Same as Method C step 3.

Compounds listed in Table IV under Method L1 are made following this procedure.

Method M

Synthesis of Example 22

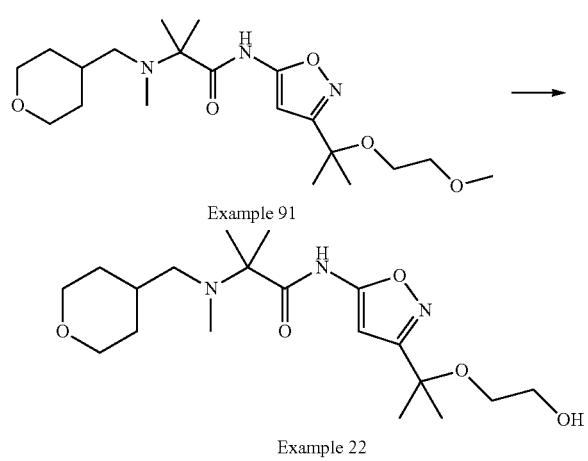

Example 91

Example 22

Aluminum chloride (188 mg, 1.4 mmol) is added to a cooled (0° C.) suspension of example 91 (33 mg, 0.083 mmol) in ethanethiol (1 mL, 13.5 mmol). The reaction mixture is stirred at room temperature for 65 hours. Aluminum chloride (100 mg, 0.74 mmol) is added and the reaction mixture is stirred at room temperature for 24 hours. After this time, the reaction mixture is quenched with 20 mL of water and 5 drops of concentrated hydrochloric acid aqueous solution and the mixture is stirred at room temperature for 1 hour. The mixture is extracted with ethyl acetate and the layers are separated. The aqueous layer is basicified to pH ~14 by adding 4N sodium hydroxide aqueous solution and the resulting mixture is extracted with ethyl acetate twice. The organics are combined and washed with brine, dried over Na$_2$SO$_4$, filtered and concentrated under reduced pressure. Purification of the residue by flash chromatography on silica gel using methanol/methylene chloride provides example 22 (88%), m/z 384 [M+H$^+$].

Compounds listed in Table IV under Method M are made following this procedure.

Method N

Synthesis of Example 90

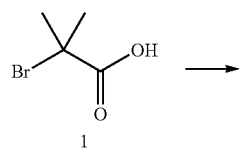

1

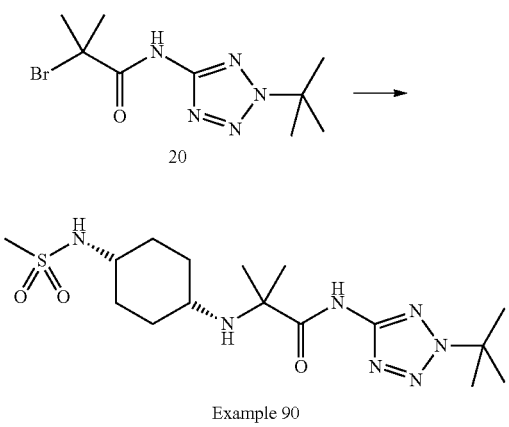

20

Example 90

Step 1: Synthesis of Compound 20

To a flask containing compound 1 (11.8 g, 71 mmol) in MeCN (500 mL) is added EDC.HCl (37.7 g, 212 mmol) and DMAP (8.6 mg, 71 mmol) at room temperature. 2-tert-butyl-2H-tetrazol-5-ylamine (10 g, 71 mmol) is added and the reaction mixture is stirred at room temperature for 24 h. Water (50 mL) is added and extracted with ethyl acetate (3×250 mL). The combined organic layers are dried (Na$_2$SO$_4$) and the solvent is concentrated under reduced pressure. The crude material is purified by column chromatography (silica, eluent: heptanes, 0-50% ethyl acetate) to afford 9.4 g of compound 20. Yield: 45%, LC-MS (LC Method b): retention time: 1.71 min, m/z 290/292 [M+H].

Step 2: Synthesis of Example 90

N-(cis-4-Aminocyclohexyl)methanesulfonamide (0.22 g, 1.14 mmol) and compound 20 (0.32 g, 1.14 mmol) are charged into a pressure tube. The reaction mixture is heated to 150° C. for 20 min until the solids are melted. After cooling to room temperature, the residue is dissolved in ethyl acetate (10 mL) and washed with saturated NaHCO$_3$ solution (10 mL). The aqueous layer is extracted with ethyl acetate (2×20 mL) and the combined organic layers are dried over Na$_2$SO$_4$ and filtered. The filtrate is concentrated under reduced pressure and the residue is purified by preparative LC (neutral method) followed by column chromatography (silica, eluent: heptanes, 0-60% ethyl acetate) to afford 6 mg of example 90. Yield: 1.3%, LC-MS (LC Method a): retention time: 2.36 min, m/z 402 [M+H].

Synthesis of Compound 25

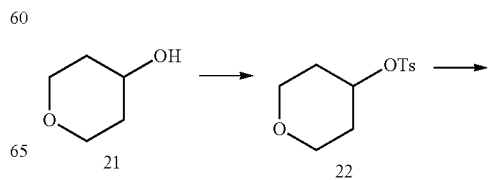

21   22

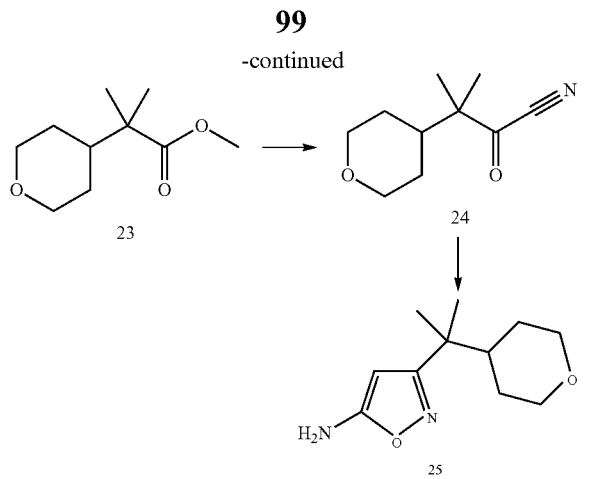

Step 1: Synthesis of Compound 22

Paratoluenesulfonyl chloride (300.0 g, 1.58 mol) is added to a solution of compound 21 (100.0 g, 0.98 mol) in 800.0 mL of pyridine at 0° C. After stifling the reaction mixture at room temperature for 14 hours, it is pored into an ice solution of 6N HCl. Some precipitate is formed that is filtered and triturated with hexanes. After drying under vacuum the crude compound 22 is used without further purification in the next step.
$^1$H NMR (400 MHz, chloroform-d) δ ppm 1.70-1.89 (4H, m), 2.45 (3H, s), 3.44-3.50 (2H, m), 3.86 (2H, p), 4.70 (1H, m), 7.33 (2H, d, 8.4 Hz), 7.79 (2H, d, 8.0 Hz).

Step 2: Synthesis of Compound 23 n-BuLi (1.6M solution in hexane, 122.5 mL) is added slowly to a stirred solution of DIPA in dry THF (150 mL) at −78° C. After stifling the solution for 1 h at −78° C., Isobutyric acid methyl ester (10.0 g, 98.0 mmol) is added slowly and stirred for 3 h at −78° C. Compound 22 (25.1 g, 98.0 mmol) is dissolved in THF and added to the reaction mixture that is stirred for 1 h at −78° C. and 14 h at room temperature. The reaction mixture is quenched with water and extracted with ethyl acetate. The organic layer is washed with water and brine, dried over anhy. Na$_2$SO$_4$, filtered and concentrated under vacuum. The crude is purified by silica flash column chromatography (30% Ethyl actetate in heptane), to afford 7.0 g of the compound 23 as a pale yellow oil. Yield: 38%.
$^1$H NMR (400 MHz, chloroform-d) δ ppm 1.13 (6H, s), 1.38-1.45 (4H, m), 1.78-1.85 (1H, m), 3.33-3.40 (2H, m), 3.66 (3H, s), 3.98 (2H, dd, 2.8 Hz).

Step 3: Synthesis of Compound 24

A solution of compound 23 (6.0 g, 32.2 mmol) in CH$_3$CN (2.2 mL) is added to a stirred suspension of NaH (2.1 g, 48.3 mmol) in toluene (60.0 mL) at 80° C. and the reaction mixture is further maintained at reflux temperature for 14 h. The reaction mixture is cooled to room temperature; water is added and extracted with EtOAc (3 times). The aqueous layer is acidified with 2N aq. HCl solution and extracted with EtOAc. The combined EtOAc layers are washed with brine, dried over anhy. Na$_2$SO$_4$, filtered and concentrated under reduced pressure to afford the compound 24 (4.2 g) that is used in the next step without further purification.

Step 4: Synthesis of Compound 25

Hydroxylamine sulphate (2.95 g, 17.9 mmol) and solid NaOH (2.16 g, 53.77 mmol) are added to a stirring solution of compound 24 (3.5 g, 17.9 mmol) in water (35.0 mL), and the resultant reaction mixture is stirred at reflux for 14 h. The reaction mixture is cooled to room temperature and then extracted with EtOAc (3 times). The combined EtOAc layers are washed with water, brine, dried over anhy. Na$_2$SO$_4$, filtered and concentrated under reduced pressure. The crude is purified by silica gel column chromatography (50% ethyla cetate in heptane) to afford 1.4 g of compound 25. Yield: 37%, LC-MS (Method d): retention time: 1.09 min, m/z 211 [M+H].

Synthesis of Compound 28

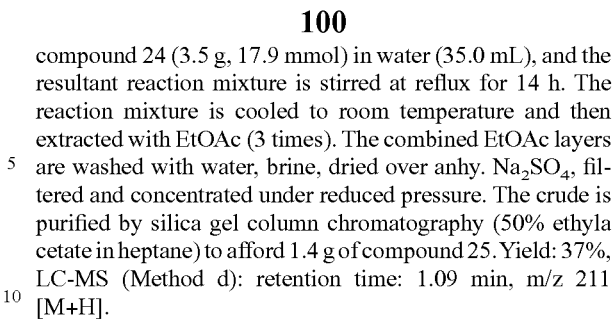

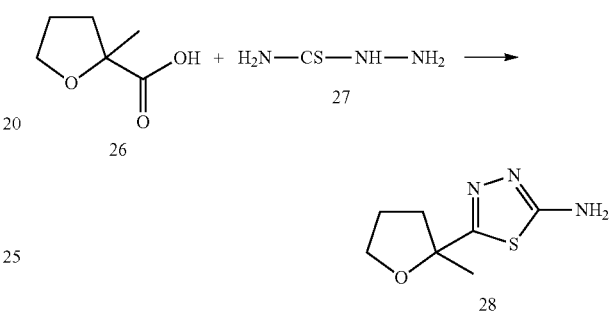

A solution of compound 26 and compound 27 in conc. HCl is heated at 100° C. for 3 h. The reaction mixture is quenched with aq NH$_3$ solution and extracted with ethyl acetate (twice). The combined EtOAc fraction is washed with brine solution, dried over anh. Na$_2$SO$_4$, filtered and concentrated under reduced pressure. The crude is purified by silica gel column chromatography (5% methanol in dichloromethane) to afford 0.85 g of compound 28. Yield: 30%, LC-MS (Method d): retention time: 0.74 min, m/z 186 [M+H].

Method O

Synthesis of Example 58

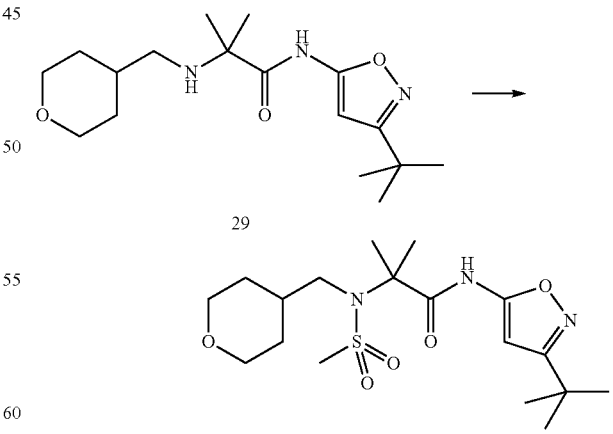

A microwave reaction vessel is charged with a solution of compound 29 (120 mg, 0.37 mmol, prepared according to WO2009105509, Boehringer Ingelheim) in THF (2 mL) and NaH (60% dispersion in mineral oil, 15 mg, 0.37 mmol) is added. The mixture is stirred at room temperature for 5 min and methanesulfonylchloride (28 μL, 0.37 mmol) is added. The reaction mixture is heated in a microwave to 70° C. for 1 h. The mixture is diluted with ethyl acetate (20 mL) and washed with 1N aqueous HCl solution (2×3 mL) and brine (3 mL). The organic layer is dried (Na₂SO₄), filtered and concentrated under reduced pressure. The residue is dissolved in ethyl acetate and heptanes are added. The resulting white precipitate is isolated by filtration and dried under reduced pressure to afford 18 mg of example 58. Yield: 12%; LC-MS (Method a): retention time: 3.92 min, m/z 402 [M+H].

Compounds listed in Table IV under Method O are made following this procedure.

TABLE IV

Examples

| Example # | Structure | LC Method | retention time [min] | m/z [M + H+] | Method |
|---|---|---|---|---|---|
| 1 | 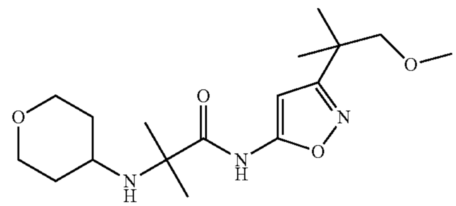 | a | 2.40 | 340 | A |
| 2 | 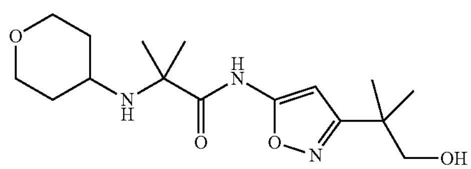 | a | 2.16 | 326 | B |
| 3 | 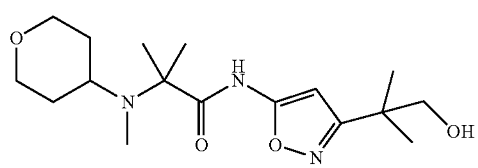 | a | 2.17 | 340 | C |
| 4 | 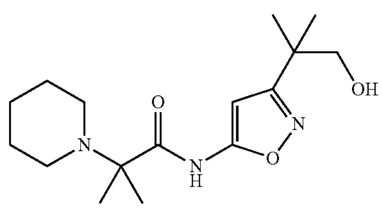 | a | 2.19 | 310 | C |
| 5 | 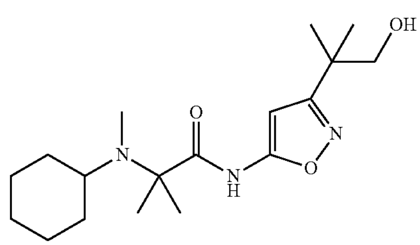 | a | 2.56 | 338 | C |
| 6 | 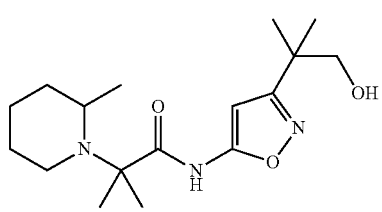 | a | 2.35 | 324 | D |

TABLE IV-continued

Examples

| Example # | Structure | LC Method | retention time [min] | m/z [M + H+] | Method |
|---|---|---|---|---|---|
| 7 | 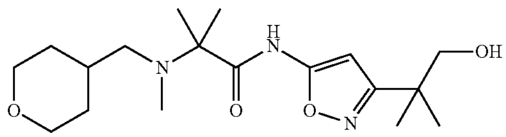 | c | 0.71 | 354 | C |
| 8 | 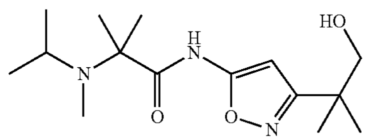 | f | 0.82 | 298 | C |
| 9 | 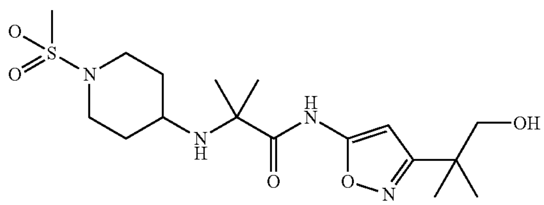 | c | 0.50 | 403 | C |
| 10 | 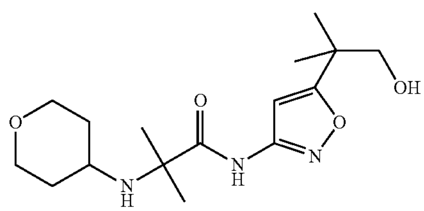 | a | 2.14 | 326 | E |
| 11 | 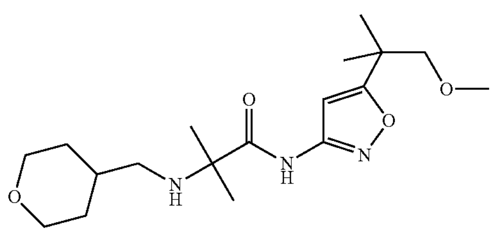 | a | 2.60 | 354 | A |
| 12 | 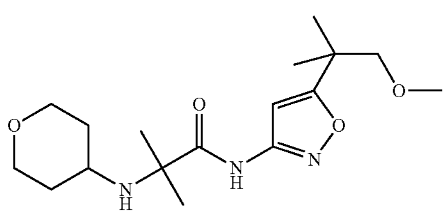 | a | 2.50 | 340 | A |
| 13 | 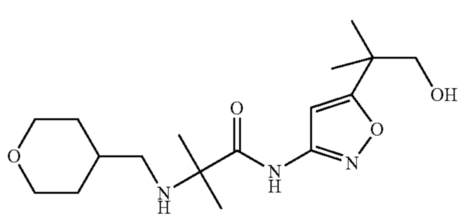 | a | 2.25 | 340 | E |

TABLE IV-continued

Examples

| Example # | Structure | LC Method | retention time [min] | m/z [M + H+] | Method |
|---|---|---|---|---|---|
| 14 | 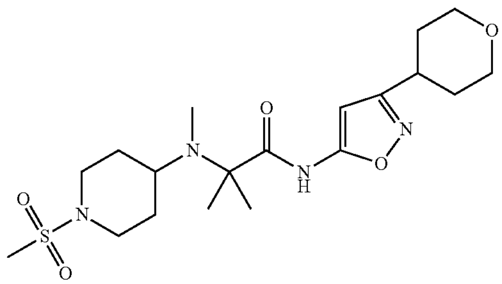 | g | 4.00 | 429 | L |
| 15 | 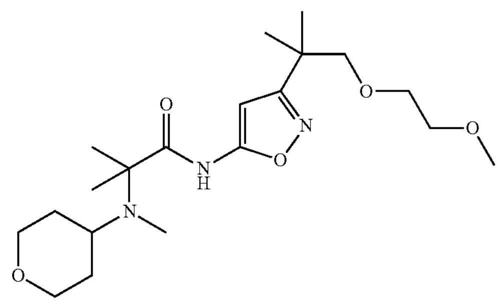 | c | 0.92 | 398 | L |
| 16 | 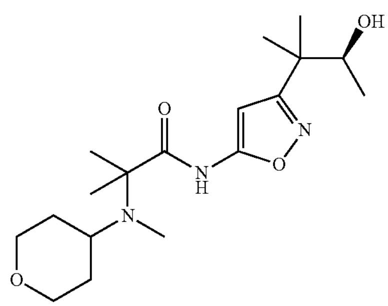 | d | 0.86 | 354 | L1 |
| 17 | 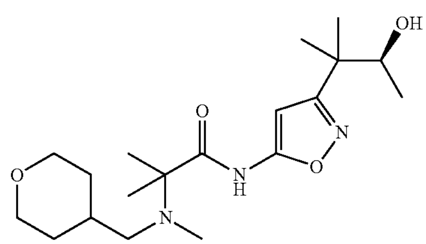 | f | 0.94 | 368 | L1 |
| 18 | 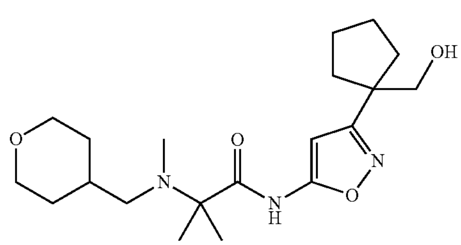 | d | 0.97 | 380 | L1 |

TABLE IV-continued

Examples

| Example # | Structure | LC Method | retention time [min] | m/z [M + H+] | Method |
|---|---|---|---|---|---|
| 19 | 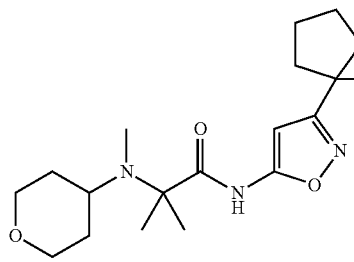 | d | 0.93 | 366 | L1 |
| 20 | 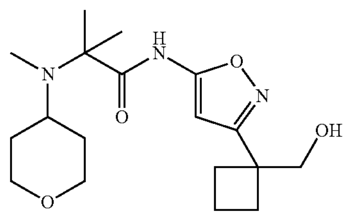 | c | 0.33 | 352 | L1 |
| 21 | 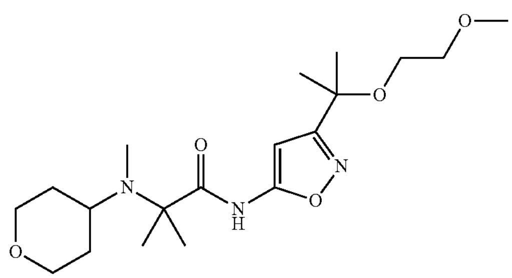 | d | 1.08 | 384 | L |
| 22 | 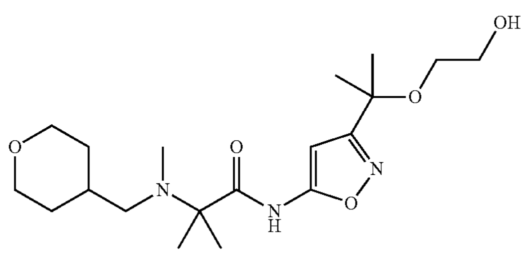 | d | 0.90 | 384 | M |
| 23 | 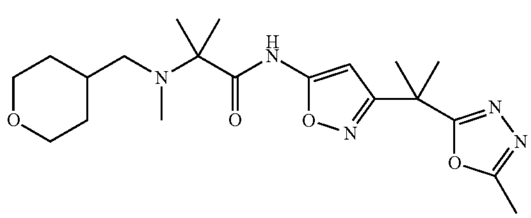 | g | 3.96 | 406 | J |
| 24 | 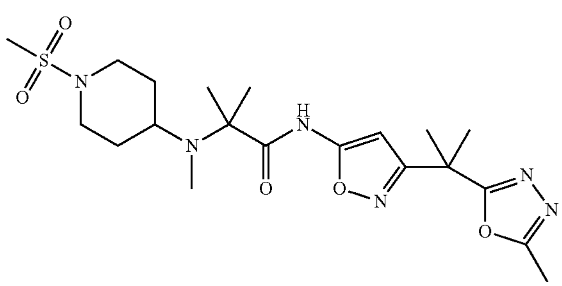 | g | 3.40 | 469 | K |

TABLE IV-continued

Examples

| Example # | Structure | LC Method | retention time [min] | m/z [M + H+] | Method |
|---|---|---|---|---|---|
| 25 | 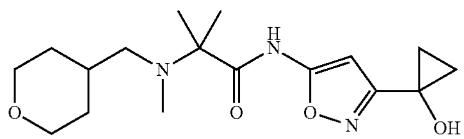 | d | 0.77 | 338 | J |
| 26 | 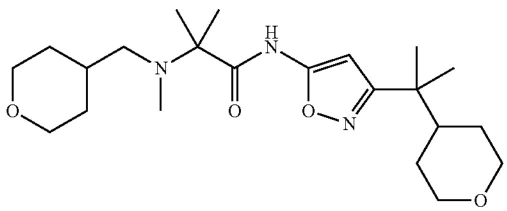 | d | 1.04 | 408 | J |
| 27 | 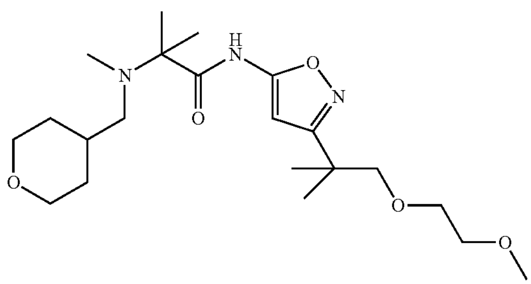 | c | 0.97 | 412 | J |
| 28 | 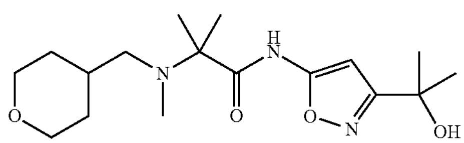 | d | 0.73 | 340 | J |
| 29 | 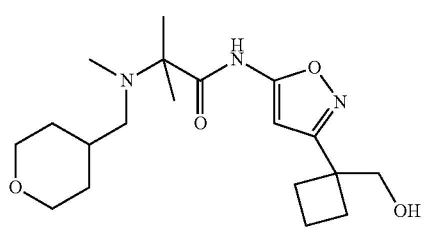 | c | 0.77 | 366 | J1 |
| 30 | 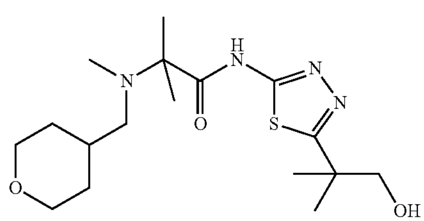 | c | 0.40 | 371 | J2 |
| 31 | 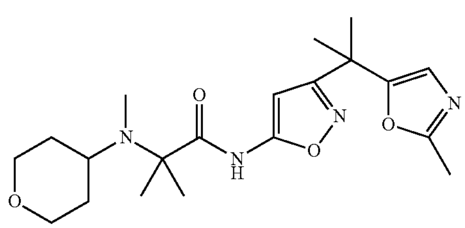 | g | 4.03 | 391.7 | L |

TABLE IV-continued

Examples

| Example # | Structure | LC Method | retention time [min] | m/z [M + H+] | Method |
|---|---|---|---|---|---|
| 32 | 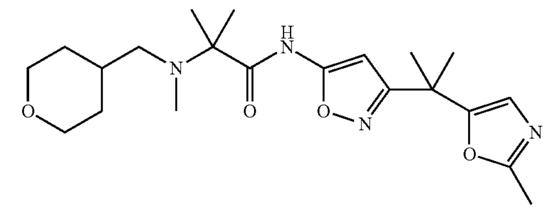 | g | 4.19 | 405 | J |
| 33 | 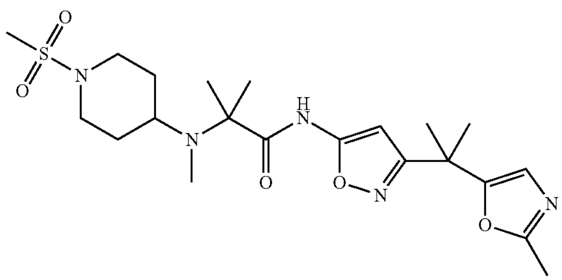 | g | 4.28 | 468 | K |
| 34 | 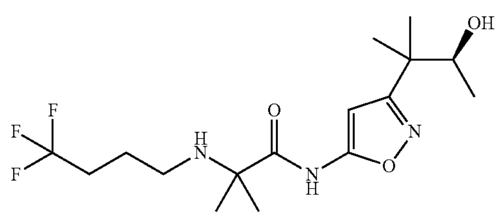 | d | 0.98 | 366 | L1 |
| 35 | 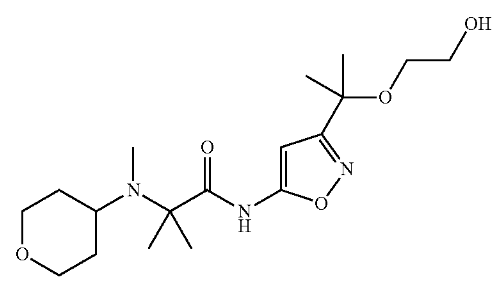 | d | 0.83 | 370 | M |
| 36 | 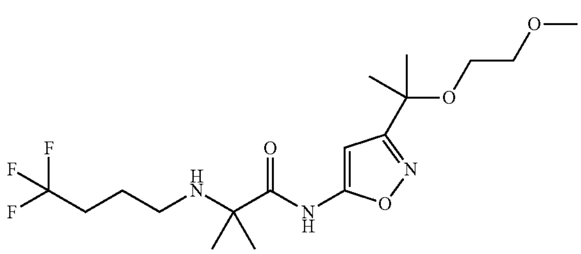 | d | 1.05 | 396 | L |
| 37 | 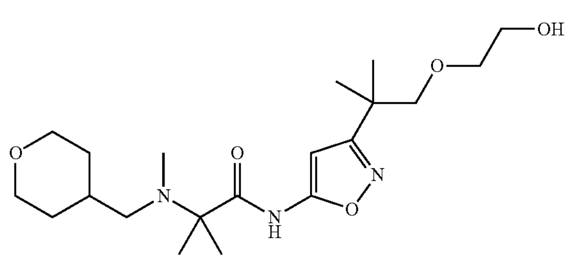 | c | 0.74 | 398 | M |

TABLE IV-continued

Examples

| Example # | Structure | LC Method | retention time [min] | m/z [M + H+] | Method |
|---|---|---|---|---|---|
| 38 | 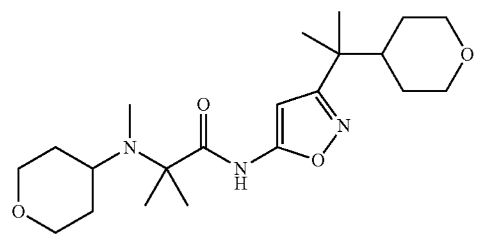 | d | 1.03 | 394 | K |
| 39 | 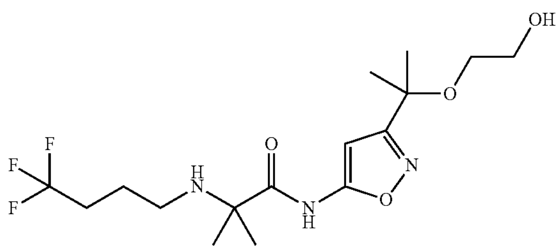 | d | 0.94 | 382 | M |
| 40 | 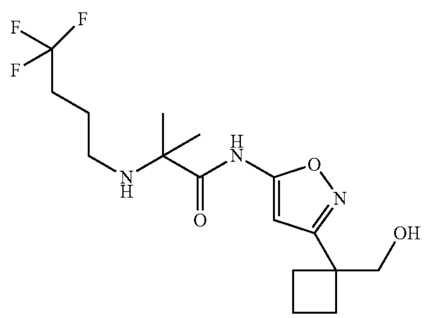 | c | 0.85 | 364 | L1 |
| 41 | 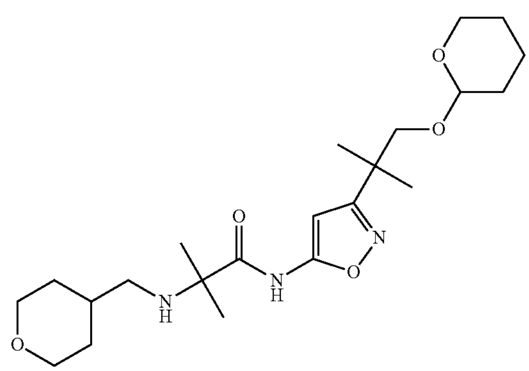 | a | 2.89 | 424 | C |
| 42 | 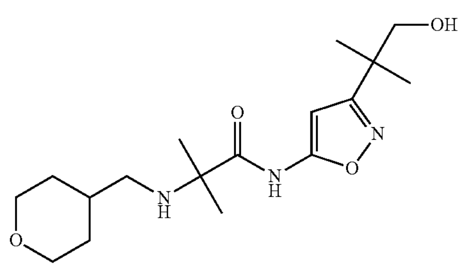 | a | 2.14 | 340 | C |

TABLE IV-continued
Examples
| Example # | Structure | LC Method | retention time [min] | m/z [M + H+] | Method |
|---|---|---|---|---|---|
| 43 | 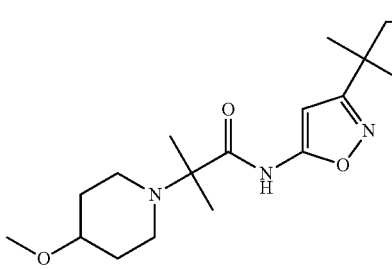 | a | 2.36 | 340 | C |
| 44 | 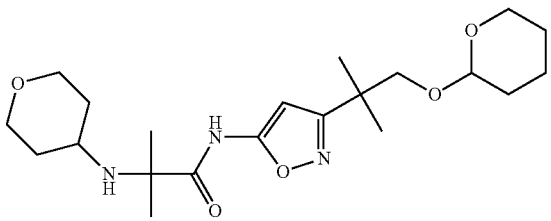 | a | 2.74 | 410 | C |
| 45 | 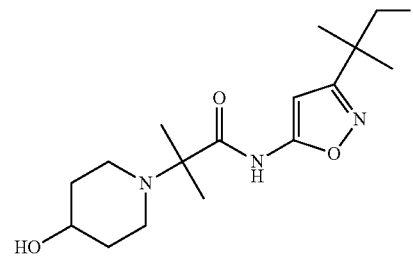 | a | 1.87 | 326 | C |
| 46 | 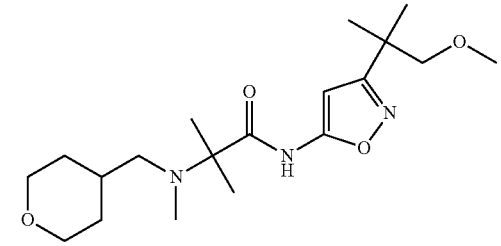 | a | 2.60 | 368 | F |
| 47 | 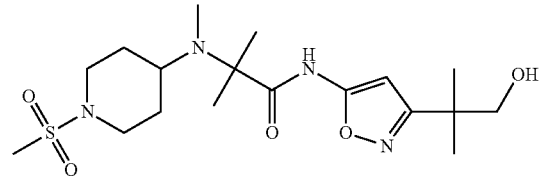 | a | 2.25 | 417 | C |
| 48 | 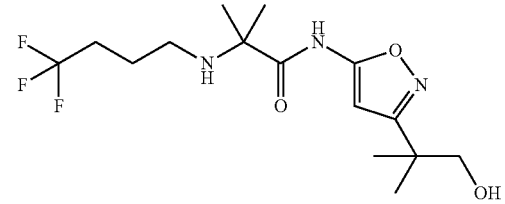 | a | 2.51 | 352 | C |

TABLE IV-continued
Examples
| Example # | Structure | LC Method | retention time [min] | m/z [M + H+] | Method |
|---|---|---|---|---|---|
| 49 | 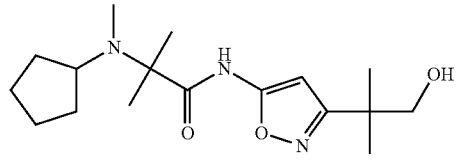 | a | 2.33 | 324 | C |
| 50 | 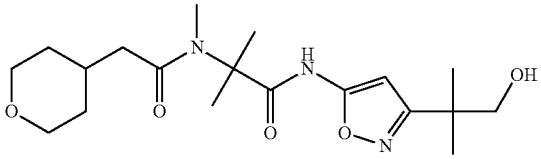 | a | 3.06 | 382 | G |
| 51 | 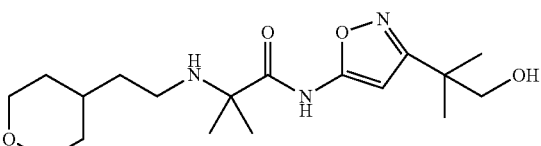 | a | 2.30 | 354 | C |
| 52 | 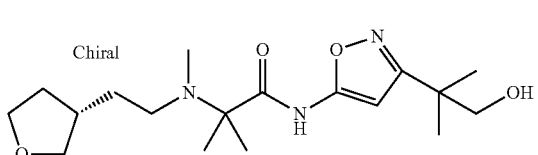 | a | 2.19 | 354 | H |
| 53 | 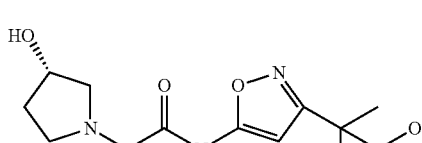 | a | 1.86 | 312 | C |
| 54 | 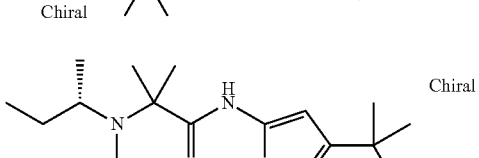 | a | 2.35 | 312 | I |
| 55 | 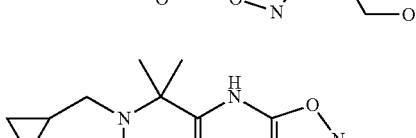 | a | 2.24 | 310 | I |
| 56 | 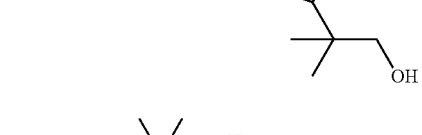 | a | 2.18 | 296 | C |

TABLE IV-continued

| Example # | Structure | | LC Method | retention time [min] | m/z [M + H+] | Method |
|---|---|---|---|---|---|---|
| 57 | 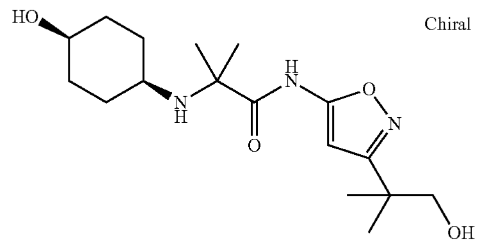 | Chiral | a | 2.13 | 340 | C |
| 58 | 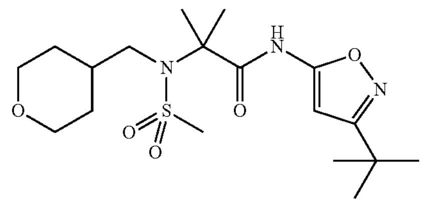 | | a | 3.92 | 402 | O |
| 59 | 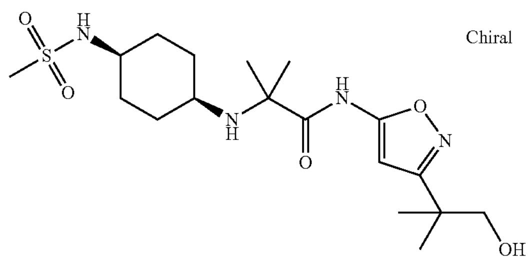 | Chiral | a | 2.19 | 417 | C |
| 60 | 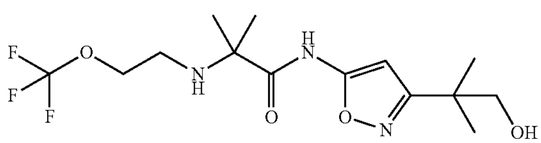 | | a | 2.42 | 354 | C |
| 61 | 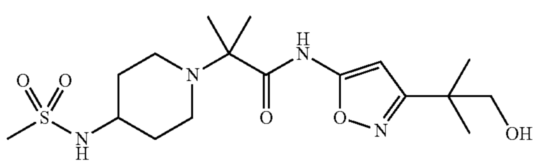 | | a | 2.09 | 403 | C |
| 62 | 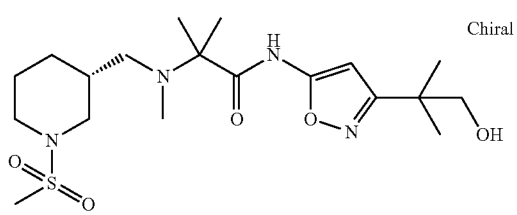 | Chiral | a | 2.48 | 431 | I |
| 63 | 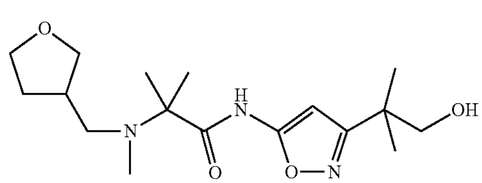 | | a | 2.08 | 340 | C |

TABLE IV-continued

Examples

| Example # | Structure | LC Method | retention time [min] | m/z [M + H+] | Method |
|---|---|---|---|---|---|
| 64 | 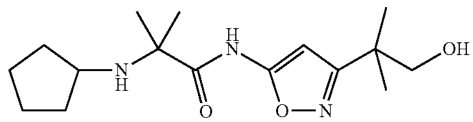 | a | 2.41 | 310 | C |
| 65 | 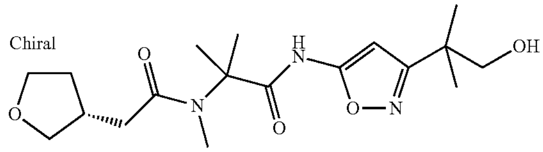 | a | 2.90 | 368 | G |
| 66 | 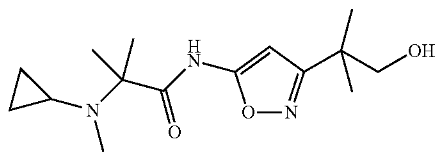 | a | 2.26 | 296 | C |
| 67 | 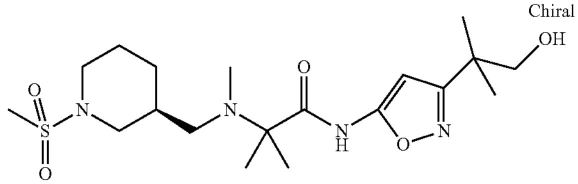 | a | 2.49 | 431 | I |
| 68 | 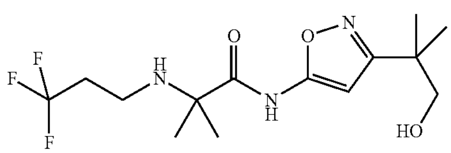 | a | 2.38 | 338 | C |
| 69 | 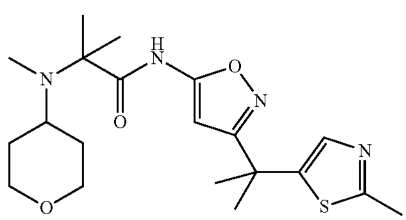 | c | 0.96 | 407 | J |
| 70 | 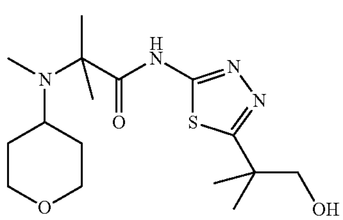 | c | 0.52 | 357 | J2 |
| 71 | 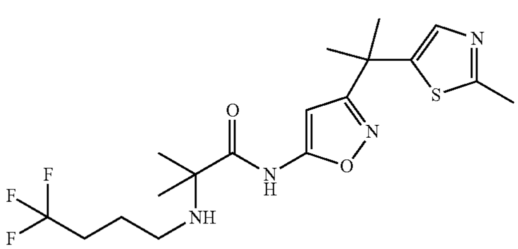 | c | 0.97 | 419 | L |

TABLE IV-continued

Examples

| Example # | Structure | LC Method | retention time [min] | m/z [M + H+] | Method |
|---|---|---|---|---|---|
| 72 | 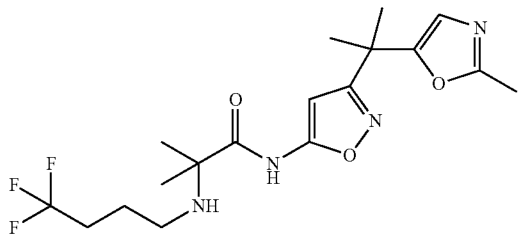 | c | 0.92 | 403 | L |
| 73 | 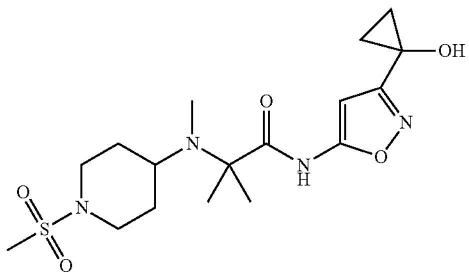 | f | 0.85 | 401 | K1 |
| 74 | 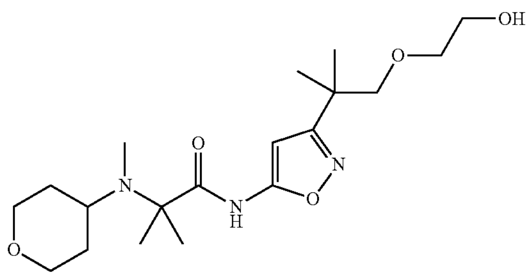 | c | 0.54 | 384 | M |
| 75 | 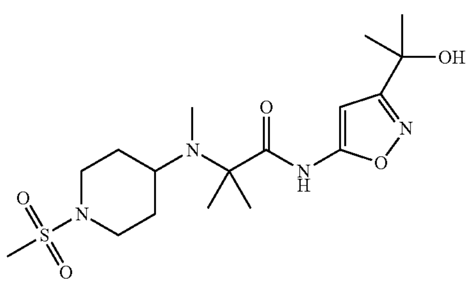 | g | 4.05 | 403 | K1 |
| 76 | 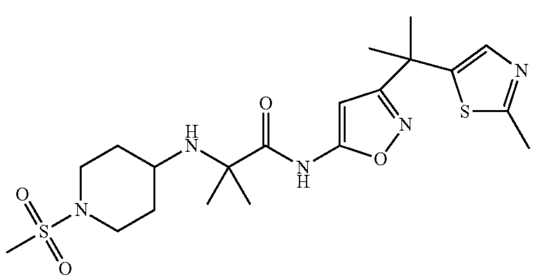 | g | 4.34 | 468 | L |

TABLE IV-continued

Examples

| Example # | Structure | LC Method | retention time [min] | m/z [M + H+] | Method |
|---|---|---|---|---|---|
| 77 | 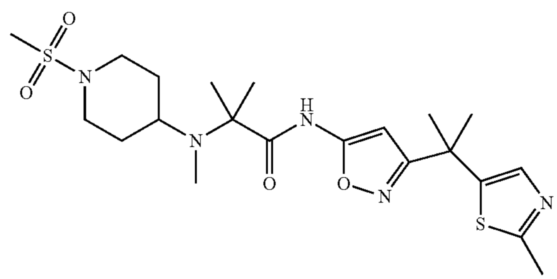 | g | 4.22 | 484 | K |
| 78 | 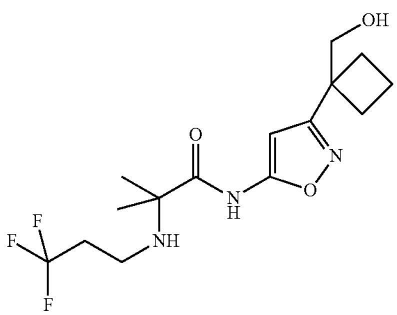 | c | 0.84 | 350 | L |
| 79 | 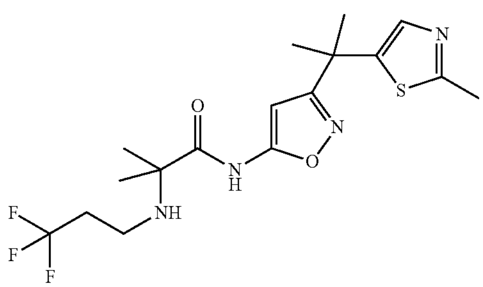 | c | 1.09 | 405 | L |
| 80 | 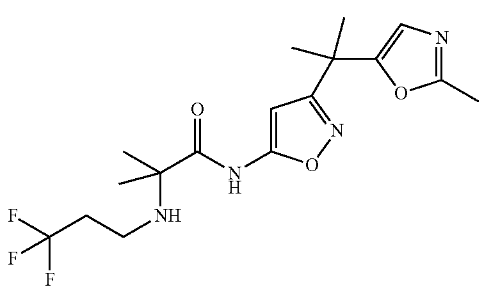 | c | 1.02 | 389 | L |
| 81 | 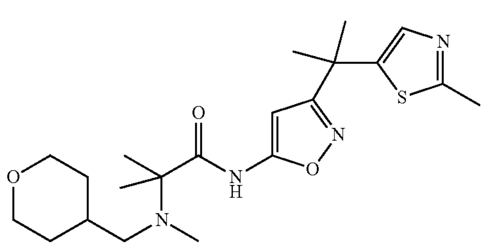 | c | 1.01 | 421 | J |

TABLE IV-continued

Examples

| Example # | Structure | LC Method | retention time [min] | m/z [M + H+] | Method |
|---|---|---|---|---|---|
| 82 | 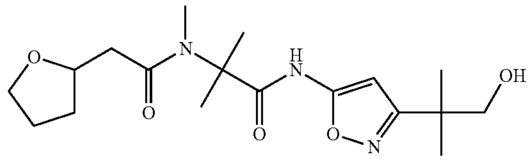 | a | 3.09 | 368 | G |
| 83 | 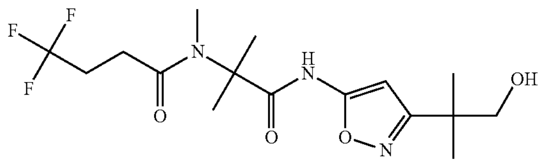 | a | 3.51 | 380 | G |
| 84 | (Chiral) | a | 2.90 | 403 | I |
| 85 | (Chiral) | a | 2.86 | 403 | I |
| 86 | (Chiral) | a | 2.36 | 356 | C |
| 87 | (Chiral) | a | 2.38 | 3.56 | C |
| 88 | 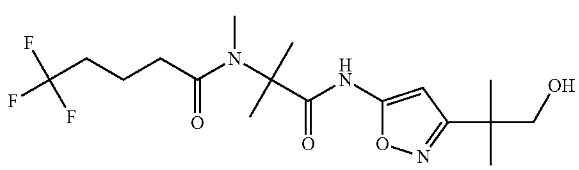 | a | 3.66 | 394 | G |
| 89 | 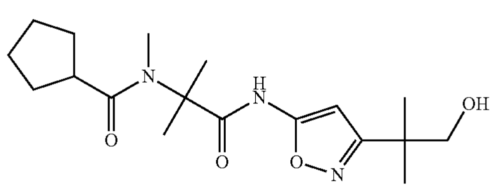 | a | 3.51 | 352 | G |

TABLE IV-continued

Examples

| Example # | Structure | LC Method | retention time [min] | m/z [M + H+] | Method |
|---|---|---|---|---|---|
| 90 | Chiral | a | 2.36 | 402 | N |
| 91 | 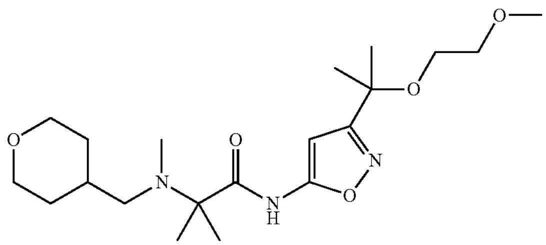 | d | 0.96 | 398 | L |

Analytical Methods
LC Method a:
HPLC-MS Equipment
HPLC pumps: Agilent G1312A
Autoinjectors: CTC PAL HTC Detectors:
MS: Waters ZQ
UV: Waters 2996 photodiode array
Ancillary: Waters 2420 evaporative light scattering detectors (ELS)

| Higher specification method designed for medicinal chemistry sample screening | | | |
|---|---|---|---|
| Column | Waters Atlantis dC18 2.1 × 100 mm, 3 μm column | Flow rate | 0.6 ml/min |
| Mobile Phase | A, 0.1% Formic acid (water) B, 0.1% Formic acid (CH$_3$CN) | Injection Vol | 3 μl |
| Temp. | 40° C. | Detection | 215 nm (nominal) |
| Gradient | Time (mins) | % organic | |
| | 0.00 | 5 | See FIG. 1/2 |
| | 5.00 | 100 | |
| | 5.40 | 100 | |
| | 5.42 | 5 | |
| | 7.00 | 5 | |

LC Method b:
HPLC-MS equipment:
Shimadzu LCMS-2010EV system: (MS, pump, PDA)
Autoinjectors CTC PAL HTS autosampler

Figure 2:
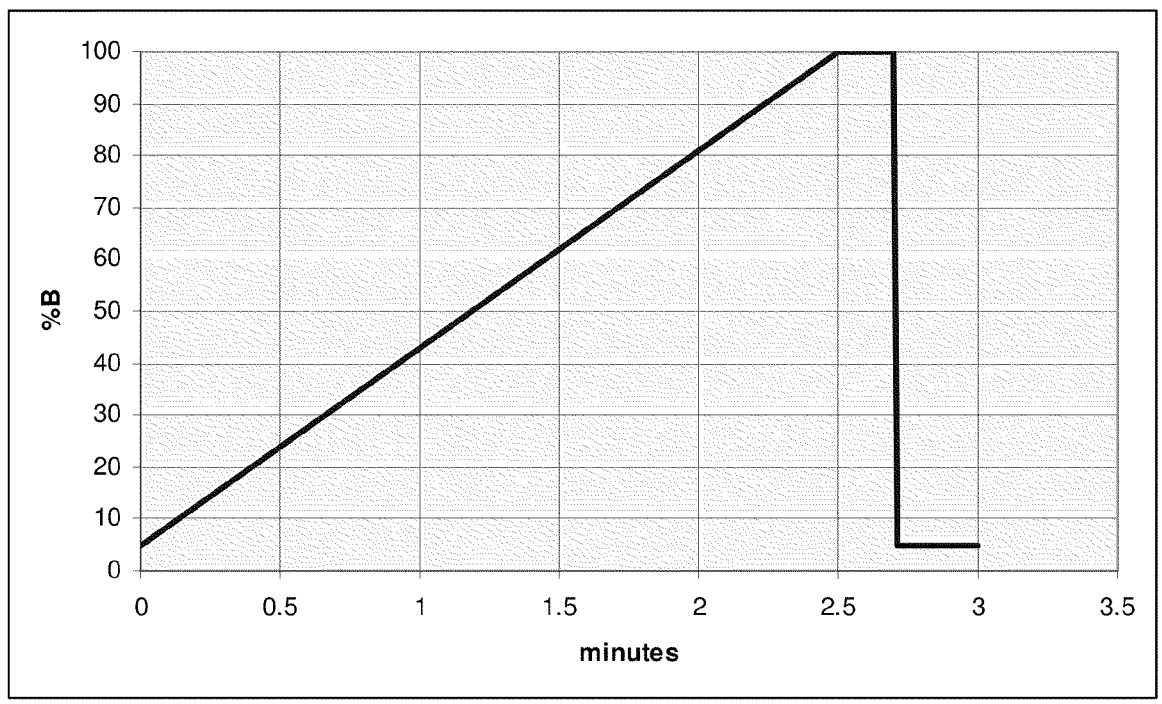
FIG. 2: Flow rate graph time vs % organic (B) using HPLC-MS equipment.

| Standard method for routine high throughput analysis | | | |
|---|---|---|---|
| Column | Atlantis dC18 2.1 × 50 mm, 5 μm | Flow rate | 1 ml/min |
| Mobile Phase | A, Formic acid (aq) 0.1% B, Formic acid (CH$_3$CN) 0.1% | Injection Vol | 3 μl |
| Temp. | 40° C. | Detection | 215 nm (nominal) |
| Gradient | Time (mins) | % organic | |
| | 0.00 | 5 | See. FIG. 2/2 |
| | 2.50 | 100 | |
| | 2.70 | 100 | |
| | 2.71 | 5 | |
| | 3.00 | 5 | |

| LC Method c: Column: Agilent SB-C18 1.81 μm 3 × 50 mm, 1.5 mL/min flow rate | | |
|---|---|---|
| Time (min) | Water (0.1% FA) | Acetonitrile (0.1% FA) |
| 0 | 88 | 12 |
| 0.25 | 70 | 30 |
| 0.3 | 60 | 40 |
| 1.19 | 5 | 95 |
| 1.75 | 0 | 100 |

| LC Method d: Column: Agilent SB-AQ 1.81 μm 3 × 50 mm, 1.5 mL/min flow rate | | |
|---|---|---|
| Time (min) | Water (0.1% FA) | Acetonitrile (0.1% FA) |
| 0 | 95 | 5 |
| 0.25 | 50 | 50 |
| 0.3 | 30 | 70 |
| 1.3 | 10 | 90 |
| 1.7 | 0 | 100 |

| LC Method e: Column: BEH C18, 1.7 μm 2.1 × 50 mm, 0.8 mL/min flow rate | | |
|---|---|---|
| Time (min) | Water (0.05% FA) | Acetonitrile (0.05% FA) |
| 0 | 90 | 10 |
| 1.19 | 5 | 95 |
| 1.7 | 5 | 95 |

| LC Method f: Column: Agilent Zorbax C18 SB 3.5 μm 4.6 × 30 mm, 2.5 mL/min flow rate | | |
|---|---|---|
| Time (min) | Water (0.1% FA) | Acetonitrile (0.1% FA) |
| 0 | 95 | 5 |
| 1.7 | 5 | 95 |
| 2.0 | 5 | 95 |
| 2.1 | 95 | 5 |
| 2.3 | 95 | 5 |

| LC Method g: Column: Agilent Zorbax Eclipse XDB-C8 5.0 μm 4.6 × 150 mm, 1.5 mL/min flow rate | | |
|---|---|---|
| Time (min) | Water (0.1% FA) | Acetonitrile (0.1% FA) |
| 0 | 95 | 5 |
| 2.0 | 95 | 5 |
| 7.0 | 10 | 90 |
| 9.0 | 5 | 95 |
| 9.3 | 95 | 5 |
| 10.0 | 95 | 5 |

| LC Method h: Column: Zorbax XDB-C8 4.6 × 50 mm 3.5 μm, 2 mL/min flow rate | | |
|---|---|---|
| Time (min) | Water (0.05% FA) | Acetonitrile (0.05% FA) |
| 0.0 | 95 | 5 |
| 3.5 | 40 | 60 |
| 4.5 | 5 | 95 |
| 4.7 | 95 | 5 |
| 5.0 | 95 | 5 |

Assessment of Biological Properties

The biological properties of the compounds of the formula I are assessed using the assays described below.

A. Human CB1 and CB2 Receptor Binding:

Experimental Method:

CB2 membranes are purchased and made from HEK293 EBNA cells stably transfected with human CB2 receptor cDNA (Perkin Elmer Life and Analytical Sciences). CB1 membranes are isolated from HEK cells stably co-transfected with human CB1 receptor and Gα16 cDNA's. The membrane preparation is bound to scintillation beads (Ysi-Poly-L-lysine SPA beads, GE Healthcare) for 4 hours at room temperature in assay buffer containing 50 mM Tris, pH 7.5, 2.5 mM EDTA, 5 mM $MgCl_2$, 0.8% fatty acid free Bovine Serum Albumin. Unbound membrane is removed by washing in assay buffer. Membrane-bead mixture is added to 96-well assay plates in the amounts of 15 ug membrane per well (CB2) or 2.5 ug per well (CB1) and 1 mg SPA bead per well. Compounds are added to the membrane-bead mixture in dose-response concentrations ranging from $1 \times 10^{-5}$ M to $1 \times 10^{-10}$ M with 0.25% DMSO, final. The competition reaction is initiated with the addition of $^3$H-CP55940 (Perkin Elmer Life and Analytical Sciences) at a final concentration of 1.5 nM (CB2) or 2.5 nM (CB1). The reaction is incubated at room temperature for 18 hours and read on TopCount NXT plate reader. Total and non-specific binding is determined in the absence and presence of 1.25 uM Win 55212 (Sigma). IC50 values for each compound are calculated as the concentration of compound that inhibits the specific binding of the radioactively labeled ligand to the receptor by 50% using the XLFit 4.1 four parameter logistic model. IC50 values are converted to inhibition constant (Ki) values using Cheng-Prusoff equation.

B. CB2R Mediated Modulation of cAMP Synthesis:

Compounds of the invention are evaluated for their CB2 agonist or inverse agonistic activity in accordance with the following experimental method. Compounds which are shown to bind to CB2 by the binding assay described above but which are not shown to exhibit CB2R-mediated modulation of cAMP synthesis by this assay are presumed to be CB2 antagonists.

Experimental Method:

CHO cells expressing human CB2R (Euroscreen) are plated at a density of 5000 cells per well in 384 well plates and incubated overnight at 37° C. After removing the media, the cells are treated with test compounds diluted in stimulation buffer containing 1 mM IBMX, 0.25% BSA and 10 uM Forskolin. The assay is incubated for 30 minutes at 37° C. Cells are lysed and the cAMP concentration is measured using DiscoverX-XS cAMP kit, following the manufacturer's protocol. In this setting, agonists will decrease forskolin induced production of cAMP while inverse agonists will further increase forskolin induced production of cAMP. EC50 of agonists are calculated as follows. The maximal amount of cAMP produced by forskolin compared to the level of cAMP inhibited by 1 uM CP55940 is defined as 100%. The EC50 value of each test compound is determined as the concentration at which 50% of the forskolin-stimulated cAMP synthesis is inhibited. Data is analyzed using a four-parameter logistic model. (Model 205 of XLfit 4.0).

C. CB1R Mediated Modulation of cAMP Synthesis:

Compounds of the invention are evaluated for their CB1 agonist or inverse agonistic activity in accordance with the following experimental method. Compounds which are shown to bind to CB1 by the binding assay described above but which are not shown to exhibit CB1R-mediated modulation of cAMP synthesis by this assay are presumed to be CB1 antagonists.

Experimental Method:

CHO cells expressing human CB1R (Euroscreen) are plated at a density of 5000 cells per well in 384 well plates and incubated overnight at 37° C. After removing the media, the cells are treated with test compounds diluted in stimulation buffer containing 1 mM IBMX, 0.25% BSA and 10 uM Forskolin. The assay is incubated for 30 minutes at 37° C. Cells are lysed and the cAMP concentration is measured using DiscoverX-XS cAMP kit, following the manufacturer's protocol. In this setting, agonists will decrease forskolin induced production of cAMP while inverse agonists will further increase forskolin induced production of cAMP. EC50 of agonists are calculated as follows. The maximal amount of cAMP produced by forskolin compared to the level of cAMP inhibited by 1 uM CP55940 is defined as 100%. The EC50 value of each test compound is determined as the concentration at which 50% of the forskolin-stimulated cAMP synthesis is inhibited. Data is analyzed using a four-parameter logistic model. (Model 205 of XLfit 4.0).

Compounds Having Agonist Activity

Through the use of the above described assays compounds are found to exhibit agonist activity and thus to be particularly well suited for the treatment of pain as well as for the treatment of inflammation. Preferred compounds of the invention will have an activity range of CB2 (<500 nM) and CB1 (>20000).

Therapeutic Use

As can be demonstrated by the assays described above, the compounds of the invention are useful in modulating the CB2 receptor function. By virtue of this fact, these compounds have therapeutic use in treating disease-states and conditions mediated by the CB2 receptor function or that would benefit from modulation of the CB2 receptor function.

As the compounds of the invention modulate the CB2 receptor function, they have very useful anti-inflammatory and immune-suppressive activity and they can be used in patients as drugs, particularly in the form of pharmaceutical compositions as set forth below, for the treatment of disease-states and conditions.

As noted before, those compounds which are CB2 agonists can also be employed for the treatment of pain.

The agonist, antagonist and inverse agonist compounds according to the invention can be used in patients as drugs for the treatment of the following disease-states or indications that are accompanied by inflammatory processes:

(i) Lung diseases: e.g. asthma, bronchitis, allergic rhinitis, emphysema, adult respiratory distress syndrome (ARDS), pigeon fancier's disease, farmer's lung, chronic obstructive pulmonary disease (COPD), asthma including allergic asthma (atopic or non-atopic) as well as exercise-induced bronchoconstriction, occupational asthma, viral- or bacterial exacerbation of asthma, other non-allergic asthmas and "wheezy-infant syndrome", pneumoconiosis, including aluminosis, anthracosis, asbestosis, chalicosis, ptilosis, siderosis, silicosis, tabacosis and byssinosis;

(ii) Rheumatic diseases or autoimmune diseases or musculoskeletal diseases: all forms of rheumatic diseases, especially rheumatoid arthritis, acute rheumatic fever, and polymyalgia rheumatica; reactive arthritis; rheumatic soft tissue diseases; inflammatory soft tissue diseases of other genesis; arthritic symptoms in degenerative joint diseases (arthroses); tendinitis, bursitis, osteoarthritis, traumatic arthritis; collagenoses of any genesis, e.g., systemic lupus erythematosus, scleroderma, polymyositis, dermatomyositis, Sjögren syndrome, Still disease, Felty syndrome; and osteoporosis and other bone resorption diseases;

(iii) Allergic diseases: all forms of allergic reactions, e.g., angioneurotic edema, hay fever, insect bites, allergic reactions to drugs, blood derivatives, contrast agents, etc., anaphylactic shock (anaphylaxis), urticaria, angioneurotic edema, and contact dermatitis;

(iv) Vascular diseases: panarteritis nodosa, polyarteritis nodosa, periarteritis nodosa, arteritis temporalis, Wegner granulomatosis, giant cell arthritis, atherosclerosis, reperfusion injury and erythema nodosum;

(v) Dermatological diseases: e.g. dermatitis, psoriasis; sunburn, burns, eczema;

(vi) Renal diseases: e.g. nephrotic syndrome; and all types of nephritis, e.g., glomerulonephritis; pancreatits;

(vii) Hepatic diseases: e.g. acute liver cell disintegration; acute hepatitis of various genesis, e.g., viral, toxic, drug-induced; and chronically aggressive and/or chronically intermittent hepatitis;

(viii) Gastrointestinal diseases: e.g. inflammatory bowel diseases, irritable bowel syndrome, regional enteritis (Crohns disease), colitis ulcerosa; gastritis; aphthous ulcer, celiac disease, regional ileitis, gastroesophageal reflux disease;

(ix) Neuroprotection: e.g. in the treatment of neurodegeneration following stroke; cardiac arrest; pulmonary bypass; traumatic brain injury; spinal cord injury or the like;

(x) Eye diseases: allergic keratitis, uveitis, or iritis; conjunctivitis; blepharitis; neuritis nervi optici; choroiditis; glaucoma and sympathetic ophthalmia;

(xi) Diseases of the ear, nose, and throat (ENT) area: e.g. tinnitus; allergic rhinitis or hay fever; otitis externa; caused by contact eczema, infection, etc.; and otitis media;

(xii) Neurological diseases: e.g. brain edema, particularly tumor-related brain edema; multiple sclerosis; acute encephalomyelitis; meningitis; acute spinal cord injury; trauma; dementia, particularly degenerative dementia (including senile dementia, Alzheimer's disease; Parkinson's disease and Creutzfeldt-Jacob disease; Huntington's chorea, Pick's disease; motor neuron disease), vascular dementia (including multi-infarct dementia) as well as dementia associated with intracranial space occupying lesions; infections and related conditions (including HIV infection); Guillain-Barre syndrome; myasthenia gravis, stroke; and various forms of seizures, e.g., nodding spasms;

(xiii) Blood diseases: acquired hemolytic anemia; aplastic anemia, and idiopathic thrombocytopenia;

(xiv) Tumor diseases: acute lymphatic leukemia; Hodgkin's disease, malignant lymphoma; lymphogranulomatoses; lymphosarcoma; solid malignant tumors; extensive metastases;

(xv) Endocrine diseases: endocrine ophthalmopathy; endocrine orbitopathia; thyrotoxic crisis; Thyroiditis de Quervain; Hashimoto thyroiditis; Morbus Basedow; granulomatous thyroiditis; struma lymphomatosa; and Graves disease; type I diabetes (insulin-dependent diabetes);

(xvi) Organ and tissue transplantations and graft-versus-host diseases;

(xvii) Severe states of shock, e.g., septic shock, anaphylactic shock, and systemic inflammatory response syndrome (SIRS);

(xviii) Acute pain such as dental pain, perioperative, postoperative pain, traumatic pain, muscle pain, pain in burned skin, sun burn, trigeminal neuralgia, sun burn; spasm of the gastrointestinal tract or uterus, colics;

(xix) Visceral pain such as pain associated with chronic pelvic pain, pancreatitis, peptic ulcer, interstitial cystitis, renal colic, angina, dysmenorrhoea, menstruation, gynaecological pain, irritable bowel syndrome (IBS), non-ulcer dyspepsia, non-cardiac chest pain, myocardial ischemia;

(xx) Neuropathic pain such as low back pain, non-herpetic neuralgia, post herpetic neuralgia, diabetic neuropathy, nerve injury, acquired immune deficiency syndrome (AIDS) related neuropathic pain, head trauma, painful traumatic mononeuropathy, toxin and chemotherapy induced pain, phantom limb pain, painful polyneuropathy, thalamic pain syndrome, post-stroke pain, central nervous system injury, post surgical pain, stump pain, repetitive motion pain, pain induced by post mastectomy syndrome, multiple sclerosis, root avulsions, postthoracotomy syndrome, neuropathic pain associated hyperalgesia and allodynia.

(xxi) Inflammatory/nociceptive pain induced by or associated with disorders such as osteoarthritis, rheumatoid arthritis, rheumatic disease, teno-synovitis, gout, vulvodynia, myofascial pain (muscular injury, fibromyalgia), tendonitis, osteoarthritis, juvenile arthritis, spondylitis, gouty arthritis, psoriatic arthritis, muscoskeletal pain, fibromyalgia, sprains and strains, sympathetically maintained pain, myositis, pain associated with migraine, toothache, influenza and other viral infections such as the common cold, rheumatic fever, systemic lupus erythematosus;

(xxii) Cancer pain induced by or associated with tumors such as lymphatic leukemia; Hodgkin's disease, malignant lymphoma; lymphogranulomatoses; lympho sarcoma; solid malignant tumors; extensive metastases;

(xxiii) Headache such as cluster headache, migraine with and without aura, tension type headache, headache with different origins, headache disorders including prophylactic and acute use;

(xxiv) various other disease-states or conditions including, restenosis following percutaneous transluminal coronary angioplasty, acute and chronic pain, atherosclerosis, reperfusion injury, congestive heart failure, myocardial infarction, thermal injury, multiple organ injury secondary to trauma, necrotizing enterocolitis and syndromes associated with hemodialysis, leukopheresis, and granulocyte transfusion, sarcoidosis, gingivitis, pyrexia. edema resulting from trauma associated with burns, sprains or fracture, cerebral oedema and angioedema, Diabetes such as diabetic vasculopathy, diabetic neuropathy, diabetic retinopathy, post capillary resistance or diabetic symptoms associated with insulitis (e.g. hyperglycemia, diuresis, proteinuria and increased nitrite and kallikrein urinary excretion).

Other indications include: epilepsy, septic shock e.g. as antihypovolemic and/or antihypotensive agents, cancer, sepsis, osteoporosis, benign prostatic hyperplasia and hyperactive bladder, pruritis, vitiligo, general gastrointestinal disorders, disturbances of visceral motility at respiratory, genitourinary, gastrointestinal or vascular regions, wounds, burns, tissue damage and postoperative fever, syndromes associated with Itching.

Besides being useful for human treatment, these compounds are also useful for veterinary treatment of companion animals, exotic animals and farm animals, including mammals, rodents, and the like.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy*, 20th Edition, A. Gennaro (ed.), Lippincott Williams & Wilkins, 2000; *Handbook of Pharmaceutical Additives*, Michael & Irene Ash (eds.), Gower, 1995;

*Handbook of Pharmaceutical Excipients*, A. H. Kibbe (ed.), American Pharmaceutical Ass'n, 2000; H. C. Ansel and N. G. Popovish, *Pharmaceutical Dosage Forms and Drug Delivery Systems*, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

Pharmaceutical compositions suitable for buccal (sub-lingual) administration include lozenges comprising a compound of the present invention in a flavored base, usually sucrose, and acacia or tragacanth, and pastilles comprising the compound in an inert base such as gelatin and glycerin or sucrose and acacia.

Pharmaceutical compositions suitable for parenteral administration comprise sterile aqueous preparations of a compound of the present invention. These preparations are preferably administered intravenously, although administration can also be effected by means of subcutaneous, intramuscular, or intradermal injection. Injectable pharmaceutical formulations are commonly based upon injectable sterile saline, phosphate-buffered saline, oleaginous suspensions, or other injectable carriers known in the art and are generally rendered sterile and isotonic with the blood. The injectable pharmaceutical formulations may therefore be provided as a sterile injectable solution or suspension in a nontoxic parenterally acceptable diluent or solvent, including 1,3-butanediol, water, Ringer's solution, isotonic sodium chloride solution, fixed oils such as synthetic mono- or diglycerides, fatty acids such as oleic acid, and the like. Such injectable pharmaceutical formulations are formulated according to the known art using suitable dispersing or setting agents and suspending agents. Injectable compositions will generally contain from 0.1 to 5% w/w of a compound of the invention.

Solid dosage forms for oral administration of the compounds include capsules, tablets, pills, powders, and granules. For such oral administration, a pharmaceutically acceptable composition containing a compound(s) of the invention is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such solid pharmaceutical formulations may include formulations, as are well-known in the art, to provide prolonged or sustained delivery of the drug to the gastrointestinal tract by any number of mechanisms, which include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form.

Liquid dosage forms for oral administration of the compounds include emulsions, microemulsions, solutions, suspensions, syrups, and elixirs, optionally containing pharmaceutical adjuvants in a carrier, such as, for example, water, saline, aqueous dextrose, glycerol, ethanol and the like. These compositions can also contain additional adjuvants such as wetting, emulsifying, suspending, sweetening, flavoring, and perfuming agents.

Topical dosage forms of the compounds include ointments, pastes, creams, lotions, gels, powders, solutions, sprays, inhalants, eye ointments, eye or ear drops, impregnated dressings and aerosols, and may contain appropriate conventional additives such as preservatives, solvents to assist drug penetration and emollients in ointments and creams. Topical application may be once or more than once per day depending upon the usual medical considerations. Furthermore, preferred compounds for the present invention can be administered in intranasal form via topical use of suitable intranasal vehicles. The formulations may also contain compatible conventional carriers, such as cream or ointment bases and ethanol or oleyl alcohol for lotions. Such carriers may be present as from about 1% up to about 98% of the formulation, more usually they will form up to about 80% of the formulation.

Transdermal administration is also possible. Pharmaceutical compositions suitable for transdermal administration can be presented as discrete patches adapted to remain in intimate contact with the epidermis of the recipient for a prolonged period of time. To be administered in the form of a transdermal delivery system, the dosage administration will, of course, be continuous rather than intermittent throughout the dosage regimen. Such patches suitably contain a compound of the invention in an optionally buffered, aqueous solution, dissolved and/or dispersed in an adhesive, or dispersed in a polymer. A suitable concentration of the active compound is about 1% to 35%, preferably about 3% to 15%.

For administration by inhalation, the compounds of the invention are conveniently delivered in the form of an aerosol spray from a pump spray device not requiring a propellant gas or from a pressurized pack or a nebulizer with the use of a suitable propellant, e.g., dichlorodifluoromethane, trichlorofluoromethane, dichlorotetrafluoroethane, tetrafluoroethane, heptafluoropropane, carbon dioxide, or other suitable gas. In any case, the aerosol spray dosage unit may be determined by providing a valve to deliver a metered amount so that the resulting metered dose inhaler (MDI) is used to administer the compounds of the invention in a reproducible and controlled way. Such inhaler, nebulizer, or atomizer devices are known in the prior art, for example, in PCT International Publication Nos. WO 97/12687 (particularly FIG. 6 thereof, which is the basis for the commercial RESPIMAT® nebulizer); WO 94/07607; WO 97/12683; and WO 97/20590, to which reference is hereby made and each of which is incorporated herein by reference in their entireties.

Rectal administration can be effected utilizing unit dose suppositories in which the compound is admixed with low-melting water-soluble or insoluble solids such as fats, cocoa butter, glycerinated gelatin, hydrogenated vegetable oils, mixtures of polyethylene glycols of various molecular weights, or fatty acid esters of polyethylene glycols, or the like. The active compound is usually a minor component, often from about 0.05 to 10% by weight, with the remainder being the base component.

In all of the above pharmaceutical compositions, the compounds of the invention are formulated with an acceptable carrier or excipient. The carriers or excipients used must, of course, be acceptable in the sense of being compatible with the other ingredients of the composition and must not be deleterious to the patient. The carrier or excipient can be a solid or a liquid, or both, and is preferably formulated with the compound of the invention as a unit-dose composition, for example, a tablet, which can contain from 0.05% to 95% by weight of the active compound. Such carriers or excipients include inert fillers or diluents, binders, lubricants, disintegrating agents, solution retardants, resorption accelerators, absorption agents, and coloring agents. Suitable binders include starch, gelatin, natural sugars such as glucose or β-lactose, corn sweeteners, natural and synthetic gums such as acacia, tragacanth or sodium alginate, carboxymethylcellulose, polyethylene glycol, waxes, and the like. Lubricants include sodium oleate, sodium stearate, magnesium stearate, sodium benzoate, sodium acetate, sodium chloride, and the like. Disintegrators include starch, methyl cellulose, agar, bentonite, xanthan gum, and the like.

Pharmaceutically acceptable carriers and excipients encompass all the foregoing additives and the like.

The invention claimed is:

1. A compound of the formula (I)

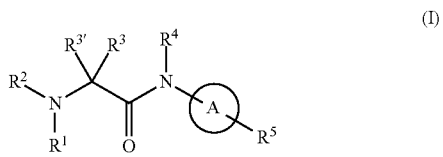

wherein:

ring A is a 5-membered heteroaryl ring;

$R^1$ is hydrogen, $C_{1-10}$ alkyl or $C_{3-10}$ cycloalkyl which is optionally substituted with 1-3 $C_{1-10}$ alkyl, each $R^1$ or it's substituent is optionally halogenated;

$R^2$ is methyl substituted with 1 heterocyclyl, each substituent on $R^2$ where possible is optionally halogenated or substituted with 1 to 3 $C_{1-6}$ alkyl, $C_{1-6}$ acyl, $C_{1-6}$ alkyl sulfonyl, cyano, aryl, oxo or hydroxyl;

$R^3$ and $R^{3'}$ are independently hydrogen or $C_{1-6}$ alkyl optionally halogenated with the proviso that $R^3$ and $R^{3'}$ cannot simultaneously be hydrogen;

$R^4$ is hydrogen or methyl;

$R^5$ is chosen from

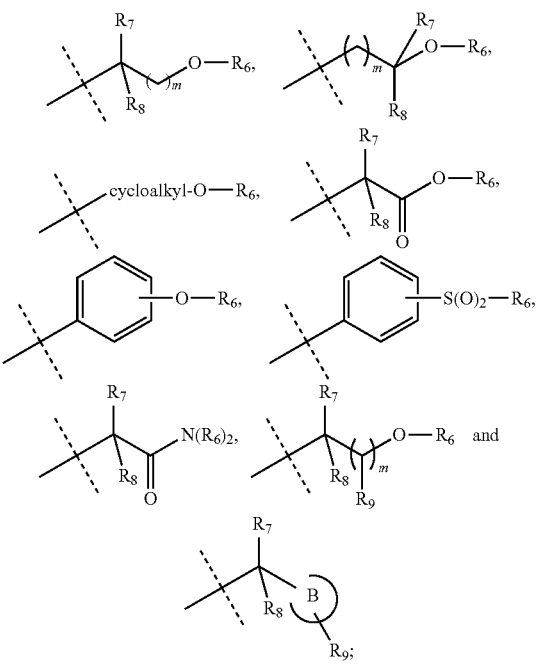

m is 0, 1, 2 or 3;

$R^6$ is hydrogen, $C_{1-4}$ alkyl or $C_{1-4}$ alkoxy;

$R^7$ and $R^8$ are each independently hydrogen, or $C_{1-4}$ alkyl with the proviso that both $R^7$ and $R^8$ cannot be hydrogen; and wherein $R^7$ and $R^8$ optionally can cyclize to form a $C_{3-7}$ cycloalkyl ring;

$R^9$ is $C_{1-6}$ alkyl or aryl;

ring B is a 5-6 membered heterocyclic ring;

n is 0, 1 or 2;

wherein any carbon atom on the formula (I) or any R substituent listed above is optionally partially or fully halogenated where possible;

or a pharmaceutically acceptable salt thereof.

2. The compound according to claim 1 and wherein ring A is

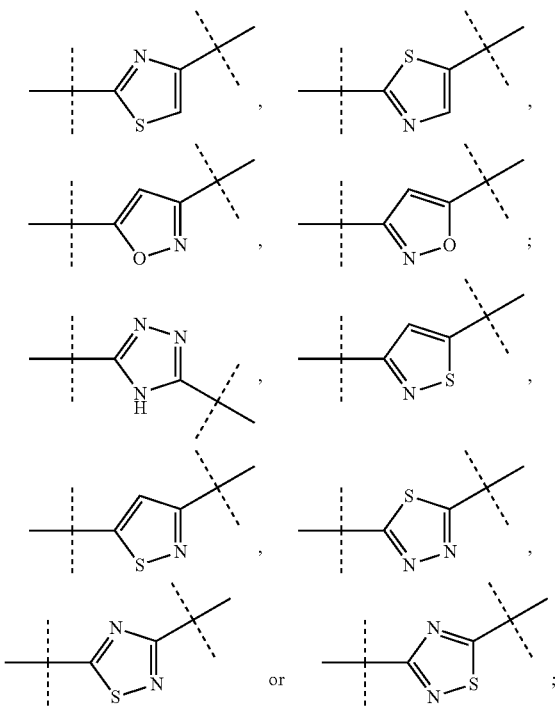

$R^2$ is methyl substituted with 1 heterocyclyl chosen from tetrahydropyranyl, dioxanyl, tetrahydrofuranyl, thiomorpholinyl, 1,1-dioxo-1λ$^6$-thiomorpholinyl, morpholinyl, pyrrolidinyl, piperidinyl and piperazinyl, each $R^2$ substituent where possible is optionally halogenated or substituted with 1 to 3 $C_{1-5}$ alkyl, $C_{1-5}$ acyl, methyl sulfonyl, cyano, phenyl, oxo or hydroxyl;

$R^3$ and $R^{3'}$ are each methyl or ethyl, each optionally halogenated.

3. The compound according to claim 2 and wherein ring A is

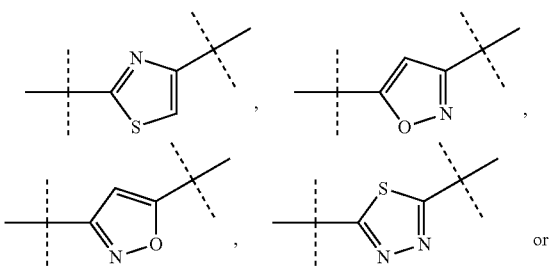

[triazole structure];

R¹ is hydrogen or $C_{1-3}$ alkyl optionally halogenated;

R² is methyl substituted with 1 heterocyclyl chosen from tetrahydropyranyl, dioxanyl, tetrahydrofuranyl, thiomorpholinyl, 1,1-dioxo-1λ⁶-thiomorpholinyl, morpholinyl, pyrrolidinyl, piperidinyl and piperazinyl each optionally halogenated or substituted with $C_{1-4}$ alkyl or methyl sulfonyl;

R³ and R³' are each methyl or ethyl;

R⁶ is hydrogen or $C_{1-2}$ alkyl;

R⁷ and R⁸ are each $C_{1-2}$ alkyl.

4. The compound according to claim 3 and wherein ring A is

[isoxazole structure] or [triazole structure];

R² is methyl optionally substituted with one heterocyclyl chosen from tetrahydropyranyl, dioxanyl, tetrahydrofuranyl, thiomorpholinyl, 1,1-dioxo-1λ⁶-thiomorpholinyl, morpholinyl, pyrrolidinyl, piperidinyl and piperazinyl each optionally halogenated or substituted with $C_{1-4}$ alkyl or methyl sulfonyl.

5. The compound according to claim 3, and wherein ring A is

[thiazole structure], [isoxazole structure],
[isoxazole structure], [thiadiazole structure],
[triazole structure];

R³ and R³' are methyl;

R⁶ is hydrogen or $C_{1-2}$ alkyl;

wherein R⁷ and R⁸ are each $C_{1-2}$ alkyl.

6. The compound according to claim 5, and wherein ring A is

[isoxazole structure], [triazole structure],
[isoxazole structure], [thiadiazole structure].

7. The compound according to claim 6 and wherein ring A is

[isoxazole structure] or [thiadiazole structure].

8. The compound according to claim 2, and wherein R² is tetrahydrofuranyl-CH₂—;

ring A is

[isoxazole structure] or [thiadiazole structure];

R⁵ is

[structure with R₇, R₈, $(\,)_m$, O—R₆]

wherein
wherein R⁷ and R⁸ optionally can cyclize to form a $C_{3-7}$ cycloalkyl ring.

9. The compound according to claim 2, and wherein ring A is

[isoxazole structure] or [thiadiazole structure];

R⁵ is

[structure with R₇, R₈, O—R₆] or [structure with R₇, R₈, R₉, O—R₆]

wherein
wherein R⁷ and R⁸ optionally can cyclize to form a C$_{3-7}$ cycloalkyl ring.

10. A compound of the formula (I) wherein the defintions: ring A, R¹, R², R³, R³', R⁴, R⁵, R⁶, R⁷, R⁸, R⁹, m, ring B, and n are as defined in claim 1 and wherein R⁷ and R⁶ can cyclize to form a 4-6 membered heterocyclic ring.

11. A compound of the formula (II)

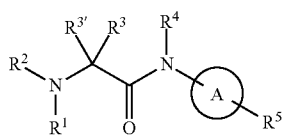

wherein

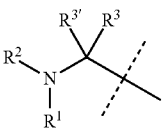

of the formula (II) is chosen from column A1-A8 in the table, and

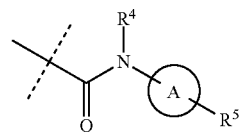

of the formula (II) is chosen from column B1-B19 in the table,

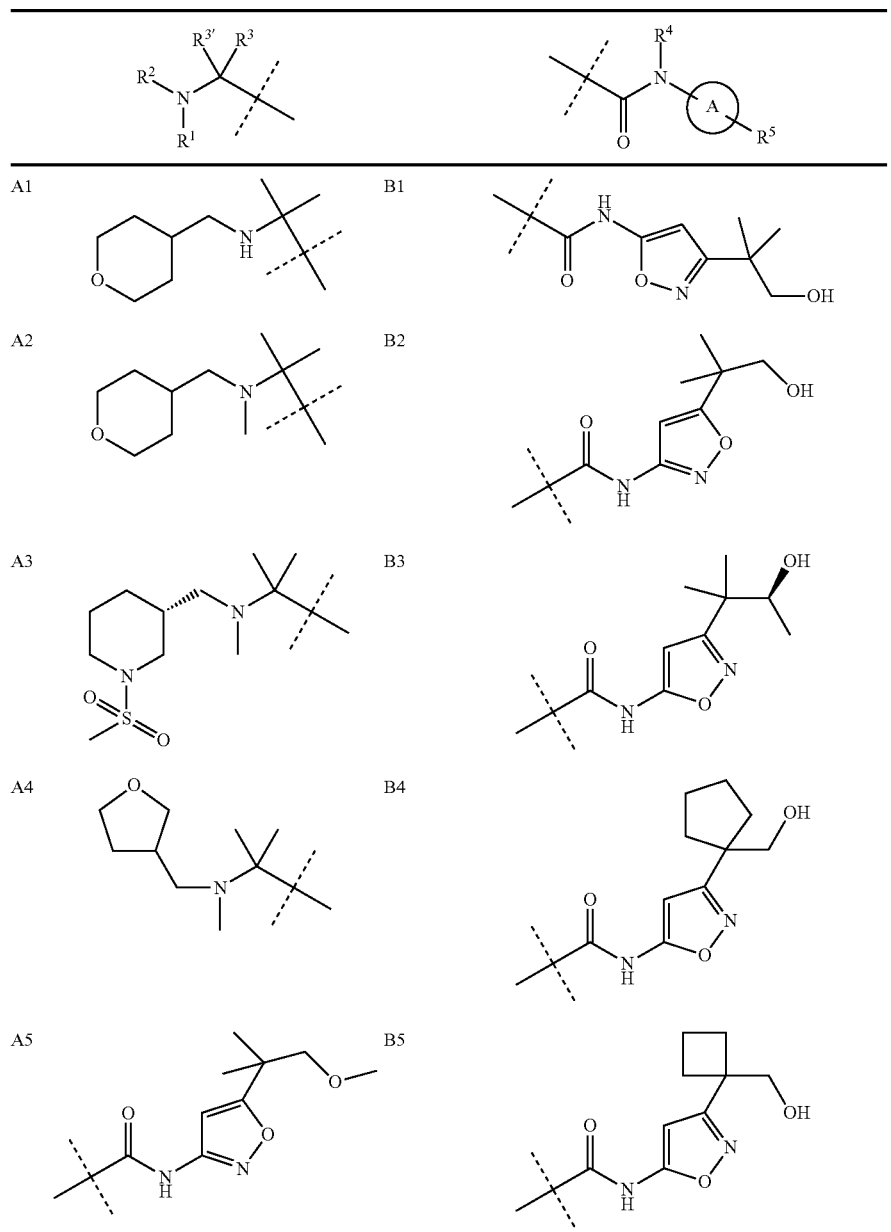

-continued
| | |
|---|---|
| A6 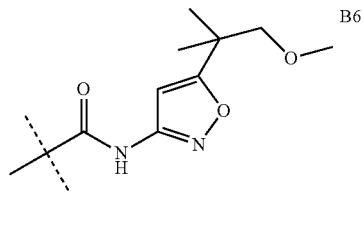 | B6 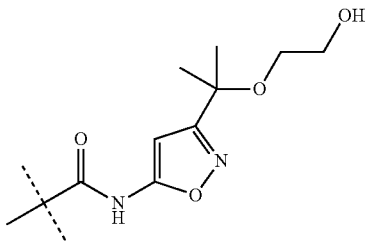 |
| A7 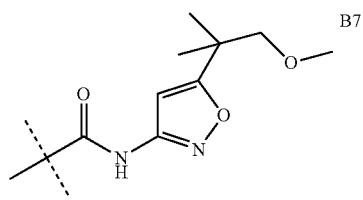 | B7 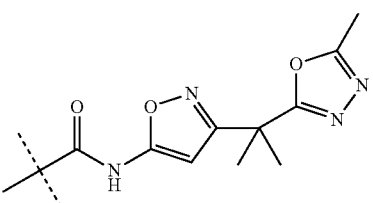 |
| A8 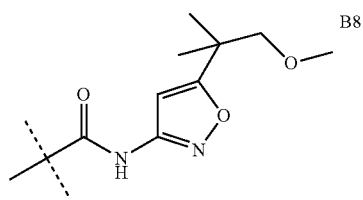 | B8 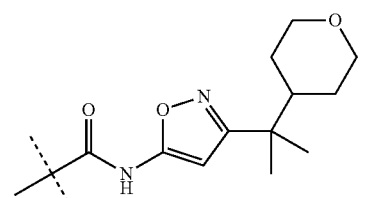 |
| | B9 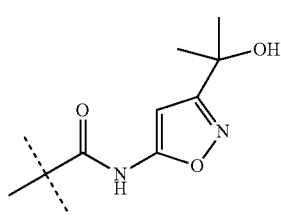 |
| | B10 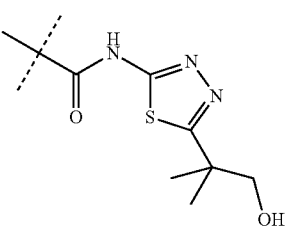 |
| | B11 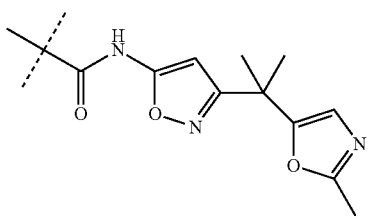 |

-continued
| 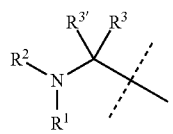 | 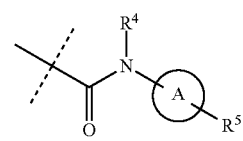 |
|---|---|
B12
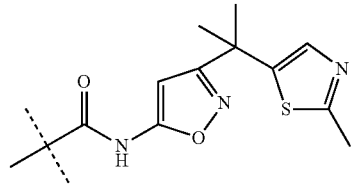
B13
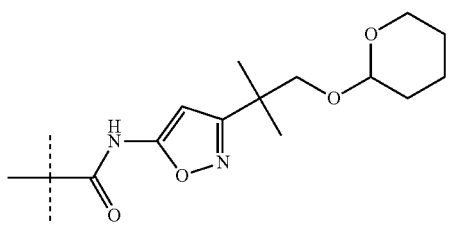
B14
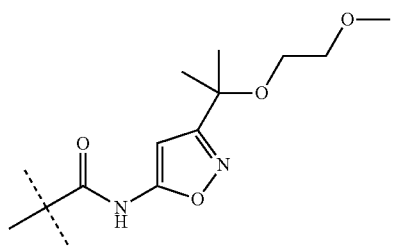
B15
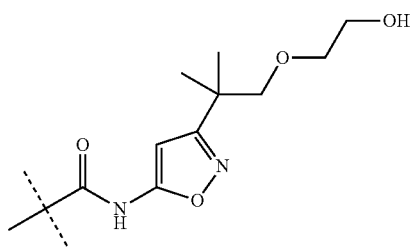
B16
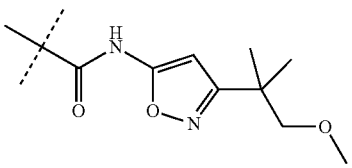
B17
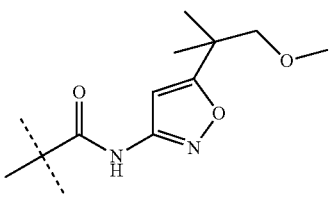

-continued
| 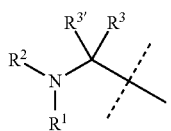 | 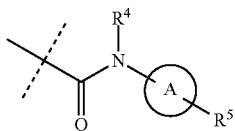 |
|---|---|
| B18 | 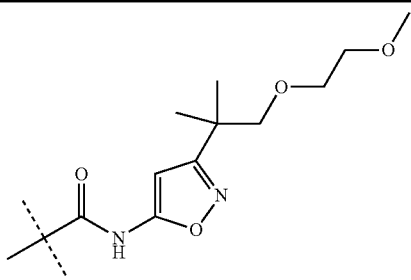 |
| B19 | 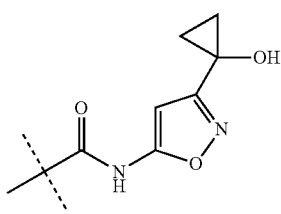 |
or a pharmaceutically acceptable salt thereof.
12. A compound chosen from
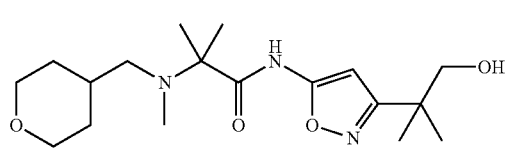
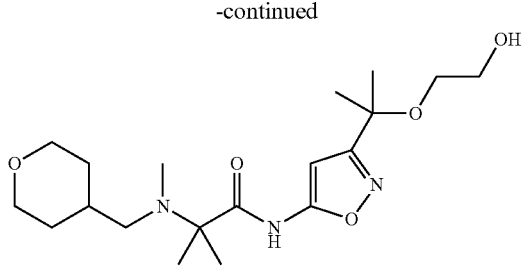
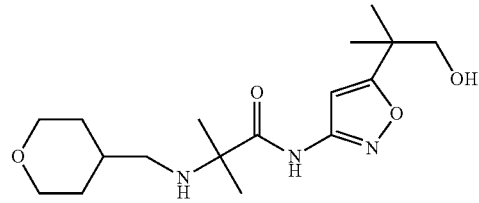
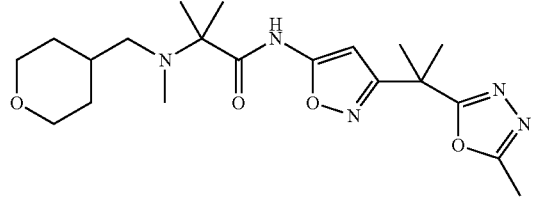
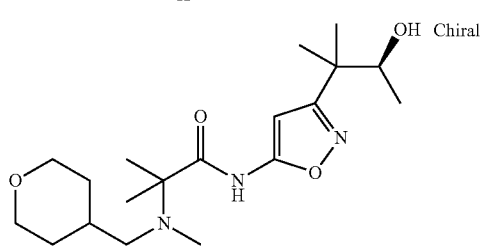
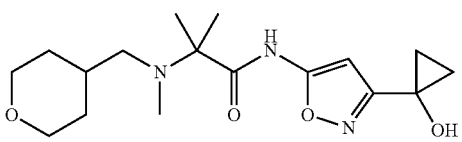
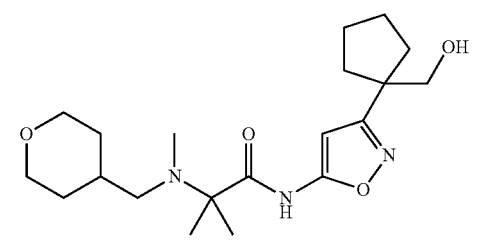
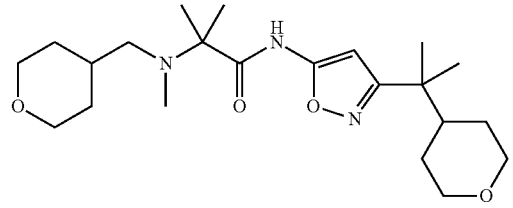

151
-continued
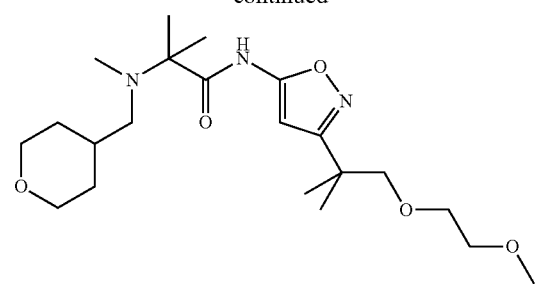
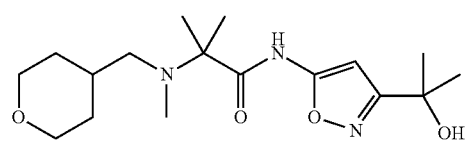
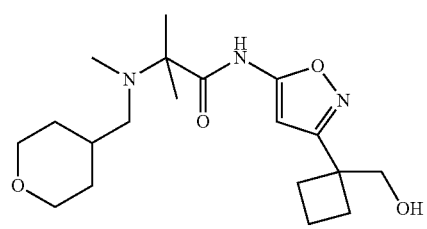
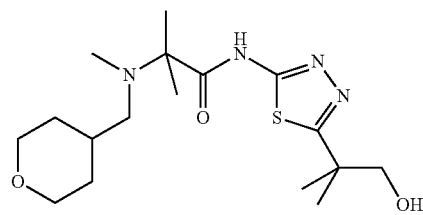
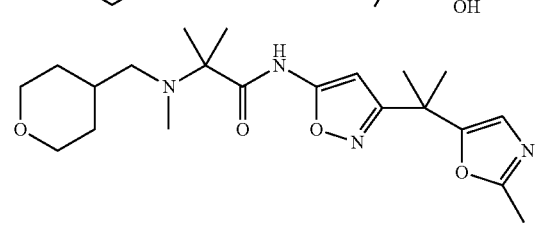
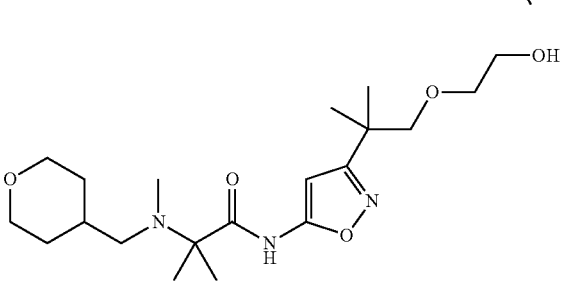
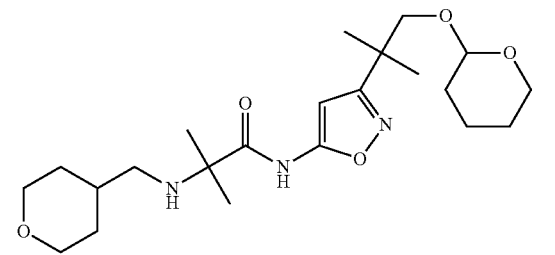
152
-continued
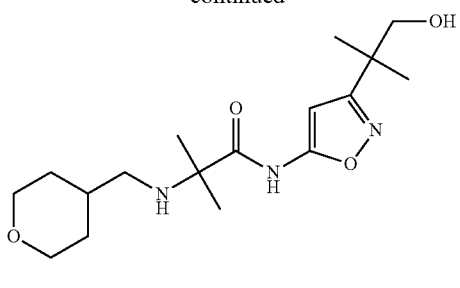
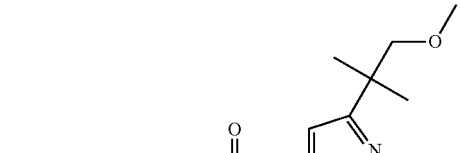
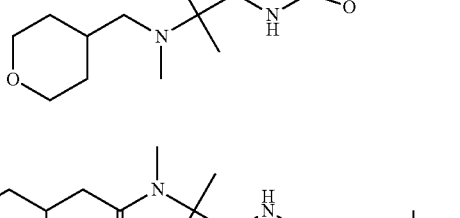
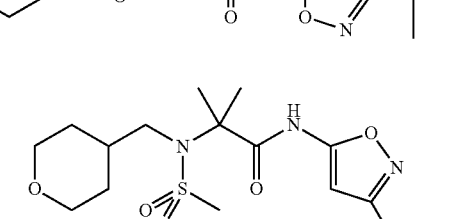
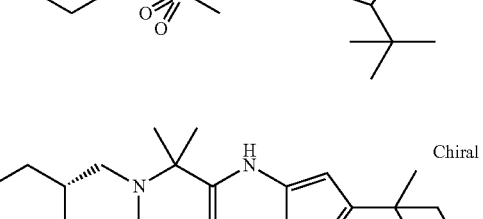
Chiral
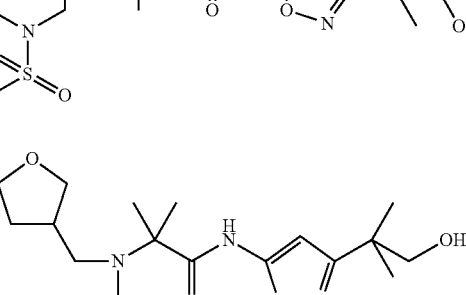
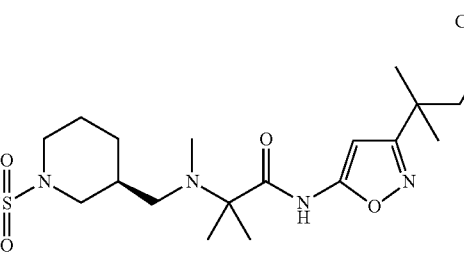
Chiral
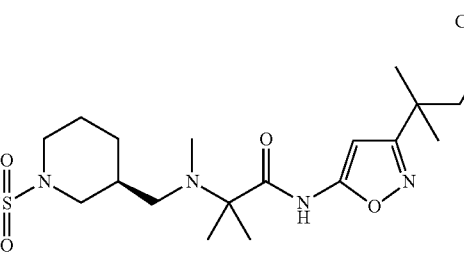

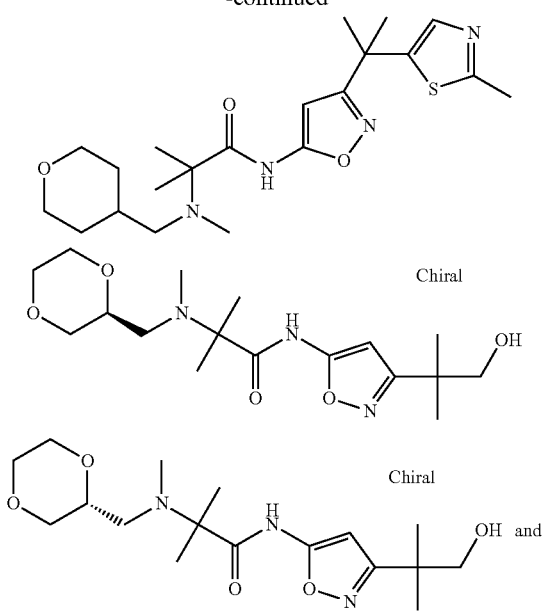

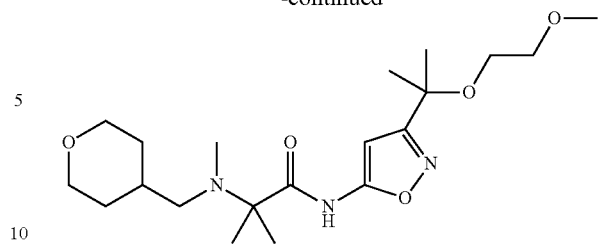

or a pharmaceutically acceptable salt thereof.

13. A pharmaceutical composition comprising a therapeutically effective amount of a compound according to claim 1 or 12 and one or more pharmaceutically acceptable carriers and/or adjuvants.

14. A method of treating pain comprising administering a therapeutically effective amount of a compound according to claim 1 or 12.

15. The method according to claim 14 wherein pain is chosen from acute pain, visceral pain, neuropathic pain, inflammatory and nociceptive pain, cancer pain and headache.

* * * * *